US012797265B2

(12) United States Patent
Varona et al.

(10) Patent No.: US 12,797,265 B2
(45) Date of Patent: Nov. 17, 2026

(54) ABSORBENT CORES WITH ENHANCED FIT AND ABSORBENCY

(71) Applicant: DSG TECHNOLOGY HOLDINGS LTD., Kwai Chung (HK)

(72) Inventors: Eugenio G. Varona, Marietta, GA (US); Russell Alexander Ables, Franklin, TN (US); Lars Herkstroeter, Halle (DE); Dennis Smid, Wolvega (NL); Andrew C. Wright, Pilsley (GB)

(73) Assignee: DSG Technology Holdings Ltd, Kwai Chung (HK)

( * ) Notice: Subject to any disclaimer, the term of this patent is extended or adjusted under 35 U.S.C. 154(b) by 1452 days.

(21) Appl. No.: 16/718,025

(22) Filed: Dec. 17, 2019

(65) Prior Publication Data

US 2020/0214910 A1 Jul. 9, 2020

Related U.S. Application Data

(60) Provisional application No. 62/780,781, filed on Dec. 17, 2018.

(51) Int. Cl.
*A61F 13/538* (2006.01)
*A61F 13/15* (2006.01)
(Continued)

(52) U.S. Cl.
CPC ...... *A61F 13/538* (2013.01); *A61F 13/15642* (2013.01); *A61F 13/49001* (2013.01);
(Continued)

(58) Field of Classification Search
CPC .... A61F 13/15; A61F 13/49; A61F 13/15642; A61F 13/4704; A61F 13/49001;
(Continued)

(56) References Cited

U.S. PATENT DOCUMENTS 4,699,823 A * 10/1987 Kellenberger ........ A61F 13/534 428/323
4,960,477 A * 10/1990 Mesek ................ A61F 13/5323 D24/126
(Continued)

FOREIGN PATENT DOCUMENTS

AU 2008237618 A1 5/2009
CN 1142758 A 2/1997
(Continued)

OTHER PUBLICATIONS

Notice of Office Action received in Japanese Application No. 2021-535042 mailed Jul. 18, 2023. [3 pages].
(Continued)

*Primary Examiner* — Michele Kidwell
(74) *Attorney, Agent, or Firm* — Alberto Q. Amatong, Jr.; Amatong McCoy LLC

(57) ABSTRACT

An absorbent core is disclosed. The core includes a first absorbent core construction having multiple spaced-apart sections of a fibrous construction having a fiber structure. A first nonwoven sheet is positioned above the fibrous construction. A second nonwoven sheet is positioned below the fibrous construction. The first nonwoven sheet is coupled with the second nonwoven sheet at locations between adjacent sections of the multiple spaced-apart sections of the fibrous construction. Absorbent material is disposed within the fiber structure, between the first and second nonwoven sheets.

43 Claims, 33 Drawing Sheets

(51) Int. Cl.
*A61F 13/45* (2006.01)
*A61F 13/47* (2006.01)
*A61F 13/49* (2006.01)
*A61F 13/514* (2006.01)

(52) U.S. Cl.
CPC *A61F 13/49007* (2013.01); *A61F 2013/4531* (2013.01); *A61F 13/4704* (2013.01); *A61F 2013/51452* (2013.01)

(58) Field of Classification Search
CPC .............. A61F 13/49007; A61F 13/538; A61F 2013/4531; A61F 2013/51452
See application file for complete search history.

(56) References Cited

U.S. PATENT DOCUMENTS 5,061,259 A 10/1991 Goldman et al.
5,151,091 A * 9/1992 Glaug ............... A61F 13/53717 604/385.101
5,171,302 A 12/1992 Buell
5,197,959 A 3/1993 Buell
5,198,057 A 3/1993 Newkirk et al.
5,252,275 A 10/1993 Sultze et al.
5,458,592 A 10/1995 Abuto et al.
5,464,402 A * 11/1995 Zajaczkowski ....... A61F 13/493 604/378
5,545,156 A 8/1996 DiPalma et al.
5,591,150 A 1/1997 Olsen et al.
5,599,336 A 2/1997 Plischke
5,679,042 A 10/1997 Varona
5,846,230 A 12/1998 Osborn, III et al.
5,974,631 A 11/1999 Leifeld
6,071,549 A 6/2000 Hansen
6,150,002 A 11/2000 Varona
6,160,197 A 12/2000 Lassen et al.
6,197,404 B1 3/2001 Varona
6,221,460 B1 4/2001 Weber et al.
6,348,253 B1 * 2/2002 Daley .................. A61F 13/512 428/152
6,432,094 B1 8/2002 Fujioka et al.
6,575,948 B1 6/2003 Kashiwagi et al.
6,632,209 B1 10/2003 Chmielewski
6,673,980 B1 1/2004 Varona et al.
6,706,129 B2 3/2004 Ando et al.
6,794,557 B1 9/2004 Klemp et al.
6,797,360 B2 9/2004 Varona
6,838,154 B1 1/2005 Varona et al.
7,078,583 B2 7/2006 Kudo et al.
7,132,585 B2 11/2006 Kudo et al.
7,722,590 B2 5/2010 Tsuji et al.
7,847,144 B2 12/2010 Beruda et al.
8,114,059 B2 2/2012 Ehrnsperger et al.
8,148,598 B2 4/2012 Tsang et al.
8,268,424 B1 9/2012 Suzuki et al.
8,361,047 B2 1/2013 Mukai et al.
8,466,336 B2 6/2013 Carlucci et al.
8,568,566 B2 10/2013 Jackels et al.
8,603,277 B2 12/2013 Paldey et al.
8,764,719 B2 7/2014 Bissah et al.
8,979,815 B2 3/2015 Roe et al.
9,044,359 B2 6/2015 Wciorka et al.
9,216,116 B2 12/2015 Roe et al.
9,216,118 B2 12/2015 Roe et al.
9,233,185 B2 1/2016 Noda et al.
9,241,845 B2 1/2016 Hundorf et al.
9,295,593 B2 3/2016 Malderen
9,326,896 B2 5/2016 Schäfer et al.
9,468,566 B2 10/2016 Rosati et al.
9,492,328 B2 11/2016 Jackels et al.
9,532,910 B2 1/2017 Rosati et al.
9,566,198 B2 2/2017 Wright et al.
9,603,750 B2 3/2017 Maele
9,707,135 B2 7/2017 Sheldon et al.
9,713,556 B2 7/2017 Arizti et al.
9,713,557 B2 7/2017 Arizti et al.
9,789,009 B2 10/2017 Joseph
9,789,011 B2 10/2017 Roe et al.
9,789,014 B2 10/2017 Wright et al.
9,974,699 B2 5/2018 Kreuzer et al.
9,987,176 B2 6/2018 Roe et al.
10,016,316 B2 7/2018 Sakaguchi et al.
10,071,002 B2 9/2018 Bianchi et al.
10,201,462 B2 2/2019 Wright et al.
10,470,948 B2 11/2019 Busam et al.
10,561,546 B2 2/2020 Rosati et al.
10,583,053 B2 3/2020 Robles et al.
10,660,800 B2 5/2020 Becker et al.
10,869,787 B2 12/2020 Ehrnsperger et al.
10,893,987 B2 1/2021 Kreuzer et al.
2002/0055726 A1 5/2002 Costa
2003/0083631 A1 5/2003 Chen et al.
2003/0129915 A1 7/2003 Harriz
2003/0167046 A1 9/2003 Klemp et al.
2004/0054342 A1 3/2004 Newbill et al.
2004/0087923 A1 5/2004 Cole
2004/0193128 A1 9/2004 Klemp et al.
2004/0204697 A1 10/2004 Litvay
2005/0137558 A1 6/2005 Mizutani et al.
2005/0224200 A1 10/2005 Bouchard et al.
2006/0069367 A1 3/2006 Waksmundzki et al.
2006/0184146 A1 8/2006 Suzuki
2007/0244453 A1 10/2007 Yasumura et al.
2009/0076473 A1 3/2009 Kasai et al.
2009/0087636 A1 4/2009 Yasuda et al.
2009/0112175 A1 4/2009 Bissah et al.
2010/0318047 A1 12/2010 Ducker et al.
2011/0052861 A1 3/2011 Rock
2012/0289923 A1 11/2012 Watabe et al.
2013/0046267 A1 2/2013 Brinkley
2013/0079741 A1 3/2013 Nakashita et al.
2014/0276518 A1 9/2014 Varona et al.
2014/0303582 A1 * 10/2014 Wright .............. A61F 13/15658 156/60
2015/0045756 A1 2/2015 Wright et al.
2015/0065973 A1 * 3/2015 Roe ....................... A61F 13/533 604/374
2015/0065975 A1 * 3/2015 Roe ................... A61F 13/49001 604/374
2015/0342801 A1 * 12/2015 Bianchi ............... A61F 13/5323 156/278
2016/0199527 A1 7/2016 Ota et al.
2016/0235595 A1 * 8/2016 Ehrnsperger .......... A61F 13/536
2016/0331602 A1 * 11/2016 Bianchi ................. A61F 13/514
2017/0181902 A1 6/2017 Wright et al.
2018/0064583 A1 3/2018 Maele
2019/0290505 A1 9/2019 Varona et al.
2020/0330291 A1 10/2020 Lindner et al.

FOREIGN PATENT DOCUMENTS

CN 1859931 A 11/2006
CN 101219078 A 7/2008
CN 101427962 A 5/2009
CN 102014826 A 4/2011
CN 101151010 B 6/2012
CN 102858295 A 1/2013
CN 104619289 A 5/2015
CN 102802581 A 6/2015
CN 104736116 A 6/2015
CN 107109731 A 8/2017
CN 107205868 A 9/2017
CN 108670556 A 10/2018
DE 202005017004 U1 1/2006
EP 1800638 A1 6/2007
EP 1920744 A1 5/2008
EP 2550946 A1 1/2013
EP 2630939 A1 8/2013
EP 2157953 B1 7/2015
EP 2907493 8/2015
EP 2928432 B1 9/2017
EP 2907493 B1 11/2017
EP 3210583 B1 7/2018

(56) References Cited

FOREIGN PATENT DOCUMENTS

| | | | |
|---|---|---|---|
| JP | 58502005 | A | 11/1983 |
| JP | 02-084623 | U1 | 7/1990 |
| JP | 2000201975 | A | 7/2000 |
| JP | 2001171029 | A | 6/2001 |
| JP | 2007061171 | A | 3/2007 |
| JP | 5503225 | B2 | 5/2014 |
| JP | 2018166557 | A | 11/2018 |
| WO | 8301965 | A1 | 6/1983 |
| WO | 1999001095 | A1 | 1/1999 |
| WO | 2006135018 | A1 | 12/2006 |
| WO | 2012149073 | A1 | 11/2012 |
| WO | 2016108039 | A1 | 7/2016 |
| WO | 2016157653 | A1 | 10/2016 |

OTHER PUBLICATIONS

Supplementary Search Report and Written Opinion issued in European Patent Application No. EP 19897800.9, mailed Aug. 25, 2022. [10 pages].

International Preliminary Report on Patentability issued in PCT Application No. PCT/US2019/066982, mailed Apr. 14, 2021; 51 pages.

International Search Report and Written Opinion mailed Apr. 23, 2020 (issued in PCT Application No. PCT/US2019/066982) [28 pages].

* cited by examiner

ABSORBENT CORES WITH ENHANCED FIT AND ABSORBENCY

CROSS-REFERENCE TO RELATED APPLICATIONS

The present application claims the benefit of U.S. Provisional Patent Application No. 62/780,781, filed on Dec. 17, 2018, entitled "Absorbent Cores with Enhanced Fit and Absorbency", the entirety of which is incorporated herein by reference.

FIELD

The present disclosure relates generally to absorbent cores or absorbent core composites, disposable absorbent articles that incorporate the absorbent core or core composites, and systems (apparatus) and methods of making such and other related products. Disposable absorbent articles to which the present disclosure is particularly applicable include baby diapers, training pants, adult incontinence products, feminine hygiene articles, and the like. The absorbent core composites are particularly suited for providing a central absorbent construction of a disposable absorbent garment that is worn in conformance with the user's anatomy.

BACKGROUND

Typically, absorbent cores compromise fit for increased absorbency, or compromise increased absorbency for a better fit. For example, some absorbent cores are cut along the lateral edges to create an hourglass shape to provide a better fit. However, such cutting in the crotch region reduces the absorbent material concentrated in this critical absorption zone; thereby, sacrificing absorbency to achieve a better fit. Absorbent cores that are not thusly cut, may exhibit a greater degree of absorbency, but will have a bulky, uncomfortable fit between the user's thighs.

It would be desirable to have an absorbent core that is capable of achieving a comfortable fit for the user, without sacrificing the degree of absorbency of the core.

SUMMARY

Some embodiments of the present disclosure include an absorbent core having a longitudinal centerline and a lateral centerline that is transverse to the longitudinal centerline. The absorbent core includes a first absorbent core construction. The first absorbent core construction includes a plurality of laterally spaced-apart fibrous constructions. Each fibrous construction extends generally parallel to or coincident with the longitudinal centerline, and each fibrous construction includes a nonwoven. A first nonwoven sheet is positioned on a first side of the fibrous constructions. A second nonwoven sheet is positioned on a second side of the fibrous constructions, opposite the first side of the fibrous construction. The first nonwoven sheet is coupled with the second nonwoven sheet at locations between adjacent, laterally spaced-apart fibrous constructions. Absorbent material is disposed within the nonwoven of each fibrous construction. The absorbent material is positioned between the first and second nonwoven sheets.

Some embodiments of the present disclosure include an absorbent article that includes an absorbent core and a chassis that includes a backsheet and a topsheet. The absorbent core is positioned between the topsheet and the backsheet and is coupled with the backsheet. The absorbent core has a longitudinal centerline and a lateral centerline that is transverse to the longitudinal centerline. The absorbent core includes a first absorbent core construction. The first absorbent core construction includes a plurality of laterally spaced-apart fibrous constructions. Each fibrous construction extends generally parallel to or coincident with the longitudinal centerline, and each fibrous construction includes a nonwoven. A first nonwoven sheet is positioned on a first side of the fibrous constructions, and a second nonwoven sheet is positioned on a second side of the fibrous constructions, opposite the first side of the fibrous construction. The first nonwoven sheet is coupled with the second nonwoven sheet at locations between adjacent, laterally spaced-apart fibrous constructions. Absorbent material is disposed within the nonwoven of each fibrous construction. The absorbent material is positioned between the first and second nonwoven sheets.

Some embodiments of the present disclosure include a method of making a fibrous construction includes a composite of absorbent material and a nonwoven. The method includes providing a nonwoven having a first surface and a second surface. The method includes passing a forced airstream containing absorbent material onto and through the first surface of the nonwoven. At least some of the absorbent material is captured within the nonwoven, between the first surface and the second surface. The method includes filtering at least some of the absorbent material at least partially through the nonwoven such that a gradient distribution of particle sizes of the absorbent material is formed within the nonwoven, between the first surface and the second surface.

Some embodiments of the present disclosure include a system for introducing absorbent material into a nonwoven. The system includes a nonwoven conveyer, and a chamber including an input and an output. The nonwoven conveyer intersects the chamber between the input and the output. A forced airstream generator is positioned to generate a force air stream through the chamber. An absorbent material source is positioned to provide absorbent material into the chamber.

Some embodiments of the present disclosure include a method of making an absorbent core having a longitudinal centerline and a lateral centerline that is transverse to the longitudinal centerline. The method includes combining a nonwoven with absorbent material to form a fibrous construction, separating the fibrous construction into multiple fibrous constructions, and coupling a first nonwoven sheet onto a first surface of the fibrous constructions, wherein the multiple fibrous constructions are laterally spaced-apart. The method includes positioning a second nonwoven sheet onto a second surface of the fibrous constructions, opposite the first surface, and coupling the first nonwoven sheet with the second nonwoven sheet along adhesion lines that extend between adjacent, laterally spaced-apart fibrous constructions, forming a first absorbent core construction. In some embodiments, the absorbent core is used in the making of an absorbent article by positioning the absorbent core within a chassis, between a backsheet and a topsheet of the chassis, including coupling the absorbent core with the backsheet.

Some embodiments of the present disclosure include a roller for forming an undulated topsheet of an absorbent core. The roller includes a body, a roller surface, and grooves formed on the roller surface.

Some embodiments of the present disclosure include a system for making an absorbent core. The system includes a nonwoven conveyer, and a chamber including an input and an output, wherein the nonwoven conveyer intersects the chamber between the input and the output. The system includes a forced airstream generator positioned generate a force air stream through the chamber, and an absorbent material source positioned to provide absorbent material into the chamber. The system includes a top nonwoven sheet conveyer positioned to convey a top nonwoven sheet, and a combining roller positioned to receive a top nonwoven sheet from the top nonwoven sheet conveyer and a nonwoven from the nonwoven conveyer, and arranged to combined a nonwoven with a top nonwoven sheet.

DETAILED DESCRIPTION

Figure 1:
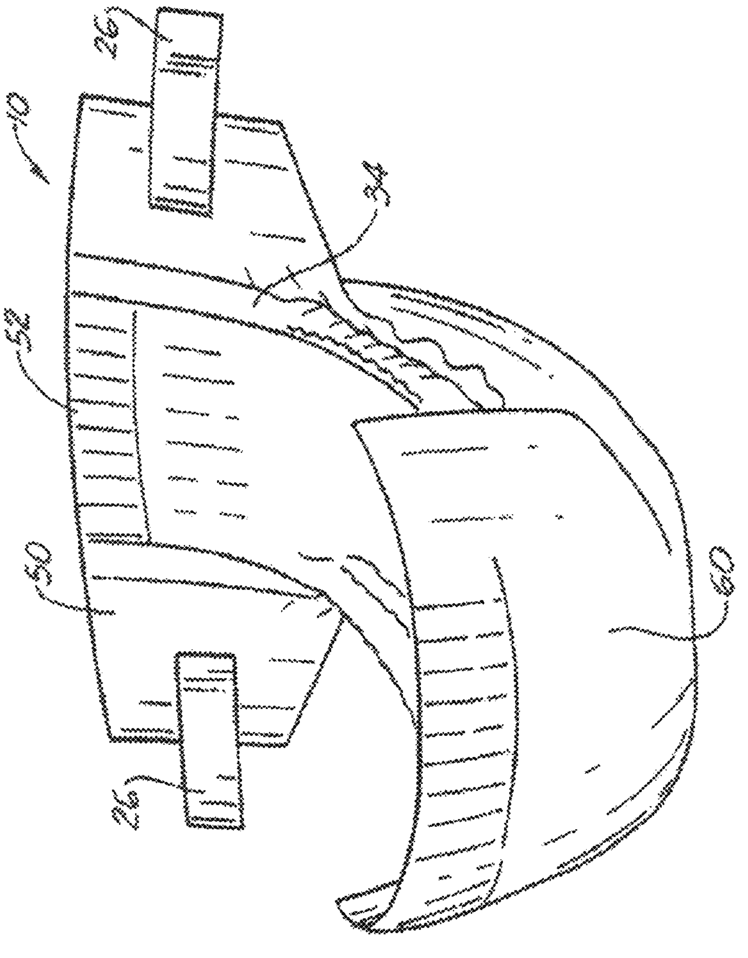
FIG. 1 is a perspective view of a disposable absorbent article within which an absorbent core composite, the article and the core composite each in accordance with the present disclosure may be incorporated.

The present disclosure, and the systems, apparatus, and methods described, relate generally to absorbent core composites and disposable absorbent articles incorporating same. Such disposable absorbent articles include baby diapers, training pants, adult incontinence products, feminine hygiene articles, and the like. To facilitate the present description, many aspects are described in respect to diapers. The disclosure extends, of course, to applications beyond diapers.

Definitions

For purposes of the present description of various aspects of the disclosure, an absorbent core composite or construction refers to a cohesive arrangement of multiple components or sections, including one or more sections or components comprised or populated by an absorbent material. As with the term "composite", the term "construction" may, in one respect, refer to such a cohesive arrangement of multiple sections or components that together define an absorbent body. Such an absorbent body may then be incorporated into a disposable absorbent article or garment and provide an absorbent core for the article. In some diaper or training pants applications, another cover layer (e.g., a nonwoven or nonwoven tissue) may encase or lay above the absorbent core (and may be included in defining the absorbent core of the article). Further, the absorbent article may provide one or more impermeable backsheets, a topsheet, and further, one or more acquisition distribution layers (ADLs) and/or tissue layers about or adjacent the absorbent core.

In certain applications, the preferred absorbent core construction includes a primary or central absorbent construction positioned for initial receipt (bodyside) in the crotch region of the disposable absorbent article. In designs employing multiple absorbent layers or absorbent cores, the primary absorbent construction may also be referred to as an upper absorbent layer, upper core, upper absorbent construction, or upper core layer.

The absorbent construction in exemplary applications is framed by a fibrous construction or network of fibers, and thus, the upper or primary absorbent construction may be referred to as a fibrous layer or fibrous construction.

As used herein, "NW" refers to a nonwoven fabric. In certain applications, the upper core construction is preferably framed and primarily constituted of a bulky nonwoven (also referred to as a high loft nonwoven), such as an air-through nonwoven. At least some of the nonwoven layers disclosed herein may be a meltblown nonwoven, a spunbond nonwoven, or any combination thereof (e.g., such as a spunbond-meltblown-spunbond (SMS) nonwoven). Furthermore, each nonwoven layer disclosed herein may be a "tissue" or "tissue layer", which is a cellulose-based (paper) nonwoven as opposed to a synthetic nonwoven. Fibers of any of the nonwovens disclosed herein may include, but are not limited to, fibers composed of polypropylene (PP), polyethylene (PE), polyethylene terephthalate (PET), polylactic acid (PLA), other polyolefins, copolymers thereof and any combination thereof, including bicomponent fibers. The fibers may be treated with a surface-active agent, surfactant, to modify the surface tension of the fibers so that they are hydrophilic. In some aspects, the NW layers used in the absorbent core composites disclosed herein are selected based upon pore size of the fabric, fiber wettability of the fabric, or combinations thereof.

As used herein, the density of a nonwoven, including of a bulky nonwoven, is determined in accordance with the following Equation 1: Density (ρ)=mass (m)/volume (v)=mass/(length (l)×width (w)×thickness (t)). The International Nonwovens and Disposables Association (INDA) and the European Disposables and Nonwovens Association (EDANA) provide test methods that, although do not include a specific method for density, provide tests that allow one skilled in the art to arrive at the density value using the above Equation 1. Test method NWSP 120.2.R0 (15), set forth by INDA and EDANA, provides a means to measure the thickness (t) of a bulky nonwoven, also referred to as a high loft nonwoven. Test method NWSP 130.1.R0 (15), set forth by INDA and EDANA, provides means to measure the mass per unit area or basis weight (bw). Once thickness of the bulky nonwoven and the mass per unit area of the bulky nonwoven is determined in accordance with NWSP 120.2.R0 (15) and NWSP 130.1.R0 (15), the density may be determined:

$$\text{Density } (\rho)=m/v=m/(l\times w\times t) \qquad \text{(Equation 1)}$$

$$\text{Mass per unit area (bw)}=m/(l\times w) \qquad \text{(Equation 2); therefore,}$$

$$\rho=\text{bw}/t \qquad \text{(Equation 3)}$$

As used herein "BNW" refers to a "bulky nonwoven". Bulky nonwovens, in comparison to non-bulky nonwovens, are thicker at low to medium basis weights. Air-through nonwoven is a type of bulky nonwoven, and denotes the manufacturing method for production of nonwoven where hot air is blown through a carded nonwoven to thermally bond the fibers. Other bulky nonwoven types include resin bonded nonwovens, and other carded nonwovens. The "bulky nonwoven" referred to herein may be and provides, an open, fibrous network or web of hydrophilic but non-absorbent fibers. Furthermore, as used herein, a bulky nonwoven is a fibrous web material having a thickness of between 100 μm and 10,000 μm (preferably 1,000 μm to 5,000 μm), basis weight between 15 $g/m^2$ and 200 $g/m^2$ (preferably, between 20 $g/m^2$ and 80 $g/m^2$), and density between 0.01 g/cc and 0.3 g/cc (preferably between 0.01-0.08 g/cc). Moreover, the bulky nonwoven will have an effective pore diameter between 300 μm to 2000 μm. The effective pore diameter is estimated from web density, fiber diameter and fiber density values following the method of Dunstan & White, J. Colloid Interface Sci, 111 (1986), 60 wherein effective pore diameter=4*(1−solid volume fraction)/(solid volume fraction*solid density*solid specific surface area).

As used herein "crepe spunbond" refers to a web of thermoplastic nonwoven subjected to a creping process that produces a bulky structure with substantial fiber looping between the bond areas in the base spunbond sheet. Crepe spunbonds may include, but are not limited to those disclosed in U.S. Pat. Nos. 6,197,404; 6,150,002; 6,797,360; 6,673,980; 6,838,154, each of which is incorporated herein by reference.

As used herein, "bulkifying" or "bulkification" refers to a treatment and/or process that results in a decrease of the bulk density and an increase of the void volume (porosity of the nonwoven web) and specific volume (i.e., the inverse of density) of a nonwoven relative to the bulk density and void volume of the nonwoven prior to "bulkifying". After being subjected to "bulkifying", such a nonwoven is sometimes referred to herein as a "bulkified nonwoven".

As used herein, "BBNW" refers to a nonwoven, optionally a bulky nonwoven, that has been at least partially bulkified.

As used herein, an "open fibrous layer" refers to a fibrous construction having relatively large pore sizes, i.e. larger gaps between the fibers than another fibrous construction with smaller pore sizes. An "open" fibrous layer has a lower fiber density (fewer fiber per cubic area) and/or narrower fibers (lower denier) and/or less crimped fibers.

Any of the nonwovens disclosed herein may form a top sheet or cover layer of the absorbent core composites, a base layer or substrate or back sheet of the absorbent composite, an intermediate layer of the absorbent core composite (positioned between the top sheet and back sheet), or any combination thereof.

As used herein, "fluff" is cellulose wood pulp typically made from pine. The base material for fluff is often provided in the form of a sheet, similar to thick paper, which is then made into fluff using a hammermill.

As used herein, "dry integrity" refers to the structural and positional integrity of the core or article when in a dry state, such as during manufacture, packaging, shipping, and storage.

As sued herein, "wet integrity" refers to the structural and positional integrity of the core or article when in a wet state, such as during use, when insulted.

As used herein, "structural integrity" refers to the ability of a single component of the core or article to maintain its structure and not to deform.

As used herein, "positional integrity" refers to the ability of a component of the core or article to maintain its structure and position (i.e., not deform or move) relative to other components of the core or article. For example, SAP with wet integrity does not migrate within the core during swelling of the SAP.

As used herein, "SAP-free" and "absorbent material-free" refers to surface area on a nonwoven substrate that lacks absorbent material.

As used herein, "absorbent layer" and "absorbent material layer" and "AML" refer to a layer composed of at least one absorbent material capable of absorbing and retaining at least some liquid. Any of the absorbent materials disclosed herein may be or include SAP (high or super absorbent polymer), which may be composed of polyvinyl alcohol, polyacrylate, any of various grafted starches, or cross-linked sodium polyacrylate, for example. While described as particles herein, the SAP may be in the form of particles, fibers, foams, web, spheres, agglomerates of regular or irregular shapes, and film. In some aspects, the SAP is combined with an absorbent matrix, which may be a de-fiberized wood pulp or similar material. In other aspects the SAP, and the absorbent core composite as a whole, lacks an absorbent matrix. In some aspects, at least one set of the plurality of SAP particles are mixed with at least one other particle. Such other, non-SAP particles may include, but are not limited to, hot melt adhesive particles, binder particles, spacer particles, or other particles. While "SAP" is used to refer to the absorbent material used in many of the specific embodiments shown and/or described in the present disclosure, it is understood that the "SAP" in any such embodiments may be replaced with another absorbent material. For example, the "SAP-free lanes" disclosed herein may be "absorbent material-free lanes". In some aspects, the absorbent materials used herein are selected based upon the intrinsic superabsorbent properties, including gel bed permeability, absorption speed (vortex), absorbent capacity (CRC), and particle size.

As used herein, "absorbent constitution" refers to a construction or composite, or portion thereof, that provides fluid retention functionality to a layer or construction. For example, in some aspects of the upper absorbent construction, the fibrous construction having SAP (or other absorbent material) deposited therein may form the absorbent constitution, while the nonwoven sheets encasing the fibrous construction having SAP (or other absorbent material) deposited therein do not constitute a portion of the absorbent constitution.

Figure 16:
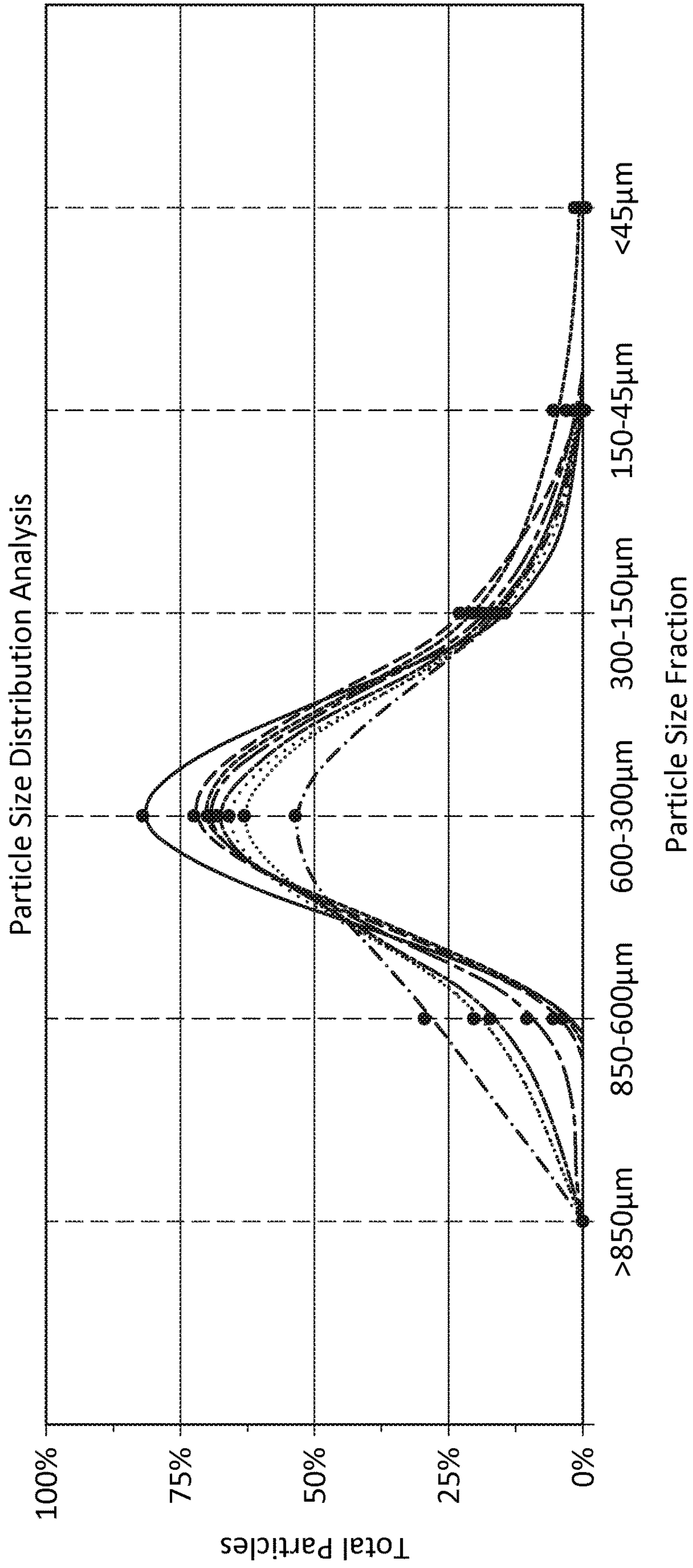
FIG. 16 is a graph showing particle size distribution of SAP.

As used herein "SAP particle size" may be measured in terms of particle size diameter. The SAP particles may be spherical or flake type (chunks). The particle size diameter may be determined by passing the SAP through a series of meshes/sieves having different size of openings. The weight of SAP that passes through each mesh may be determined to determine a particle size distribution for the entire mixture of SAP. Typical SAP may have a mixture of particles from around 80-micron diameter to 800-micron diameter. For example, FIG. 16 depicts a particle size distribution for a number of different super absorbents. The SAP disclosed herein may have a particle size ranging from 45 to 850 microns, or from 80 to 800 microns, or from 100 to 700 microns, or from 200 to 600 microns, or from 300 to 500 microns. The particle size of the SAP fines disclosed herein may vary depending upon the particular application. For example, fibrous constructions having denser bottom layers or surfaces will capture finer SAP particle sizes, in comparison to fibrous constructions having less dense bottom layers or surface which will allow finer SAP particle sizes to filter therethrough. In some aspects, the SAP fines include SAP particles of 150 microns or less, or 100 microns or less, or 80 microns or less or 45 microns or less.

As used herein, "bodyside" or "body side" refers to a surface and/or side that faces the body of a user when the absorbent core composite is worn by a user (e.g., when the absorbent core composite is incorporated into a diaper or other absorbent article that is worn by a user).

As used herein, "upstream" in reference to a process step refers to a step in a process that occurs temporally before another step. As used herein, "upstream" in reference to fluid flow within an absorbent core composite refers to a spatial and/or temporal position along a flow path of the fluid.

Some aspects relate to the deposition and filtering of SAP onto, into, and/or through a nonwoven, such as a bulky nonwoven. The disclosure of U.S. Patent 2015/0045756, the entirety of which is incorporated herein by reference, provides discussions relevant to such SAP deposition and filtering.

This Description, the Summary, the individual Figures or the claims should not be construed as limiting aspects and applications disclosed herein. Instead, each of these portions of the present disclosure reveal one or more structural or material feature that may be combined or incorporated with the basic construction described above to define a unique aspect or application. Furthermore, the basic construction may be applied to or incorporated with a variety of disposable absorbent articles, each of which being in accordance with an aspect of the disclosure. The same applies to the systems, apparatus, and methods of making the absorbent composite and the disposable absorbent article incorporating the composite. That is, systems, apparatus, and methods (including sub-systems and sub-processes applied to making or configuring a component) of making different absorbent composites, as described above, are also revealed herein, and provided in accordance with aspects and applications of the present disclosure.

Absorbent Cores with Enhanced Fit and Absorbency

The present disclosure relates generally to absorbent cores or absorbent core composites, disposable absorbent articles that incorporate the absorbent core or core composites, and systems, apparatus and methods of making such, and to other related products. Certain aspects may also be applicable to sanitary napkins, feminine hygiene products, and the like. Specifically, an absorbent structure of the present disclosure may be incorporated into or with a variety of disposable absorbent articles to provide the absorbent mechanism in the finished product. In one aspect, the absorbent structure is an absorbent core composite that employs a particularly effective absorbent constitution having desirable structural (wet and dry) integrity and performance characteristics.

In one preferred embodiment, the absorbent constitution utilizes a fibrous structure and, more preferably, absorbent particles retained in or by a network of fibers of the fibrous structure. In certain constructions, the core composites utilize super absorbent particles (SAP) as the primary absorbent material and, further, a fibrous construction to provide a structure to retain a SAP distribution and provide, together with the SAP distribution, an absorbent core section having wet and dry integrity. In alternative, advantageous applications, spaced-apart absorbent sections are provided that readily conform with or to a desired "as worn" configuration, presenting improved fluid management and body fit characteristics. Most preferably, the absorbent particles are superabsorbent particles and further, the superabsorbent particles are advantageously distributed in the z-direction in the fibrous structure.

In one exemplary construction, the fibrous construction or structure provides a relatively firm support structure exhibiting both dry and wet integrity. In this context, the absorbent section is deemed to have structural integrity and capable of maintaining form and constitution through manufacturing, packaging, wear, and then, absorption and retention of waste. Furthermore, as described below, the absorbent core composite maintains such firmness even while conforming with the user's anatomy, and flexing and bending about multiple pre-defined lines. The SAP particles provide the primary absorbent function, reducing the "wet" burden on the fibrous construction and helping to maintain its structural integrity between and during dry and wet states. Furthermore, in a preferred arrangement, the core composite is provided by multiple-spaced apart absorbent sections, which sections may be SAP-fibrous sections (e.g., SAP-bulky non-woven or crepe spunbond) or other absorbent constitutions. Each absorbent section has thickness in the z-direction, a lateral width, and a length in the longitudinal direction that may extend between the front and back waist regions. Gaps or channels between the sections provide or include fold lines (or pivot lines) about which the sections may pivot or rotate prior to or during use (preferably greater than 12.5 degrees of rotation toward one another). In certain aspects, forces resulting from fastening and locating the article and the core composite against or around the user's thighs and crotch cause the core composite to conform and take up a "W"-shape (or act to enhance or exaggerate the W-shape).

In these preferred arrangements, the folding lines and folding shape are pre-designed (or their location or alignment pre-located) and their folding response is enhanced by several structural features, including the inclusion of channels or gaps between the absorbent sections and the use of relatively firm, longitudinally-extending absorbent core sections. For example, the use of SAP particles distributed in the z-direction facilitates the use of a fibrous structure that is not burdened with the function of capturing and absorbing liquid, and thus, is able to maintain, more readily, its structural integrity and form. Additionally, the channels and fold lines are pre-located to conform with or align with the thighs and the crotch region. The core composite includes lateral or side wing sections that have a width of about 20%-35% of the total width of the core, so as to place the adjacent channel or fold line in alignment relative to the thighs and to help rotate the middle or adjacent absorbent sections upward toward the crotch (where a centrally located fold line pivots adjacent middle section in reverse direction to that of the wing sections and pushes the inboard sides upward against the crotch. The core composite may also be fixed, by bond lines and the like, along or proximate with the outside or first bond lines to ensure the W-shape or W-fold. Accordingly, the preferred core composite has two wing absorbent sections, two middle absorbent sections, and three channels or fold lines between the sections.

Some aspects relate to an absorbent composite. The absorbent composite includes a core composite having spaced-apart absorbent sections (e.g., of BNW), with gaps or channels positioned between adjacent sections. The BNW sections contain SAP, which may have a gradient distribution within the BNW. The BNW may have a density gradience, facilitating the formation of a SAP gradience. In some such aspects, the absorbent core has a W-shaped configuration. The gaps or channels provide fold lines about which the core can fold in on itself to enter the W-shaped configuration.

The core may include a first and second nonwoven sheet encasing the SAP-containing BNW. Adhesive beads may couple the first and second NW sheets between adjacent sections of the BNW, maintaining an undulating shape in the first, top NW sheet, and providing pivot points for folding of the core. Furthermore, such adhesive beads provide structural strength to the core. The first and second NWs may be connected using a grooved forming roller with air suction to shape top NW into undulations.

In some aspects, the absorbent core includes multiple absorbent core constructions, with the upper core construction formed of the encased SAP-containing BNW and the lower core construction including a pulp-SAP layer wrapped in a NW. The upper core construction may provide an undulating top surface to the absorbent core, and the lower core construction may provide a planar bottom to the absorbent core. In some aspects, the absorbent core has a gradient SAP distribution, with larger SAP particles in a gradient distribution within the upper core construction, and with SAP fines contained within the lower core construction (e.g., mixed with pulp).

Some aspects of the present disclosure include an absorbent core. The core includes a first absorbent core construction. The first absorbent core construction includes multiple spaced-apart sections of a fibrous construction having a fiber structure. A first nonwoven sheet is positioned above the fibrous construction. A second nonwoven sheet is positioned below the fibrous construction. The first nonwoven sheet is coupled with the second nonwoven sheet at locations between adjacent sections of the multiple spaced-apart sections of the fibrous construction. Absorbent material is disposed within the fiber structure, between the first and second nonwoven sheets. Some aspects of the present disclosure include a multilayer absorbent core that includes an upper absorbent construction including a bulky fiber structure containing SAP, and a lower absorbent construction including pulp or fluff and SAP fines.

Some aspects provide for a method of depositing SAP into a BNW. The method includes introducing SAP to a BNW in a forced airstream to apply SAP thereto and to filter SAP therethrough. In some aspects, the BNW does not include pulp or fluff (i.e., is pulpless and fluffless). SAP passes into and is captured by BNW fibers. The BNW filters the SAP particles from the airstream, and the SAP is distributed in the z-direction within the BNW. The method may include introducing adhesive from a bottom of the BNW, and forming a gradient deposition of adhesive in the BNW. This may be performed prior to SAP deposition to enhance capture of the SAP. The method may include heating the BNW prior to SAP deposition to tackify the BNW, bulkify the BNW, or combinations thereof. In some aspects, a heated SAP airstream provides the heat to tackify and/or bulkify the BNW. In certain aspects, adhesive particles may be contained within the airstream. In some aspects, the BNW is a multilayer BNW having a gradient density, and the SAP/adhesive gradient distributions are gradient in the x-, y-, and/or z-directions. The differing densities within the BNW may facilitate the formation of gradiences in the SAP/adhesive distributions. In some such aspects, a diverter valve, pulsing, a blind, or other such methods are used to vary the SAP application over time to create a y-gradient (MD) of the SAP within the BNW.

Some aspects relate to a method that includes encapsulating multiple SAP filled absorbent sections between two nonwoven sheets to form an absorbent core. In some such aspects, a pre-application of adhesive between a lower nonwoven and the absorbent sections is performed. Beaded adhesive may be applied coincident with fold lines of the absorbent core. The upper, cover layer of the two nonwoven sheets is mated with the lower of the two nonwoven sheets at positioned coincident with the fold lines. In some such aspects, a grooved form roller with air suction is used to conform the upper, cover layer of the two nonwoven sheets to a grooved surface thereof to form undulations therein, as well as to couple the upper and lower layers of the two nonwoven sheets.

Some aspects provide for a method that includes capturing SAP fines that have filtered through the BNW, and directing the captured SAP fines to the lower core construction. The captured SAP fines may be mixed into a fluff/air stream of a hammer mill used to form a pulp-SAP layer of the lower core construction.

Some aspects of the present disclosure include a method of capturing SAP within a fibrous construction. The method includes passing a forced airstream containing SAP through a fibrous construction. At least some of the SAP is deposited within the fibrous construction. The method includes filtering the SAP at least partially through the fibrous construction such that a gradient distribution of SAP particle sizes is formed within the fibrous construction.

Some aspects of the present disclosure include an absorbent article that includes an absorbent core in accordance with the present disclosure, and a chassis, including a backsheet and a topsheet. The absorbent core is positioned between the topsheet and the backsheet and is coupled with the backsheet at selected locations, and is not connected to the backsheet at other selected locations. Some aspects of the present disclosure include a disposable absorbent article that includes a chassis defining front and waist end regions and a crotch region therebetween. An absorbent core composite is supported by the chassis and positioned, at least partly, in the crotch region. The core composite includes a plurality of spaced-apart absorption sections having area dimensions in the x- and y-directions and thickness in the z-direction. Each absorption section has an absorbent constitution including a fibrous material.

Some aspects relate to a method that includes attaching an absorbent core to a chassis such that the core is pre-folded/bunched. Such attachment may pre-fold the core into a W-shaped configuration, and may form air channels between the chassis and the core.

Some aspects of the present disclosure include a method of making an absorbent core. The method includes conveying a fibrous construction, depositing SAP on the fibrous construction from a forced airstream, and filtering the SAP at least partially through the fibrous construction. The method then includes separating the fibrous construction into multiple, spaced-apart sections, and coupling a first nonwoven sheet below the sections of the fibrous construction. The method includes positioning a second nonwoven sheet above the sections of the fibrous construction, and coupling the second nonwoven sheet with the first nonwoven sheet at positions between adjacent, spaced-apart sections of the fibrous construction.

Some aspects of the present disclosure include an apparatus for introducing SAP into a fibrous construction. The apparatus includes a fibrous construction conveyer, a forced airstream generator positioned to flow a forced airstream through a fibrous construction on the fibrous construction conveyer, and a SAP source positioned to combine SAP with the forced airstream upstream of the fibrous construction conveyer.

Some aspects of the present disclosure include a roller for forming an undulated topsheet of an absorbent core. The roller includes a body, a roller surface, and grooves formed on the roller surface.

In one aspect of the disclosure, an absorbent core composite is provided with multiple spaced-apart absorbent sections and characterized by multiple, pre-located fold lines between absorbent sections. Further, alternate embodiments of the absorbent composite or the disposable absorbent article may include one or more of the following features: (1) a "W"-shape profile in a conformed, as-worn, configuration, or in a flat, pre-worn configuration (of the disposable absorbent article); (2) absorbent wing sections having a width equal to 20%-35% of total width (TW) of the core, and in further variations, 25-30% of the TW, or 30% TW+/−2.5%; (3) a core fixed along bond lines coincident with outboard fold lines of the core; (4) a bottom "surface" of the absorbent core composite (e.g., bottom NW) that is planar while the top or cover layer (bodyside) is undulating and traverses the top contour of the absorbent composites, including dropping to the bottom of each gap and enhancing the definition of the fold lines (preferably attaching to the bottom layer); (5) four absorbent sections interspaced by three fold lines; (6) three fold lines (and preferably two wing sections), including two fixed, outboard fold lines and a free central fold line connecting a pair of middle sections; (7) three fold lines, including a free central fold line mutually biasing a pair of middle sections upwardly; (8) spaced-apart absorbent sections, each composed of fibrous structure retaining a distribution of SAP particles; (9) spaced-apart absorbent sections, each including a structure retaining a distribution of SAP particles in the z-direction and/or other distributions and SAP constitutions as described herein; and (10) other features described below and/or depicted in one or more of FIGS. 1-20E or shown in Table 1.

The present disclosure also provides an absorbent core composite including an absorbent constitution where a distribution of SAP is retained. In one aspect, an absorbent constitution is employed featuring a fibrous structure retaining the SAP distribution. Applications of this concept may include one of the following structural features or some combination of these features (each of which is further defined below) in an absorbent constitution or absorbent section: (1) a fibrous structure retaining a SAP distribution in the z-direction; (2) different sizes of SAP positioned in different density zones of the fibrous construction; (3) the use of bulky non-woven or crepe spunbond as the fibrous construction; (4) fibrous structure characterized by varying SAP property(ies) based on expected position; (5) the use of an adhesive gradient in fibrous structure; (6) a SAP/adhesive gradient; (7) a multi-density layered BNW; (8) a pre-heated BBNW; (9) bi-component BNW fibers, including a core with a higher Mp and a shell with lower Mp, such that the shell softens prior to core, providing a tackifying surface for capturing SAP; (10) an activated bottom surface (e.g., with IR), to increase activation at the bottom/increase adhesive effect at the bottom; (11) a re-activated BNW (e.g., via heat, IR, hot SAP); and (12) a crepe spunbond.

Absorbent Article

Figure 3:
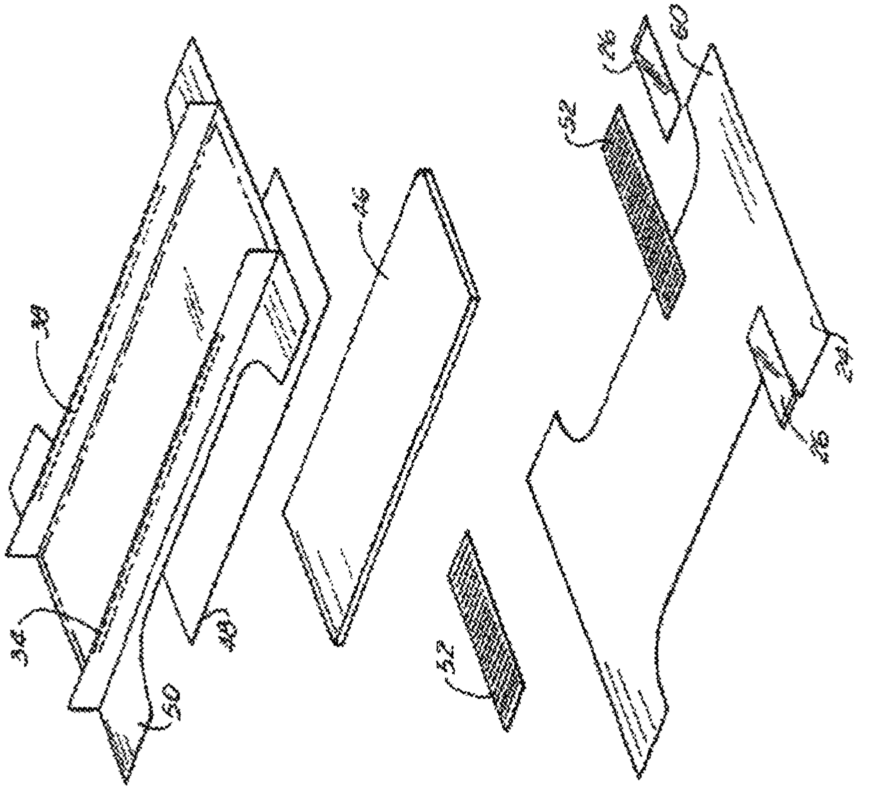
FIG. 3 is an exploded view of the disposable article of FIG. 1.
Figure 2:
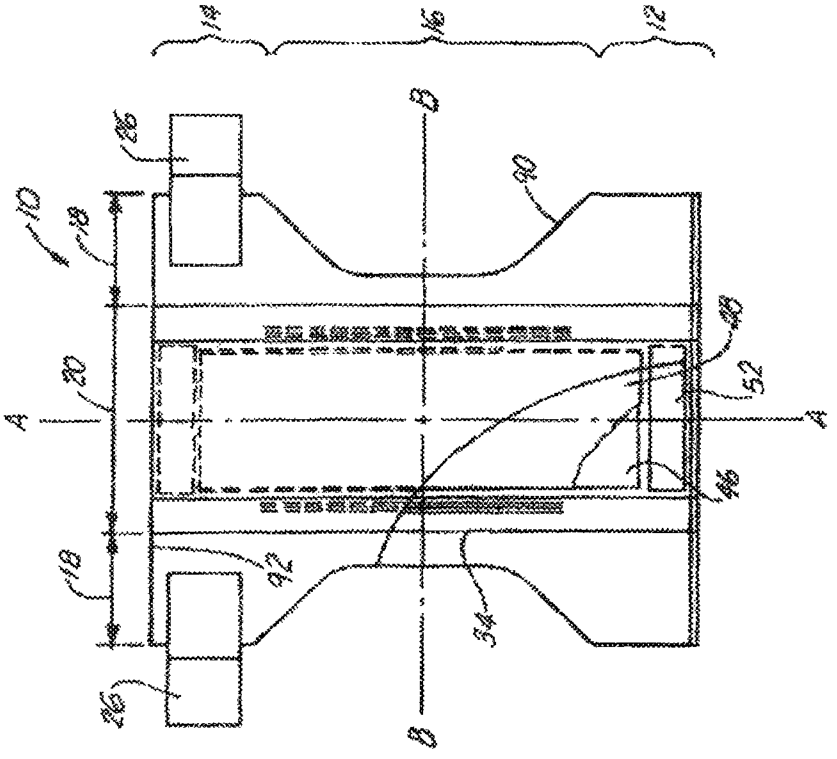
FIG. 2 is a top plan view of the disposable absorbent article of FIG. 1 in a flat and extended condition.

Concepts disclosed herein are applicable to an absorbent article such as the baby diaper 10 depicted in FIGS. 1-3, which diaper 10 incorporates an absorbent composite or absorbent core 46 to receive and store bodily waste. Diaper 10 includes a topsheet 50, a backsheet 60, and the absorbent core 46. Diaper 10 further includes upstanding barrier cuffs 34 which extend longitudinally along the diaper and are elasticized to conform to the buttocks of the wearer. Additionally, the diaper includes an elastic band 52 and fastening elements 26. Element 26, in use, extends to and engages the corresponding opposing end of the diaper to secure the diaper about the wearer. The web structure shown in FIG. 2 may be subsequently trimmed, folded, sealed, welded and/or otherwise manipulated to form a disposable diaper 10 in a finished or final form. To facilitate description of the diaper 10, the description refers to a longitudinally extending axis AA, a laterally extending central axis BB, a pair of longitudinally extending side edges 90, and a pair of end edges 92 which extend between side edges 90. Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening element 26 (e.g., a conventional tape fastener) is affixed to each of the ears 18 along the back-waist region 14 of diaper 10. When the diaper 10 is worn about the waist, the front waist region 12 is fitted adjacent the front waist area of the wearer, the back-waist region 14 is fitted adjacent the back-waist area, and the crotch region 16 fits about and underneath the crotch area. To properly secure the diaper 10 to the wearer, the ears 18 of the back-waist region 14 are brought around the waist of the wearer and toward the front and into alignment with the ears 18 of the front waist region 12. The securing surface may be located on or provided by the interior or exterior surface of the front waist region 12. Alternatively, the fastening elements 26 may be located on the ears 18 of the front waist region 12 and made securable to the ears 18 of the back-waist region 14. A suitable diaper structure typically employs at least three layers. These three layers include a backsheet 60, an absorbent core 46, and a topsheet 50. The diaper structure may or may not contain a pair of containment walls or leg cuffs 34 disposed upwardly from the topsheet 50 and preferably equipped at least with one or more spaced apart, longitudinally elastic members 38. It will be shown below that any of these diaper elements or a combination of these elements may be constructed with or using any of the absorbent core composites disclosed herein. Additionally, an acquisition layer 48 could be added to improve performance. Core 46 may be any of the absorbent cores disclosed herein.

Absorbent Core Composite

Figure 4A:
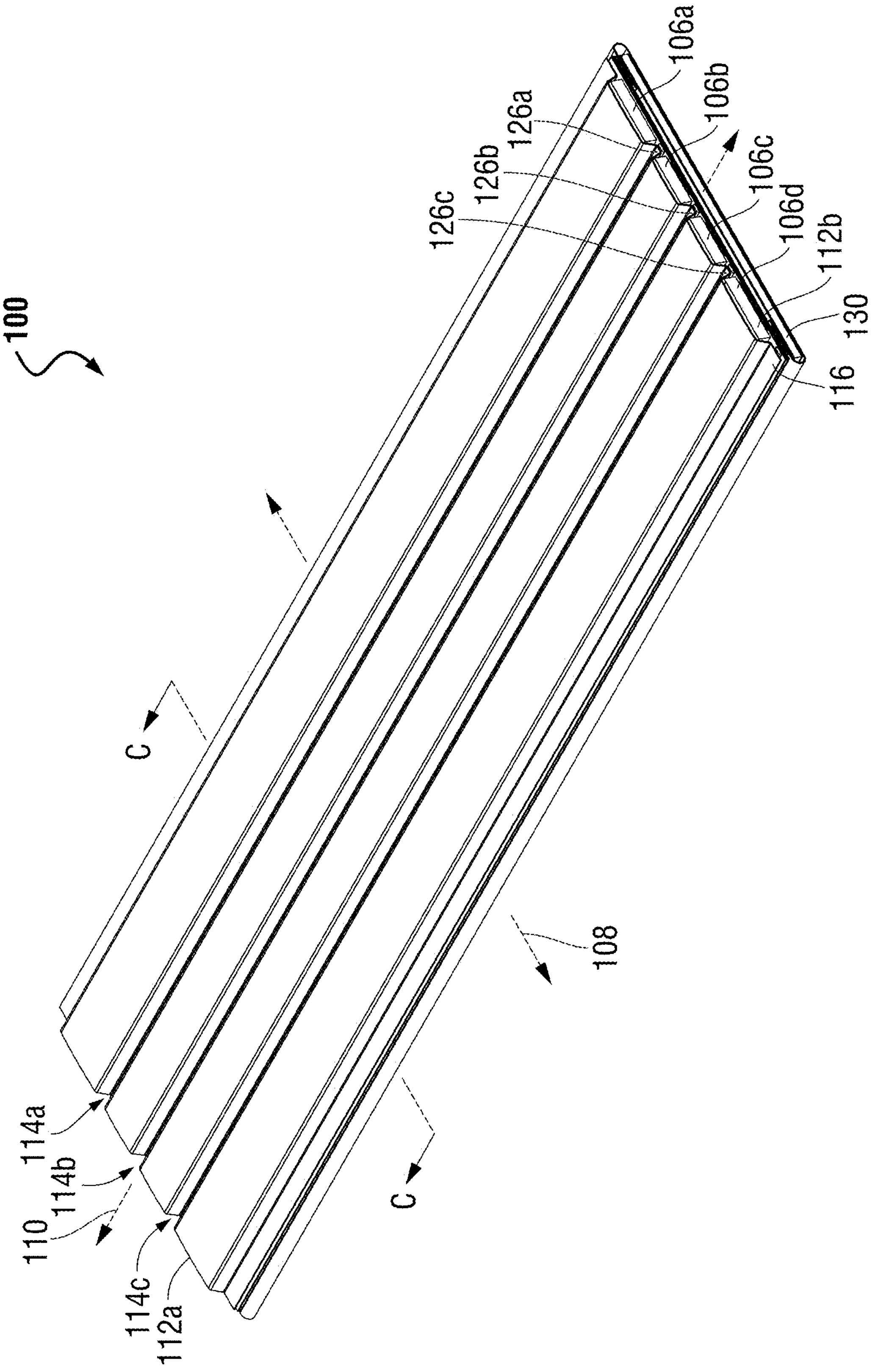
FIG. 4A is a perspective view of an absorbent core in a flat configuration.
Figure 5:
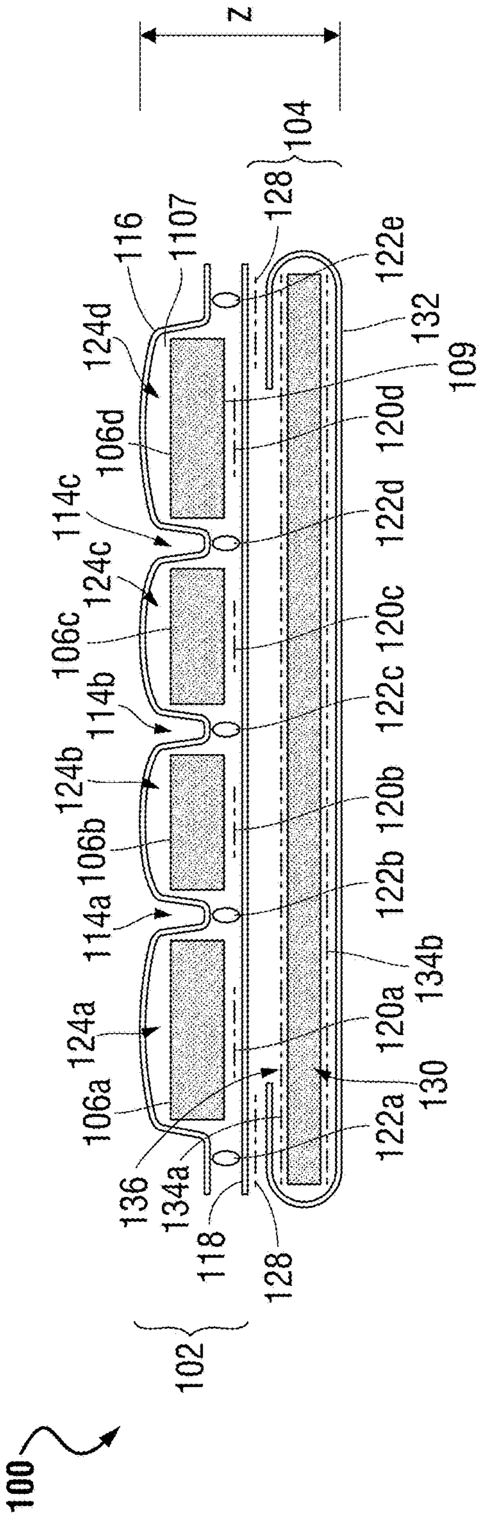
FIG. 5 is a lateral, cross-sectional view of an absorbent core.

FIG. 4A is a perspective view of an absorbent core composite 100 in a flat, extended configuration, i.e. prior to wear. FIG. 5 is a detailed, lateral cross-sectional view of the absorbent composite of FIG. 4A along line C-C. In one aspect of the disclosure, absorbent composite 100 is comprised of an upper absorbent layer or upper absorbent construction 102 as a primary, central core construction and a lower absorbent layer or lower absorbent construction 104 providing a secondary absorbent core construction. While shown as including upper and lower core components, absorbent core 100 may, in some applications, consist of only upper absorbent construction 102.

Absorbent Core Composite—Fibrous Construction

Upper absorbent construction 102 includes fibrous construction **106*a*-106*d*. In some aspects, fibrous construction 106*a*-106*d* preferably includes a nonwoven, specifically, a bulky nonwoven or a crepe spunbond. In some aspects, fibrous construction 106*a*-106*d*** is or includes air bonded nonwoven made using crimped bicomponent fibers of PET/PP (PP core with PET sheath) or PP/PE (PP core with a PE sheath).

As shown, upper absorbent construction 102 preferably includes four spaced apart sections of fibrous constructions **106*a*-106*d*. As further described below, a primary core composite divided into four spaced apart sections, including two outside wing sections that are of greater width than two middle sections, provides for a particularly advantageous absorbent construction. Upper absorbent construction 102 is not limited, however, to four separate, spaced apart sections of fibrous construction, and may include other numbers of fibrous constructions. For example, upper absorbent core 102 may include from two to ten separate, spaced apart sections of fibrous constructions. In some aspects, upper absorbent construction 102** does not include multiple separate, spaced apart sections of fibrous construction but, rather, includes only a single, continuous fibrous construction.

Each section of fibrous construction **106*a*-106*d* extends longitudinally along the length of absorbent core 100 between front and back waist regions. In some aspects, each section of fibrous construction 106*a*-106*d* extends, continuously, from a first longitudinal edge 112*a* to a second longitudinal edge 112*b* of absorbent core 100**.

Fibrous construction **106*a*-106*d* preferably includes and retains absorbent material (not shown), such as super absorbent polymer (SAP). The absorbent material may be contained within the fibrous structure of fibrous construction 106*a*-106*d* (e.g., via entanglement with the fibers thereof). In some aspects, the size, absorbent properties, and amount (e.g., weight and/or number of absorbent particles) may vary in the x-direction, y-direction, z-direction, or combinations thereof, as described in more detail below. In some aspects, each fibrous construction 106*a*-106*d*** is a bulky nonwoven impregnated with SAP.

Absorbent Core Composite—Channels

Positioned between adjacent sections of fibrous construction **106*a*-106*d* are gaps or channels 114*a*-114*c*. Channels 114*a*-114*c* may be separate, spaced channels, each positioned between two fibrous construction sections. While shown as including three separation channels, upper absorbent construction 102 is not limited to three separate, spaced apart channels, and may include other numbers of channels. For example, upper absorbent construction 102 may include from one to nine separate, spaced apart channels. In some aspects, upper absorbent construction 102 does not include any such channel, such as when upper absorbent construction 102** includes only a single, continuous fibrous section.

Channels **114*a*-114*c* are at least partially defined by a nonwoven sheet structure of upper absorbent construction 102. As shown in FIG. 5, upper absorbent construction 102 includes upper nonwoven sheet 116 and intermediate nonwoven sheet 118. While shown as including two separate nonwoven sheets, 116 and 118, upper absorbent construction 102 may include a different number of nonwoven sheets, such as a single nonwoven sheet that is wrapped or folded about fibrous constructions 106*a*-106*d* to be positioned both above fibrous construction 106*a*-106*d* (i.e., where upper nonwoven sheet 116 is shown) and below fibrous construction 106***a*-106*d* (i.e., where intermediate nonwoven sheet 118 is shown).

Channels 114*a*-114*c* may extend longitudinally, parallel with longitudinal centerline 110, along core 100. In some aspects, at least one of channels 114*a*-114*c* (e.g., channel 114*b*) extends coincident with longitudinal centerline 110. Channels 114*a*-114*c* may be or define absorbent free lines, strips, sections, or grooves in absorbent core 100 (i.e., channels 114*a*-114*c* may be generally void of absorbent material). In use, channels 114*a*-114*c* may function to promote fluid flow along longitudinal length (i.e., between edges 112*a* and 112*b*) of absorbent core 100, enhancing fluid distribution throughout absorbent core 100. Such enhanced longitudinal fluid flow may increase the utilization of absorbent core 100, as more portions of absorbent core 100 may be accessed by fluid, such as during a urination event. As such, channels 114*a*-114*c* may improve surface dryness of absorbent core 100 and/or surface dryness of an absorbent article containing absorbent core 100; thereby, reducing the likelihood of leakage and allowing absorbent core 100 to be used for longer periods of time.

In one exemplary aspect, a total lateral width of absorbent core 100 is 100 mm; a lateral width of each outer, laterally positioned fibrous sections 106*a* and 106*d* is 20 mm; a lateral width of each inner, centrally positioned fibrous sections 106*b* and 106*c* is 15 mm; and a lateral width of the space between each adjacent fibrous sections 106*a*-106*d* is about 5 mm or 6 mm. These dimensions are, of course, merely exemplary for one particular core, as the absorbent core and components thereof may have other dimensions. In some aspects, the total lateral width of absorbent core ranges from 60 to 130 mm, or from 70 to 110 mm or from 80 to 100 mm; the lateral width of each of the outer, laterally positioned fibrous sections ranges from 15 to 30 mm or form 18 to 25 mm or is about 20 mm; the lateral width of each inner, centrally positioned fibrous sections is from 7 to 20 mm or from 10 to 18 mm or from 13 to 16 mm or is about 15 mm; the lateral width of the space between each adjacent fibrous sections is from 2 to 10 mm or from 3 to 8 mm or form 4 to 7 mm or from 5 to 6 mm; or combinations thereof.

Fibrous sections 106*a*-106*d* may be coupled with lower intermediate nonwoven sheet 118. For example, fibrous sections 106*a*-106*d* may be adhered to intermediate nonwoven sheet 118 via adhesive 120*a*-120*d*. While fibrous sections 106*a*-106*d* is shown as adhered to intermediate nonwoven sheet 118, in some aspects fibrous sections 106*a*-106*d* is not adhered to intermediate nonwoven sheet 118. In some aspects, adhesive 120*a*-120*d* is or includes a hotmelt adhesive (HMA). In some aspects, a lateral width of each application of adhesive 120*a*-120*d* is less than (i.e., narrower than) the lateral width of the respective fibrous sections 106*a*-106*d*. Adhesive 120*a*-120*d*, such as HMA, may be applied by slot or spray application methods to the fibrous sections 106*a*-106*d*, intermediate nonwoven sheet 118, or both.

Upper nonwoven sheet 116 is positioned above fibrous sections 106*a*-106*d*, opposite intermediate nonwoven sheet 118. Upper nonwoven sheet 116 is coupled with intermediate nonwoven sheet 118. For example, upper nonwoven sheet 116 may be adhered to intermediate nonwoven sheet 118 via adhesive beads 122*a*-122*e*. Adhesive beads 122*a*-122*e* may be in the form of linear strips or tubes. Adhesive beads 122*a*-122*e* may extend, continuously or intermittently, from edge 112*a* to edge 112*b*. Adhesive beads 122*a*-122*e* may provide a seal between upper nonwoven sheet 116 and intermediate nonwoven sheet 118, encapsulating fibrous sections 106*a*-106*d* therein. In some aspects, each adhesive bead 122*a*-122*e* is in the form of a line or bead of hotmelt adhesive. Adhesive bead 122*a*-122*e* may have a basis weight of around 10 g/m (grams per linear meter), or from 8 to 12 g/m.

The spaces between upper nonwoven sheet 116, intermediate nonwoven sheet 118, and adhesive beads 122*a*-122*e* define tubes 124*a*-124*d* that extend longitudinally from edge 112*a* to edge 112*b*, parallel with longitudinal centerline 110. Fibrous sections 106*a*-106*d* are contained and maintained within separate, tubes 124*a*-124*d*, respectively. Adhesive beads 122*a*-122*e* may be sufficiently strong such that, upon insult, absorbent material contained within fibrous sections 106*a*-106*d* is maintained within the fibrous structures thereof, or at least within the respective tube 124*a*-124*d*.

Upper nonwoven sheet 116 is bonded with lower nonwoven sheet 118 at a position between lower nonwoven sheet 118 and the top surfaces 1107 of fibrous sections 106*a*-106*d*, such that upper nonwoven sheet 116 extends at least partially into the spaces between fibrous sections 106*a*-106*d*, contouring thereabout, to bond with intermediate nonwoven sheet 118. Such contouring of upper nonwoven sheet 116 about and between fibrous sections 106*a*-106*d* at least partially defines channels 114*a*-114*c*. In some aspects, upper nonwoven sheet 116 provides an undulating, upper surface to absorbent core 100. In some aspects, intermediate nonwoven sheet 118 provides a flat lower surface to upper absorbent construction 102. While upper nonwoven sheet 116 may be undulating and intermediate nonwoven sheet 118 may be flat, upper nonwoven sheet 116 and intermediate nonwoven sheet 118 may have the same footprint. That is, intermediate nonwoven sheet 118 may be generally flat and upper nonwoven sheet 116 may be generally undulating such that upper nonwoven sheet 116 has a surface area, defined over a lateral extend of core 100, that is at least 120%, or at least 130%, or at least 140%, or at least 150%, or at least 175%, or is from 120% to 175%, or from 130% to 150% of the surface area of intermediate nonwoven sheet 118 over the same lateral extent of core 100.

Absorbent Core Composite—Fold Lines

In some aspects, such contouring of upper nonwoven sheet 116 about and between fibrous sections 106*a*-106*d*, in conjunction with adhesive beads 122*a*-122*e* and channels 114*a*-114*c*, at least partially defines fold lines of absorbent core 100. Fold lines 126*a*-126*c*, as shown in FIG. 4A, may be coincident with channels 114*a*-114*c*. Fold lines 126*a*-126*c* facilitate the folding of absorbent core 100 from the flat configuration, as shown in FIG. 4A, to a folded and/or bunched configuration (e.g., a W-shaped configuration) as shown and described in more detain below with references to FIGS. 8-9D. In some aspects, each fold line 126*a*-126*c* extends parallel with the longitudinal centerline 110 of core 100. In some aspects, at least one of fold lines 126*a*-126*c* (e.g., fold line 126*b*) is coincident with longitudinal centerline 110 of core 100.

While described as "folding", as used herein a "fold" does not require 180% pivots of fibrous sections 106*a*-106*d* about fold lines 126*a*-126*c*, nor does "fold" require that adjacent fibrous sections 106*a*-106*d* folding towards each other must make contact. Rather, as used herein, to "fold" includes pivoting adjacent sections of fibrous construction 106*a*-106*d* to reduce the angle between the two adjacent sections. For example, when core 100 is in a flat configuration, as shown in FIG. 4A, adjacent sections of fibrous construction 106*a*-106*d* are at straight angles (i.e., 180°) relative to one another. When in the folded or bunched configuration (e.g., W-shaped), adjacent sections of fibrous construction 106*a*-

106*d* are at angles that are less than 180°) relative to one another, but greater than 0°, or from 160° to 20°, or from 140° to 40°, or from 120° to 60°, or from 100° to 80°.

Upper nonwoven sheet 116 and lower nonwoven sheet 118 may function to contain fibrous sections 106*a*-106*d* therebetween, enclosing fibrous sections 106*a*-106*d* and facilitating the prevention of migration of super absorbent particles (or other absorbent material) out of the respective nonwoven or tube 124*a*-124*d* within which it is contained. Upper nonwoven sheet 116 and lower nonwoven sheet 118 may be any nonwoven disclosed herein or known to those skilled in the art including, but not limited to, spunbond-meltblown-spunbond (SMS) nonwovens and spunbond nonwovens made from synthetic or natural fibers.

Absorbent Core Composite—Pulp Layer

Absorbent core 100 includes lower absorbent construction 104, which is positioned below and adjacent upper absorbent construction 102. Lower absorbent construction 104 is coupled with upper absorbent construction 102. In some aspects, lower absorbent construction 104 is adhered with upper absorbent construction 102, such as via adhesive 128. Adhesive 128 may be, for example, a hot melt adhesive.

Lower absorbent construction 104 may be or include a lower fibrous construction 130, which may be a fluff and/or pulp fibrous absorbent construction that provides additional absorbent capacity to absorbent core 100. In some aspects, lower fibrous construction 130 includes synthetic fibers, natural fibers, or combinations thereof. For example, lower fibrous construction 130 may be or include an agglomeration and/or network of pulp-based fibers, such as cellulose fibers including, but not limited to, micro-fibrillated cellulose (MFC) fibers, nano-fibrillated cellulose (NFC) fibers, or combinations thereof. Lower fibrous construction 130 may include cellulose fibers, such as fluff pulp formed via a conventional fluff pulp core forming process. Alternatively, the cellulose fibers of lower fibrous construction 130 may be formed via an airlaid web. Lower fibrous construction 130 may include synthetic fibers, which may be formed as an airthrough bonded web, such as an airthrough bonded web of polyethylene-terephthalate/polyethylene/polypropylene (PET/PE/PP) fibers. In other aspects, lower fibrous construction 130 includes a foam, bulky nonwoven, air through nonwoven, pulp, absorbent material, or any combination thereof.

In some aspects, lower fibrous construction 130 includes absorbent material (not shown), such as SAP, intermixed with the pulp-based fibers thereof. In certain aspects, there is a gradient distribution of absorbent material particles (e.g., SAP particles) throughout absorbent core 100. For example, relatively larger absorbent material particles may be contained with fibrous sections 106*a*-106*d*, with relatively smaller absorbent material particles contained within lower fibrous construction 130. As described in more detail elsewhere herein, fibrous sections 106*a*-106*d* may include a gradient distribution of absorbent material particles in the z-direction, such that relatively larger absorbent material particles are distributed at or in closer proximity to top surface 1107 of fibrous sections 106*a*-106*d*, while relatively small absorbent material particles are distributed at or in closer proximity to bottom surface 109 of fibrous sections 106*a*-106*d*. Lower fibrous construction 130 may include absorbent material particles that are smaller than those that are distributed at or in closer proximity to bottom surface 109 of fibrous sections 106*a*-106*d*. For example, lower fibrous construction 130 may contain absorbent material particle "fines", while fibrous sections 106*a*-106*d* contains absorbent material particles that are larger than "fines". In some aspects, fibrous sections 106*a*-106*d* does not have a gradient distribution of absorbent material particles in the z-direction.

In some aspects, the basis weight of lower fibrous construction 130 (e.g., of cellulose pulp fibers) is relatively low, such as about 40 gsm. Lower fibrous construction 130 is not limited to such a basis weight, and may have a lower or higher basis weight. However, in some aspects it is preferred to minimize the basis weight of lower fibrous construction 130, such as to reduce cost.

Lower absorbent construction 104 includes one or more nonwoven sheets disposed on at least one side thereof. As shown in FIG. 5, lower absorbent construction 104 includes nonwoven sheet 132, which is positioned about lower fibrous construction 130 in a C-wrap configuration. Nonwoven sheet 132 may be or include any of the nonwovens disclosed herein including, but not limited to, SMS nonwoven, spunbond nonwoven, or tissue.

Nonwoven sheet 132 is coupled to lower fibrous construction 130. For example, nonwoven sheet 132 may be adhered to lower fibrous construction 130 via adhesive 134*a* and 134*b*, which may be an application of hotmelt adhesive on the upper and/or lower surfaces of lower absorbent construction 130 (as shown). Adhesive 134*b*, positioned on the bottom surface of lower fibrous construction 130, may function to attach nonwoven sheet 132 to lower fibrous construction 130. Adhesive 134*b* may be a hotmelt adhesive applied via any method commonly used in the manufacture of absorbent articles and composites, including spray coating, slot coating, or control coat methods. Adhesive 134*a*, positioned on the top surface of lower fibrous construction 130, may function to bond lower absorbent construction 104 to upper absorbent construction 102, such as to intermediate nonwoven sheet 118. Adhesive 134*a* may also function to increase the dry integrity and wet integrity of lower absorbent construction 104, by retaining the fibers and/or absorbent material thereof in place during manufacture, transport, and/or use. Adhesive 134*a* and 134*b* may be may be any suitable formulation of hotmelt adhesive including, but not limited to, construction adhesives and core integrity adhesives depending on the specific function(s) that the adhesive is intended to serve.

With nonwoven sheet 132 positioned about lower fibrous construction 130 in a C-wrap configuration, opening 136 is provided for receipt of fluid flow from upper absorbent construction 102 into lower absorbent construction 104. In other aspects, nonwoven sheet 132 is disposed on only one side of lower fibrous construction 130. In still other aspects, nonwoven sheet 132 completely encloses lower fibrous construction 130 on all sides thereof. While shown as including a single nonwoven sheet 132, lower absorbent construction 104 may include multiple nonwoven sheets or webs that are disposed on and/or about lower fibrous construction 130 to completely or partially enclose lower fibrous construction 130. Nonwoven sheet 132 may function to enclose the fibers, absorbent material, or combinations thereof of lower absorbent construction 130; thereby, ensuring the structural and positional integrity (dry and wet integrity) of lower fibrous construction 130 during manufacture, transport and use of absorbent core 100.

In some aspects, lower fibrous construction 130 (also referred to as a pulp layer) is a relatively low basis weight pulp layer positioned on the bottom side of core 100. Lower fibrous construction 130 may provide a soft feeling against the outer cover for users. Lower fibrous construction 130 may also provide at least some absorbency and wicking properties to core 100. Lower fibrous construction 130 may increase wicking of fluid towards the front and rear ends of core 100, and provide a temporary reservoir for any fluid that is not absorbed by the SAP. In some aspects, lower fibrous construction 130 is combined with or replaced with an airlaid nonwoven (e.g., a cellulose airlaid nonwoven). In some aspects, lower fibrous construction 130 provides a structural layer positioned beneath fibrous sections 106*a*-106*d*.

Figure 4B:
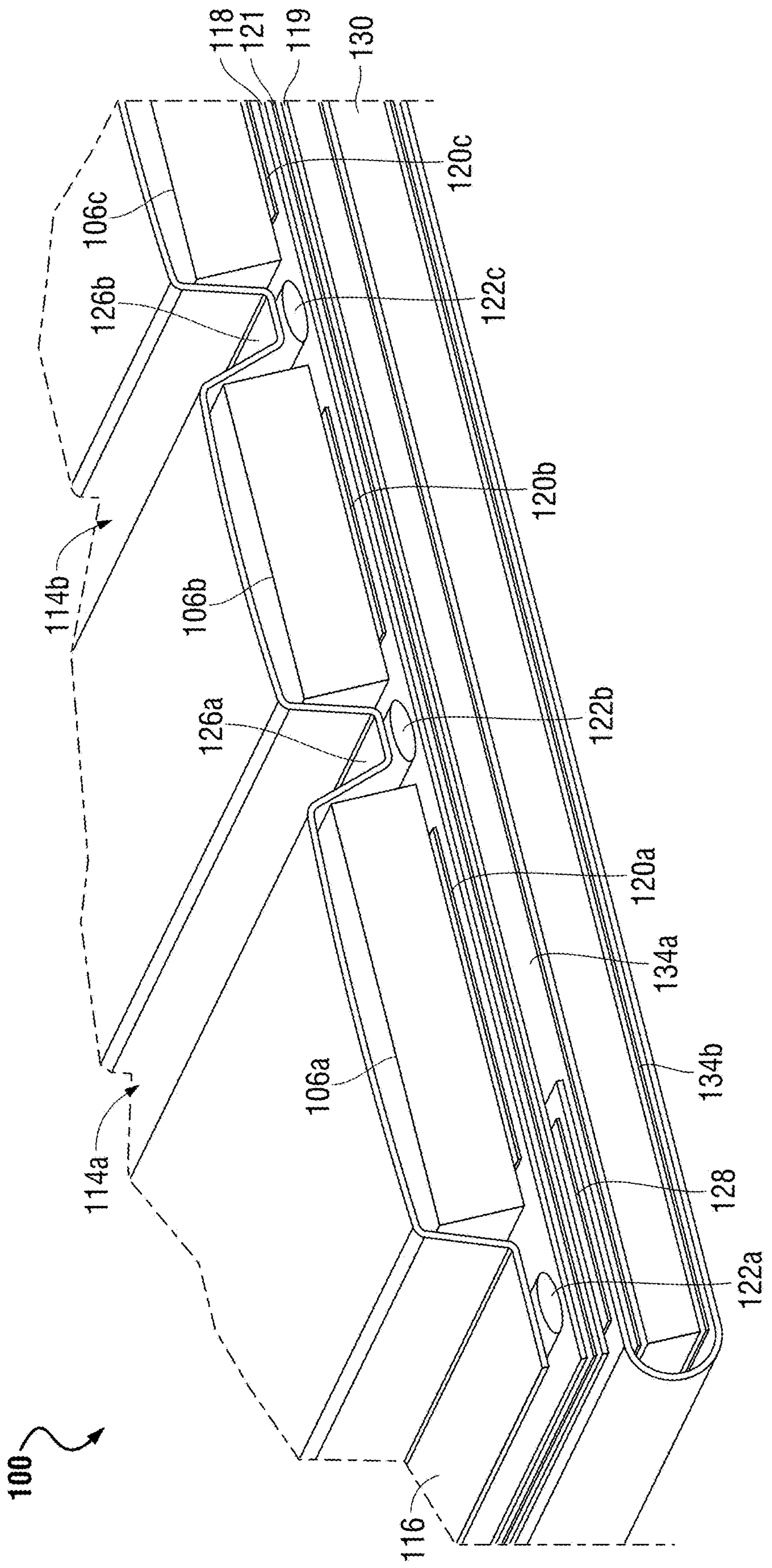
FIG. 4B is a detailed view of the core of FIG. 4B.

FIG. 4B is a detailed view of FIG. 4A, showing the layers thereof. In some aspects, as shown in FIG. 4B, an additional intermediate nonwoven layer 119 may be provided between intermediate nonwoven sheet 118 and nonwoven sheet 132. Additional intermediate nonwoven layer 119 may be adhered with intermediate nonwoven sheet 118, such as via adhesive 121. Additional intermediate nonwoven layer 119 may form a part of the upper absorbent construction, form a part of the lower absorbent construction, or may be separate structure positioned between the upper and lower absorbent constructions.

Absorbent Article with Absorbent Core

Figure 6:
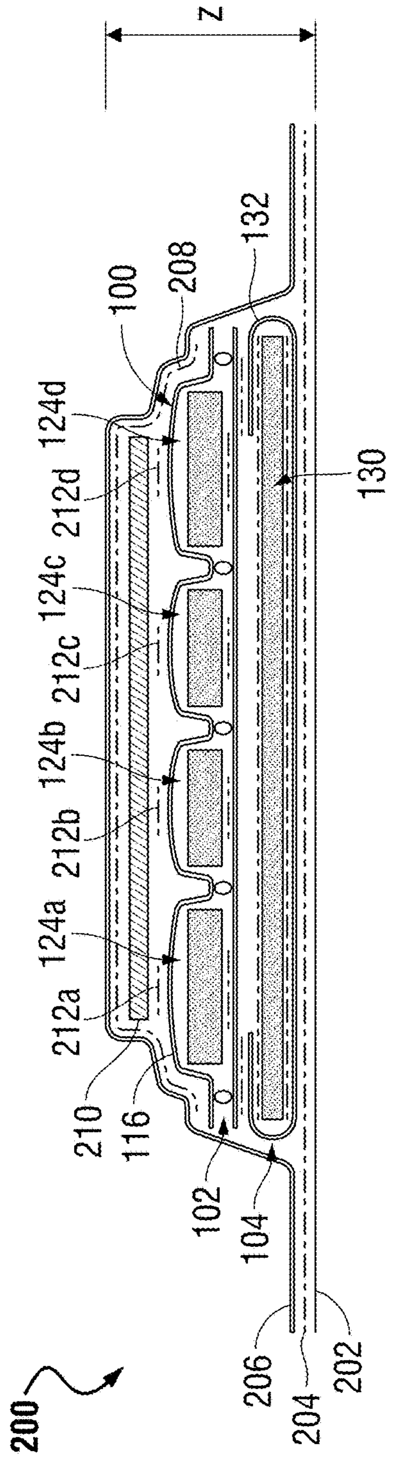
FIG. 6 is a lateral, cross-sectional view of an absorbent article including an absorbent core.
Figure 7:
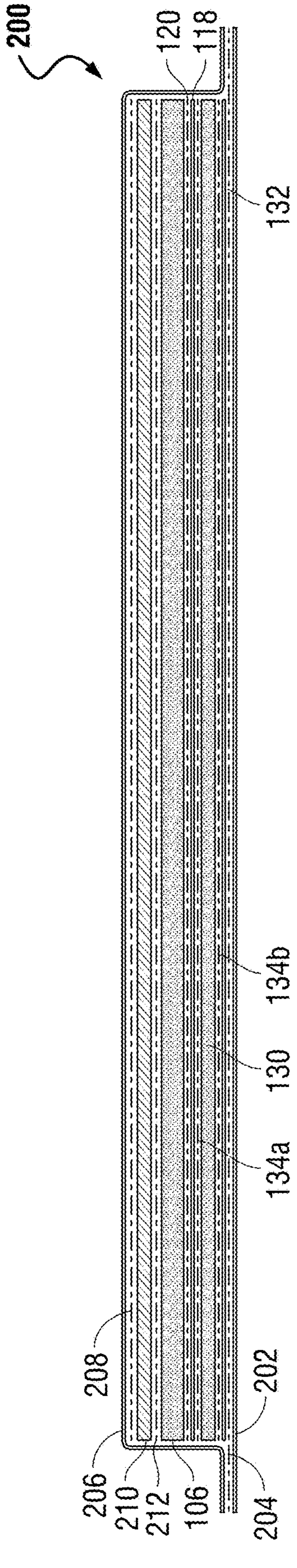
FIG. 7 is a longitudinal, cross-sectional view of an absorbent article including an absorbent core.

FIGS. 6 and 7 depict an absorbent core the same or substantially similar to that of FIG. 5, but incorporated into an absorbent article, such as a diaper. In some aspects, a structural layer or construction (e.g. a chassis or portions thereof) is positioned beneath core 100. The structural layer may be fixed at the lateral margins of 100. Absorbent article 200 includes backsheet 202, which may be a liquid impermeable sheet. Backsheet 202 is coupled with the lower surface of absorbent core 100. As shown, backsheet 202 is coupled (e.g., adhered) to nonwoven sheet 132 of lower absorbent construction 104. However, when absorbent core 100 does not include lower absorbent construction 104, backsheet 202 may be coupled (e.g., adhered) to intermediate nonwoven sheet 118 of upper absorbent construction 102. Backsheet 202 is adhered to nonwoven sheet 132 via adhesive 204, which may be a hotmelt adhesive. Backsheet 202 may be any backsheet for use in absorbent articles known to those skilled in the art.

Absorbent article 200 includes toposheet 206, which may be a liquid permeable sheet. Topsheet 206 is coupled with upper absorbent construction 102 of absorbent core 100. As shown, topsheet 206 is adhered to upper absorbent construction 102 via adhesive 208. Adhesive 208, which may be a hotmelt adhesive, adheres topsheet 206 with a portion of upper nonwoven sheet 116. Topsheet 206 may be any topsheet for use in absorbent articles known to those skilled in the art.

Absorbent article 200 includes acquisition distribution layer, ADL 210, positioned between topsheet 206 and absorbent core 100. ADL 210 may function to receive insult from topsheet 206 and distributed insult into absorbent core 100. ADL 210 may be any acquisition distribution layer known to those skilled in the art. ADL 210 may be adhered to topsheet 206 via a portion of adhesive 208. ADL 210 may also be coupled with (e.g., adhered to) absorbent core 100 via adhesives 212*a*-212*d* (e.g., hotmelt adhesive). For example, adhesives 212*a*-212*d* may be positioned on top of upper nonwoven sheet 116 above tubes 124*a*-124*d*, respectively, to bond with ADL 210. While shown as including ADL 210, the absorbent articles disclosed herein are not limited to including an acquisition distribution layer.

A portion of topsheet 206 may also be adhered to backsheet 202, such as via a portion of adhesive 204. As such, topsheet 206 and backsheet 202 enclose absorbent core 100, such that absorbent core 100 is contained within (e.g., sandwiched between) topsheet 206 and backsheet 202.

W-Shaped Absorbent Core

Figure 8:
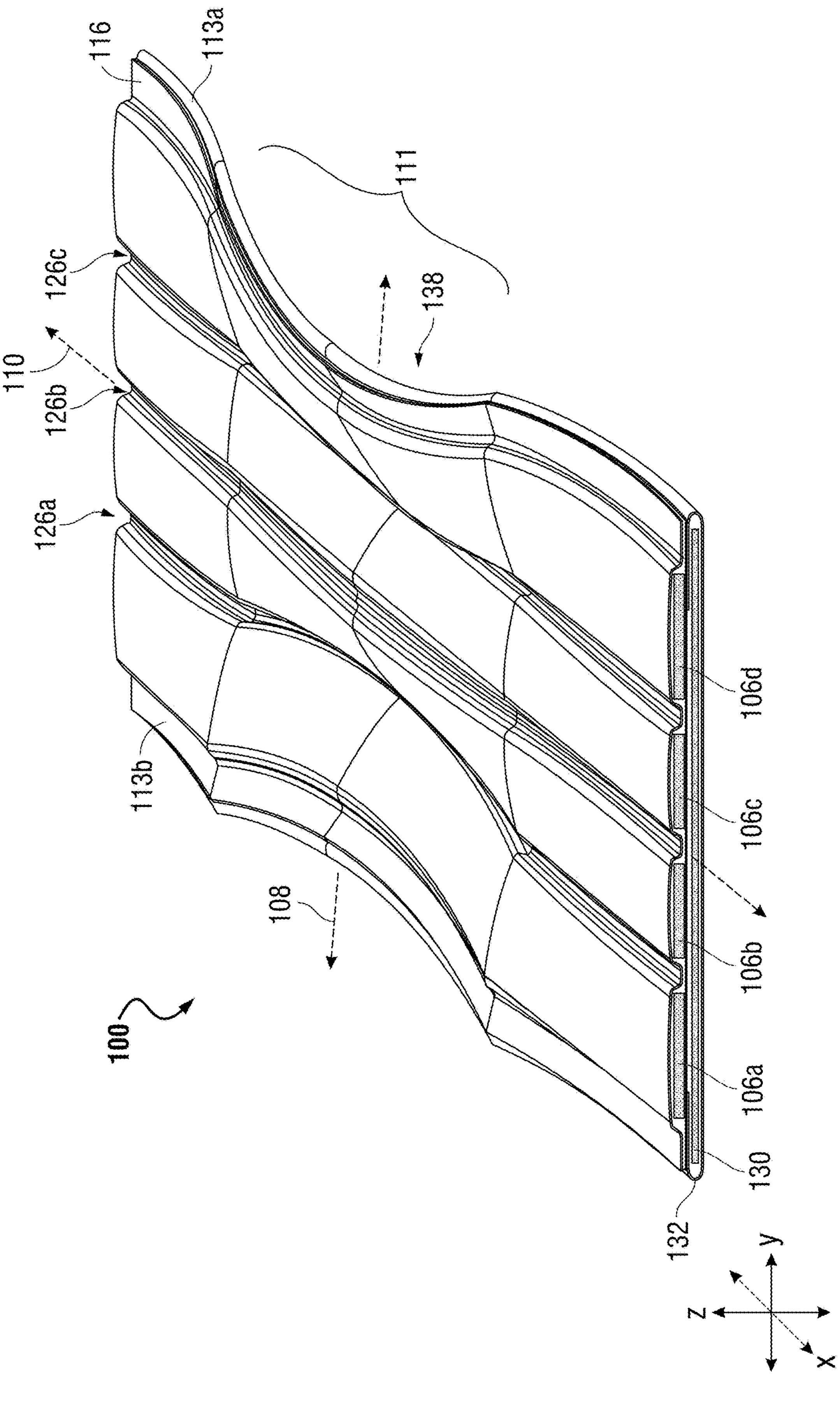
FIG. 8 is a perspective view of a core in a W-shaped configuration.

In some aspects, the present disclosure includes an absorbent core composite having spaced-apart, mutually-pivotable absorbent sections. With reference to FIG. 8, one such exemplary absorbent core 100 is depicted. Absorbent core 100 of FIG. 8 may be the same or substantially the same as absorbent core 100 shown in FIG. 4A, with the exception that in FIG. 8 absorbent core 100 is shown in a pivoted or bunched configuration; whereas, in FIG. 4A absorbent core 100 is shown in a flat configuration. The flat configuration of absorbent core 100, as shown in FIG. 4A, may be the configuration of absorbent core 100 during manufacture of absorbent articles, during packaging and transport of absorbent core 100, and/or at any time prior to use of absorbent core 100.

When absorbent core 100, incorporated within an absorbent article, is worn by a user, forces imparted onto absorbent core 100 from the user's body may cause a bunching and/or folding of absorbent core 100. Fold lines 126*a*-126*c* positioned between the adjacent, spaced-apart, mutually-pivotable absorbent sections (fibrous sections 106*a*-106*d*) of absorbent core 100 provide for or promote a controlled bunching of absorbent core 100. Fold lines 126*a*-126*c* define pivoting lines about which sections of fibrous sections 106*a*-106*d* pivot during folding of absorbent core 100 into a W-shaped or other accordioned configuration. For example, with absorbent core 100 positioned between a user's thighs, the user's thighs may exert forces upon absorbent core 100 that have a force component that is directed parallel to the lateral centerline 108 of absorbent core 100, a force component that is directed in the z-direction, or combinations thereof. Such forces may result in a folding and/or bunching of absorbent core 100 about and along fold lines 126*a*-126*c*, particularly in the central crotch region 111 of absorbent core 100. Such bunching and/or folding of absorbent core 100 may be confined to or at least concentrated at the central crotch region 111, such that lateral edges 113*a* and 113*b* of core 100 are provided with curved segments 138 in the central crotch region 111. As such, when worn, absorbent core 100 may have an hour-glass configuration or a substantially hour-glass configuration as a result of folding and/or bunching, rather than as a result of cutting. As core 100 adopts a W-shaped configuration when worn between a user's legs, core 100 is laterally narrowed in the central crotch region 111 between the legs, similar to a core that has been cut into an hourglass shape. However, core 100 does not exhibit a loss of absorbency as a result of the hourglass shape that would result from cutting the core, removing absorbent material therefrom, to achieve the hourglass shape.

Such bunching and/or folding of absorbent core 100 may provide absorbent core 100 with an accordion-shaped configuration. In some such aspects, such bunching and/or folding of absorbent core 100 may provide absorbent core 100 with a W-shaped configuration or substantially a W-shaped configuration, as is shown in FIGS. 8-9H. The particular shape into which core 100 is encouraged when worn may vary depending on, for example, the number of fold lines 126, the spacing between fold lines 126, the lateral width of fold lines 126, the spacing between fibrous sections 106, the lateral width of the fibrous sections 106, and the number of fibrous sections 106. Absorbent core 100 is not limited to folding into a W-shaped configuration, and may fold and/or bunch into other accordioned shapes.

Figure 9A:
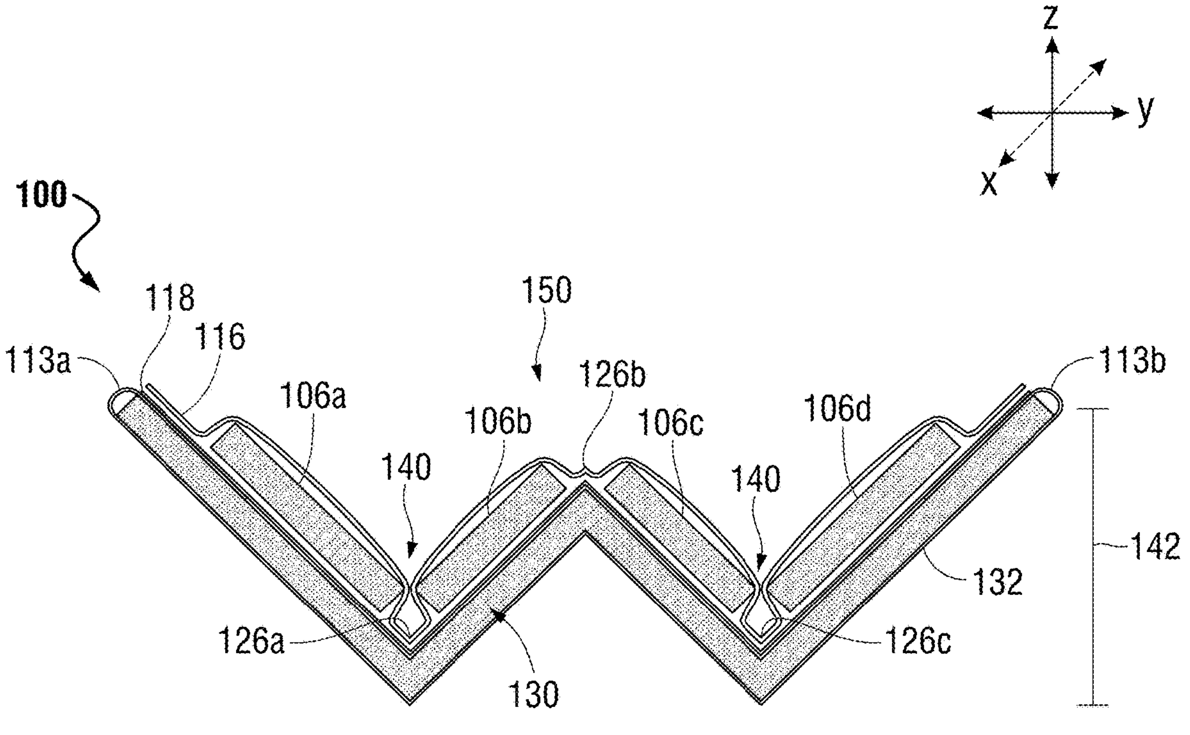
FIG. 9A is a cross-sectional view of a W-shaped core in the central crotch region.

With reference to FIGS. 8 and 9A, when absorbent core 100 is forced into the W-shaped configuration, the forces exerted onto core 100 result in moments about the fold lines 126*a*-126*c*, such that adjacent fibrous sections 106 pivot about the fold line 126 therebetween, encouraging core 100 upwards in the z-direction at fold line 126*b* and at edges 113*a* and 113*b* and encouraging core 100 to fold in upon itself about the fold lines 126. When in the W-shaped configuration, fold lines 126*a* and 126*c* are positioned closer to one another in the y-direction, in comparison to the relative positions of fold lines 126*a* and 126*c* when core 100 is in a flat configuration (as shown in FIG. 4A). Also, when in the W-shaped configuration, edges 113*a* and 113*b* are positioned closer to one another in the y-direction, in comparison to the relative positions of edges 113*a* and 113*b* when core 100 is in a flat configuration (as shown in FIG. 4A). Furthermore, fold line 126*b* and edges 113*a* and 113*b* are raised relative to the position of fold lines 126*a* and 126*c*, in the z-direction. As shown, edges 113*a* and 113*b* are positioned at a raised height 142 above fold lines 126*a* and 126*c*. In the W-shaped configuration, core 100 includes or valleys 140 defined between peak 150 and raised lateral edges 113*a* and 113*b*. With edges 113*a* and 113*b* at raised height 142, to flow outside of the core 100 the fluids contained within valleys 140 must flow upwards, against gravitational forces. As such, raised lateral edges 113*a* and 113*b* reduce or eliminate the occurrence of fluid leakage (or other leakage) from core 100. Thus, W-shaped core 100 reduces side-ways, lateral flow of fluid towards lateral edges 113*a* and 113*b* of core 100; thereby, reducing the likelihood of the absorbent product leaking from the lateral edges thereof.

Figure 9B:
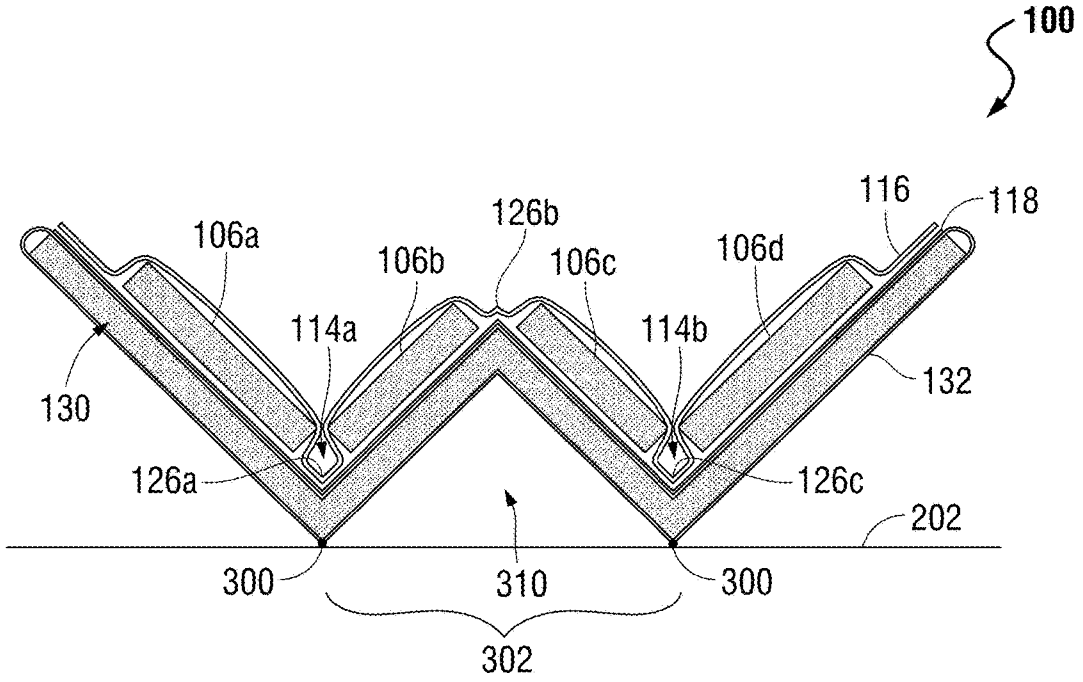
FIG. 9B is a cross-sectional view of a W-shaped core in the central crotch region attached with a backsheet of a chassis.

With reference to FIG. 9B, absorbent core 100 is shown coupled with back sheet 202. Absorbent core 100 is adhered or otherwise coupled with backsheet 202 at attachment sites 300 (e.g., adhesive lines or sites). Attachment sites 300 are positioned below fold lines 126*a* and 126*c*. The lateral distance 302 between attachment sites 300 is less than the lateral distance between fold lines 126*a* and 126*c* when core 100 is in a flat configuration (e.g., as shown in FIG. 4A). As such, upon coupling of core 100 with backsheet 202 via attachment sites 300, fold lines 126*a* and 126*c* are forced closer to one another in the y-direction (lateral direction) than when core 100 is in the flat configuration, such that core 100 is at least partially pre-folded into the W-shaped configuration via attachment of core 100 to backsheet 202.

As is evident from FIG. 9B, in some aspects folding of core 100 into a W-shaped configuration results in the formation of channel 310 positioned between core 100 and backsheet 202. Channel 310 may function as an airflow channel between core 100 and backsheet 202, facilitating drying of core 100 and making the absorbent article more comfortable to wear. FIG. 9C shows an exemplary expected relative positional arrangement of backsheet 202 and core 100, as well as exemplary expected relative positional arrangement of fibrous sections 106*a*-106*d* of core 100, when an absorbent article including the core 100 is worn by a user, with forces exerted thereon from the user's thighs. As shown, backsheet 202 is encouraged upwards, along the z-direction, by forces excreted thereon from the user's thighs. Such forces are also transferred to core 100, promoting the folding of core 100 into the W-shaped configuration, as shown, with fibrous sections 106*a*-106*d* pivoting about fold lines 126*a*-126*c* and raising edges 113*a* and 113*b* of core 100 to raised height 142 above backsheet 202.

In some aspects, as shown in FIG. 9C, core 100 is not adhered or otherwise coupled with backsheet 202 at edges 113*a* and 113*b*, at any point between edge 113*a* and fold line 126*a*, or at any point between edge 113*b* and fold line 126*c*. As such, fibrous sections 106*a* and 106*d* and edges 113*a* and 113*b* are free to move relative to and raise above backsheet 202. Movement of fibrous sections 106*a* and 106*d* and edges 113*a* and 113*b* is still restrained by attachment of core 100 with backsheet 202 at attachment sites 300. Similarly, in some aspects core 100 is not adhered or otherwise coupled with backsheet 202 at between attachment sites 300, such that fibrous sections 106*b* and 106*c* are free to move relative to and raise above backsheet 202 to form channel 310. Movement of fibrous sections 106*b* and 106*c* is still restrained by attachment of core 100 with backsheet 202 at attachment sites 300.

Figure 9D:
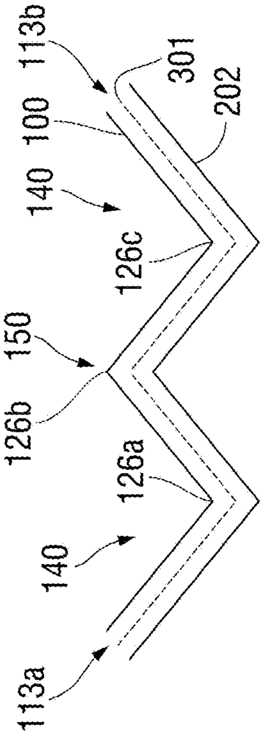
FIG. 9D is a cross sectional view of a W-shaped core in the central crotch region continuously attached with a backsheet of a chassis.

FIG. 9D depicts another embodiment of core 100 coupled with backsheet 202 in a W-shaped configuration. In FIG. 9D, core 100 is continuously or substantially continuously attached with backsheet 202, such as via adhesive 301. As such, when a portion of core 100 is forced into the W-shaped configuration, the portion of backsheet 202 that is attached to that portion of core 100 is also forced into the W-shaped configuration, as shown. With the backsheet 202 continuously or substantially continuously attached to core 100, channel 310 (FIG. 9C) is not formed therebetween. Also, while edges 113*a* and 113*b* cannot rise above backsheet 202 to a raised height due to adherence thereto, edges 113*a* and 113*b*, when in the W-shaped configuration, are still at a raised height relative to fold lines 126*a* and 126*c*.

Figure 9F:
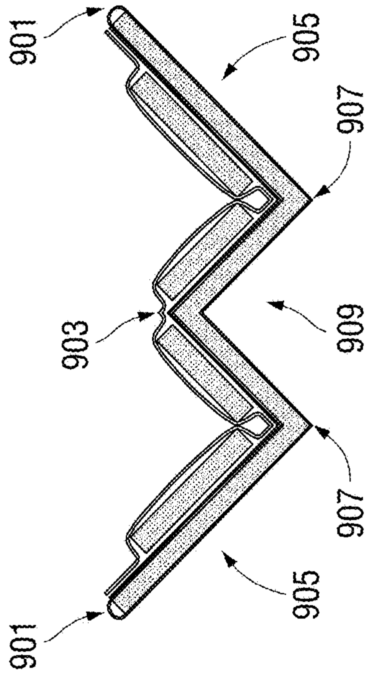
FIG. 9F is a cross sectional view of a W-shaped core in the central crotch region, showing the unfixed, raised edges; wing sections; fixed fold lines; unfixed, raised center fold line; and air channel.
Figure 9C:
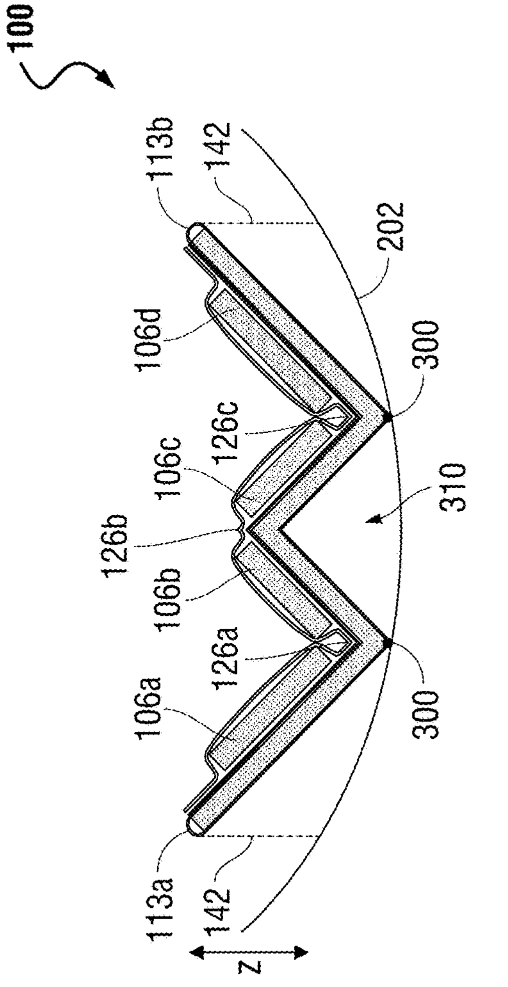
FIG. 9C is another cross-sectional view of a W-shaped core in the central crotch region attached with a backsheet of a chassis.
Figure 9E:
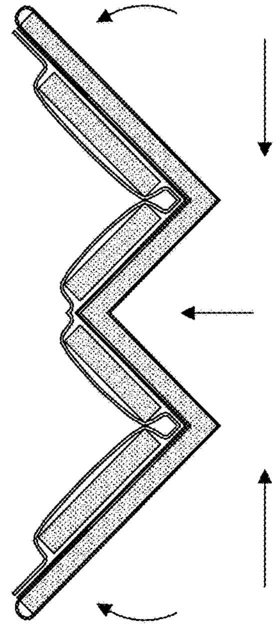
FIG. 9E is a cross sectional view of a W-shaped core in the central crotch region, showing forces exerted thereon.

In use, the fold lines 126*a*-126*c* of core 100 allow core 100 to dynamically respond to the dynamically changing forces that are imparted upon core 100 when worn by a user. For example, as a user walks, the forces imparted upon the core 100 vary with movement of the user's legs. The fold lines 126*a*-126*c* allow for the core 100 to at least partially fold and at least partially unfold dynamically in response to the variations in force imparted thereto. FIG. 9E shows some of the forces subjected to core 100 during use, as indicated via the force lines (arrows). FIG. 9F illustrates the "wing sections" 905 of the absorbent core. The wing sections 905 are fixed at "fixed fold lines" 907, but free to move relative thereto as a result of "unfixed, raised edges" 901. Also, the centrally located "unfixed, raised center fold line" 903 allows the central portion of the absorbent core to move relative to the fixed fold lines 907, forming an air channel 909. The selection of which fold lines are fixed and which are free relative to an underlying chassis (not shown for clarity), allows for the design of an absorbent core that folds in a prescribed way. As shown, the absorbent core of FIG. 9E is designed to fold in a W-shaped configuration. As used herein, unless stated otherwise, when one component is said to be "free" of another component (e.g., an absorbent core that is free of the backsheet", this refers to the fact that movement of the free component relative to the other component is not restrained by the free component at the location indicated. For example, an absorbent core that is free of the backsheet along a particular fold line is free to move relative to the backsheet at least along that fold line, without restraint.

In some aspects, fibrous construction sections 106*a*-106*d* are four relatively firm fibrous sections, with three fold lines between adjacent fibrous construction sections 106*a*-106*d*. The firmness of the fiber network of the sections 106*a*-106*d* provides a structural integrity to each section 106*a*-106*d*, facilitating the folding thereof, relative to other such sections, without deformation or substantial deformation of the sections. In some aspects, the depth of channels 114*a*-114*c* (gaps between sections) in conjunction with the width of the channels 114*a*-114*c* provides a pivot point about which sections 106*a*-106*d* can fold to enter the W-shaped configuration. The attachment of the upper nonwoven sheet 116 to the intermediate nonwoven sheet 118 at a bottom of the channels 114_a_-114_c_ at least partially defines such pivot points. Also, when incorporated into an absorbent article, the absorbent core is fixed at bond lines to the chassis thereof, with a middle fold line free of the chassis and with the lateral edges of absorbent core free of the chassis, such that the absorbent core may fold, with free portions of the absorbent core lifting above the chassis and bonded sections fixed to the chassis. In some such aspects, with four fibrous construction sections having three relatively wide channels positioned between adjacent sections, the absorbent core folds into a W-shaped configuration.

The fiber network of the upper absorbent construction 102 retains the SAP deposited therein, and the SAP absorbs fluid, reducing the wet burden on the fiber network; thereby, allowing the fiber network and upper absorbent construction 102 to maintain structural integrity (wet and dry). With structural integrity maintained, the upper absorbent construction 102 is capable of maintaining the folded (e.g., W-shaped) configuration in both wet and dry conditions.

Figure 9G:
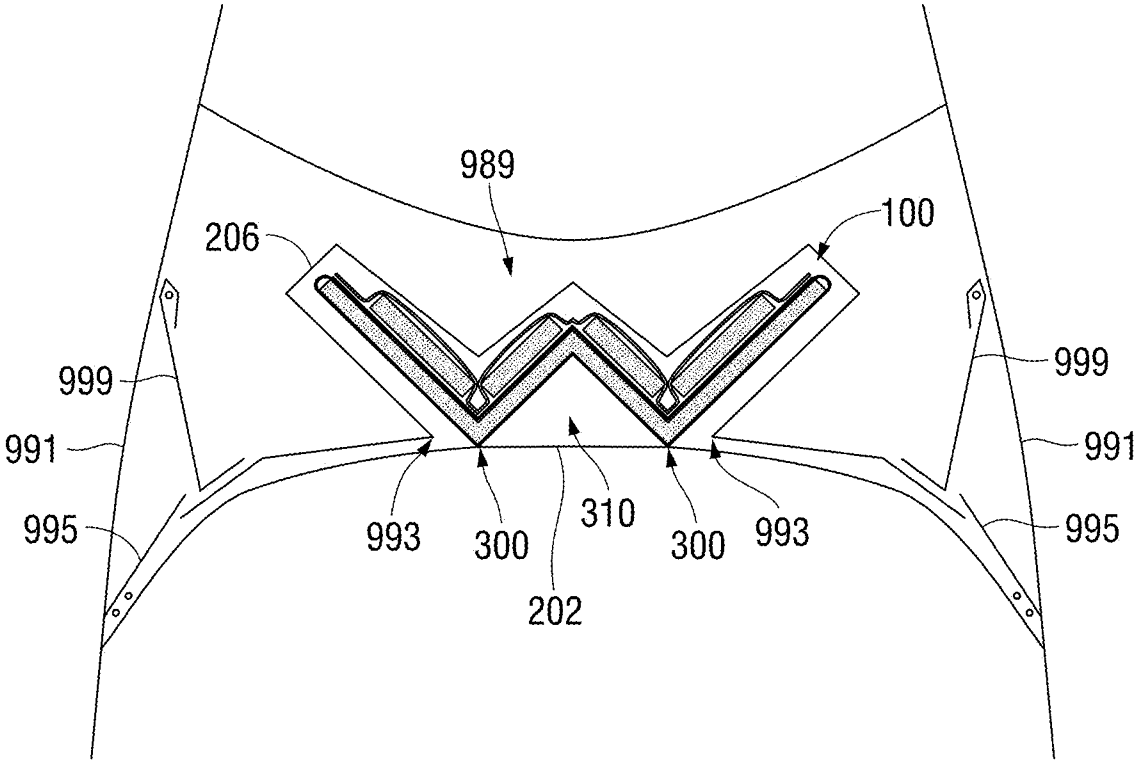
FIG. 9G is a cross sectional view of a W-shaped core incorporated into an absorbent article and worn by a user, with the topsheet conforming to the shape of the core.
Figure 9H:
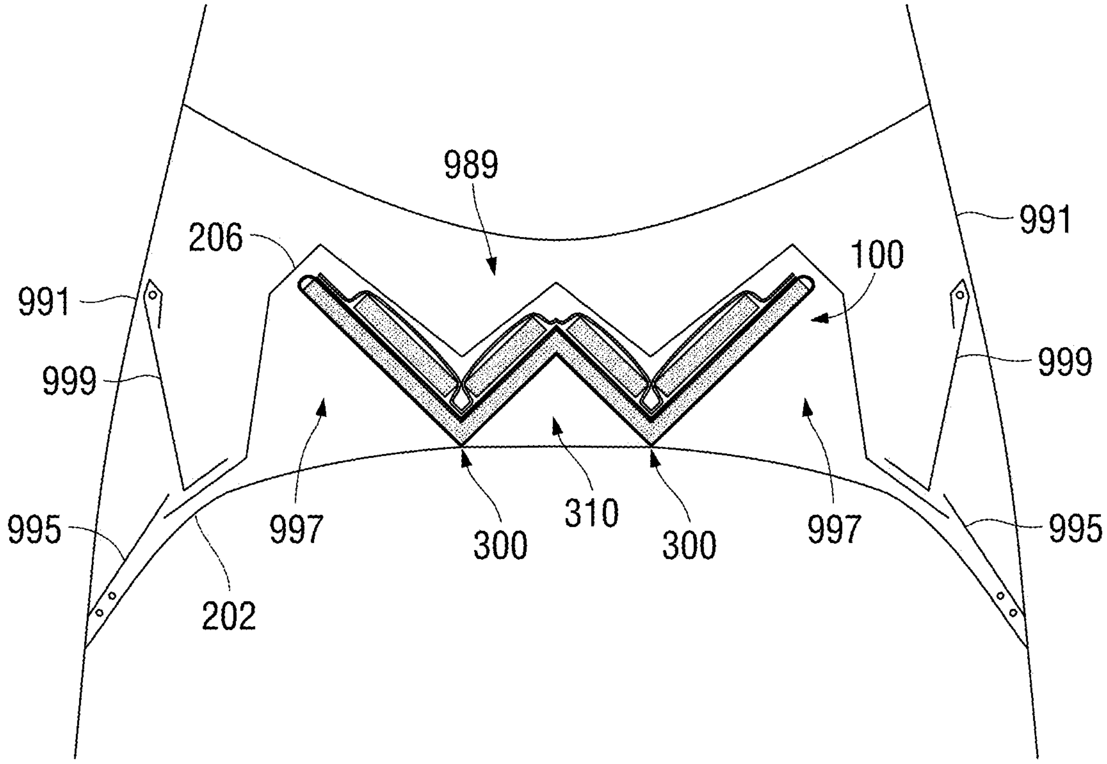
FIG. 9H is a cross sectional view of a W-shaped core incorporated into an absorbent article and worn by a user, with the topsheet free of the bottom of the core.

FIGS. 9G and 9H depict exemplary absorbent cores incorporated into absorbent articles and worn by a user. As shown in FIG. 9G, topsheet 206 may conform to the absorbent core 100, such as via adherence between topsheet 206 and a bottom surface of the absorbent core 100, such that core 100 is encased or encapsulated by topsheet 206. Topsheet 206 may be folded underneath core 100 and adhered thereto. Top sheet 206 may be coupled (e.g., adhered) with backsheet 202 at attachment sites 993 to maintain encapsulation of top sheet 206 about core 100. Alternatively, as shown in FIG. 9H, topsheet 206 may be free of the absorbent core 100 (e.g., not adhered to the bottom surface of the absorbent core 100 and not folded thereunder), such that space 997 is formed between topsheet 206, core 100 and backsheet 202. Also shown are the position and arrangement of leg cuffs 999 relative to topsheet 206, backsheet 202, and core 100, as well as leg gatherers 995. Leg cuffs 999 and leg gatherers 995 enhance fit of the absorbent article with the user's thighs 991, and prevent leakage. Absorbent core 100 is positioned centrally within the crotch region 989. When worn, the free portions of core 100, that is the portions not bonded to backsheet 202 at attachment sites 300 are encouraged upwards, towards the user's crotch, creating the W-shaped core.

Fibrous Construction with Gradient SAP and Adhesive Distributions

Figure 10A:
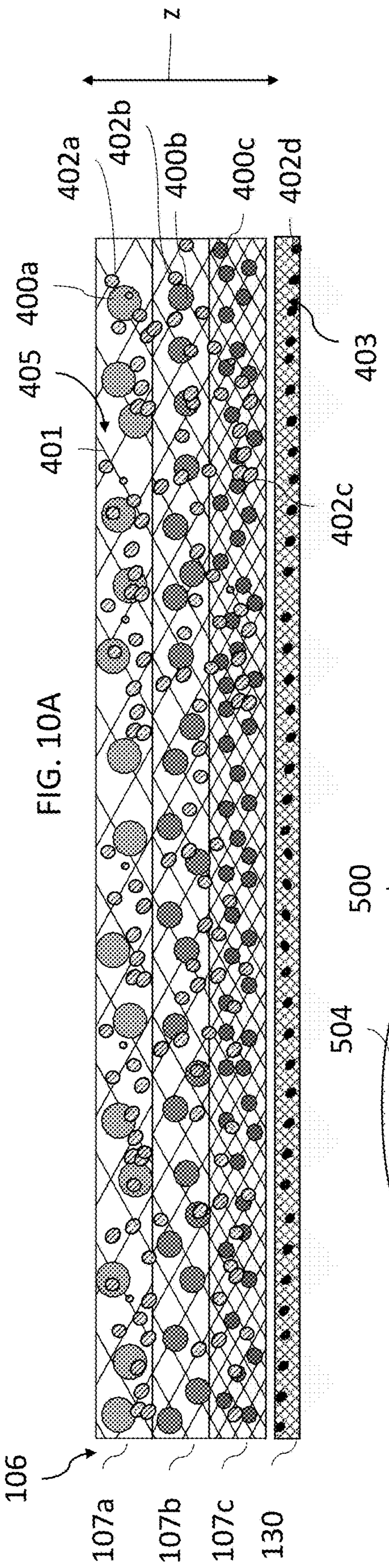
FIG. 10A shows a bulky nonwoven with a gradient distribution of SAP and adhesive.

In some aspects, the absorbent core disclosed herein exhibits a gradient distribution of SAP or other absorbent material, a gradient distribution of adhesive, or combinations thereof. With reference to FIG. 10A, a portion of an exemplary core 100 is shown, including a fibrous construction 106 above and adjacent a lower fibrous construction 130. For simplification, not all components or layers of core 100 are necessarily shown in FIG. 10A, such that only a portion of fibrous construction 106 and a portion of lower fibrous construction 130 are shown.

In FIG. 10A, fibrous construction 106 is shown as a multi-layer fibrous construction, including three layers 107_a_-107_c_. However, the fibrous constructions disclosed herein are not limited to including three layers, and may include any number of layers, including one single layer or multiple layers other than three-layers (e.g., two layers or four layers). Layers 107_a_-107_c_ may be different sections of a single fibrous construction having different properties, or may be multiple sublayers laminated together to form fibrous construction 106.

In some aspects, fibrous construction 106 having layers 107_a_-107_c_ is a unitary structure exhibiting a gradual change in density going from one surface to another. Such a structure may be made using a three-stage process where the component fibers are deposited to form a web using three different, sequential carding operations building up the layers one by one. Each carding operation can provide a different type and/or amount of fiber. The result is a unitary structure with three different strata of density. In some aspects, the material has just one density (no gradient density), and a gradient density is then created by bulkification or heat expansion of one surface to reduce the density on one side.

As shown, core 100 exhibits a gradient distribution of absorbent material, here SAP 400_a_-400_d_, in the z-direction (i.e., from an upper surface 404 of the core 100 to a lower surface 406 of the core 100). In FIG. 10A, the SAP 400_a_-400_d_ is gradient with respect to particle size, such that the larges particle size SAP 400_a_ is positioned and retained in upper layer 107_a_ of fibrous construction 106. SAP 400_b_, which is smaller in particle size than SAP 400_a_, is positioned and retained in intermediate layer 107_b_ of fibrous construction 106. SAP 400_c_, which is smaller in particle size than SAP 400_b_, is positioned and retained in lower layer 107_b_ of fibrous construction 106. SAP 400_d_, which is smaller in particle size than SAP 400_c_, is positioned and retained in pulp layer of the lower fibrous construction 130. While the gradience in SAP 400_a_-400_d_ is shown and descried as a gradience in particle size, the core is not limited to having such a gradience. The absorbent material within core may exhibit a gradience in the z-direction with respect to: particle size, absorbent properties, number of particles, or combinations thereof. From FIG. 10A, it is evident that fibers 401 are more spaced apart in layer 107_a_, providing for larger pores 405; therefore, a lower density relative to layers 107_b_ and 107_c_.

The methods of attaining such a gradience of absorbent material are described in more detail below. However, briefly, superabsorbent particles may be introduced into the bulky nonwoven by any suitable process, including scatter processes, air stream impregnation, and in-situ polymerization. In some aspects, the superabsorbent particles are introduced via an air stream into the lowest density side of the bulky nonwoven (i.e., at surface 404). The superabsorbent particles will penetrate through the bulky nonwoven, and at least some of the superabsorbent particles are trapped and held by the fibers of the bulky nonwoven. The superabsorbent particles may exhibit a wide particle size distribution. Larger particles will typically be trapped and held in the relatively lower density regions of the bulky nonwoven, and smaller particles will typically be trapped in the relatively higher density regions of the bulky nonwoven. The result is a multi-layer absorbent web having different particle size populations in each of the layers 107_a_-107_c_. At least some of the superabsorbent particles deposited onto fibrous construction 106, such as fines, may not be captured by the bulky nonwoven and may pass therethrough. In some aspects, to avoid the buildup of such fine particles in the particle applicator, potentially leading to blocked filters and non-ideal particle size distributions in the final product, the fine particles, SAP 400_d_, are collected and deposited onto the fluff/pulp mixture 403 from which the pulp layer of the lower fibrous construction 130 is formed.

SAP-filtration capabilities of the bulky nonwoven serves to increase concentration of larger particles in the upper region of the bulky nonwoven and smaller particles in the lower region of the bulky nonwoven. Such SAP-filtration effects may be tuned with SAP particle size distribution and bulky nonwoven density.

In some aspects, fibrous construction 106 is a layer of bulky nonwoven that contains superabsorbent particles (SAP) 400*a*-400*c*. The bulky nonwoven of fibrous construction 106 may be a high loft, low density, high thickness nonwoven. In some aspects, the bulky nonwoven of fibrous construction 106 is made from any of the following fibers: polyethylene (PE) fibers, polypropylene (PP) fibers, polyethylene terephthalate (PET) fibers, or combinations thereof. In some aspects, the fibers of the bulky nonwoven are or include bicomponent fibers, such as PE/PP fibers or PE/PET fibers. For example, fibrous construction 106 may be or include an airthrough bonded nonwoven including PE/PET bicomponent fibers. For multi-layer bulky nonwovens, as shown in FIGS. 10A-10D, each of layers 107*a*-107*c* may have having different fiber combinations, different fiber densities, or different porosities, or combinations thereof. In some aspects, the different layers 107*a*-107*c* are arranged such that layer 107*c* has a higher density than layer 107*b*, and layer 107*b* has a higher density than layer 107*a*. The methods of attaining different fiber densities and/or porosities are described in more detail below.

As shown, core 100 exhibits a gradient distribution of adhesive 402*a*-402*c*, in the z-direction (i.e., from an upper surface 404 of the core 100 to a lower surface 406 of the core 100). In FIG. 10A, the adhesive 402*a*-402*c* is gradient with respect to amount (e.g., weight, volume, concentration and/or packing density), such that a lesser amount of adhesive 402*a* is positioned and retained in upper layer 107*a* of fibrous construction 106. The amount of adhesive 402*b* positioned and retained in intermediate layer 107*b* of fibrous construction 106 is more than the amount of adhesive 402*a* positioned and retained in upper layer 107*a* of fibrous construction 106. The amount of adhesive 402*c* positioned and retained in lower layer 107*c* of fibrous construction 106 is more than the amount of adhesive 402*b* positioned and retained in intermediate layer 107*b* of fibrous construction 106.

The methods of attaining such a gradience of adhesive are described in more detail below. However, briefly, to enhance the capture of the superabsorbent particles by the bulky nonwoven of fibrous construction 106, a tackifying adhesive, adhesive 402*a*-402*c*, is added as a surface coating to some or all of the fibers of the bulky nonwoven of fibrous construction 106. The tackifying adhesive 402*a*-402*c* may be a low viscosity adhesive that is sprayed onto the bulky nonwoven, such that the adhesive 402*a*-402*c* penetrates through the bulky nonwoven and coats the fibers thereof. The addition of adhesive 402*a*-402*c* may function to increase the number of superabsorbent particles retained by the bulky nonwoven as the air-stream carrying the superabsorbent particles passes through the bulky nonwoven. In addition, the adhesive 402*a*-402*c* may function to improve the wet and dry integrity of the bulky nonwoven-SAP composite, fibrous construction 106, during the manufacturing process, transport and final use of the absorbent article product.

Figure 10C:
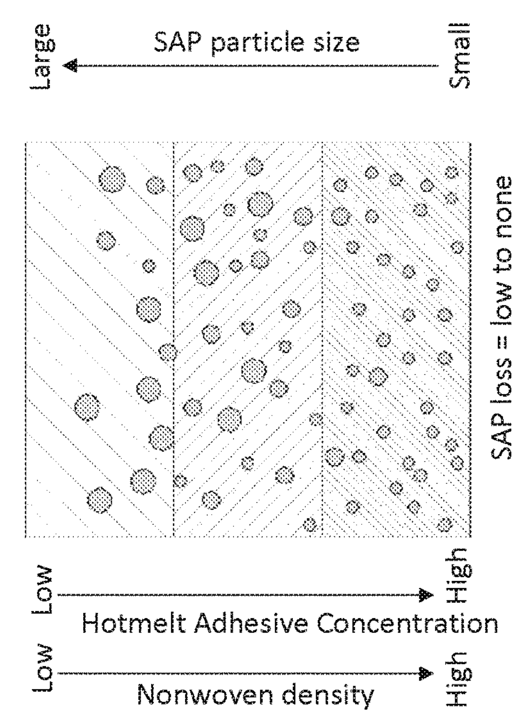
FIG. 10C shows a bulky nonwoven with a gradient distribution of SAP and adhesive.
Figure 10B:
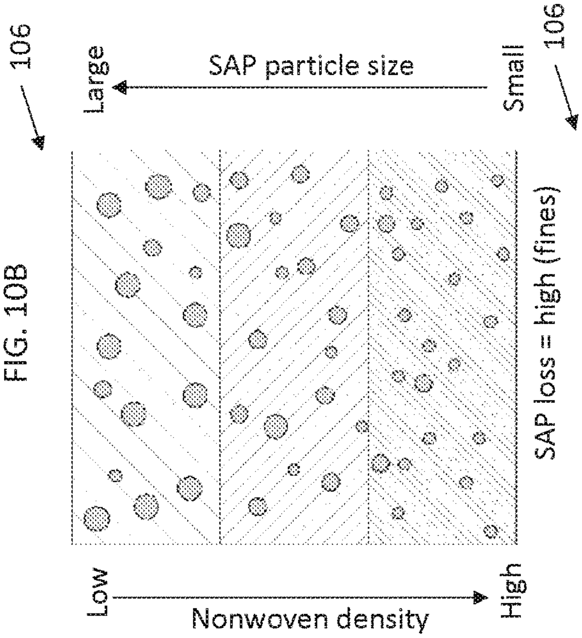
FIG. 10B shows a bulky nonwoven with a gradient distribution of SAP.
Figure 10D:
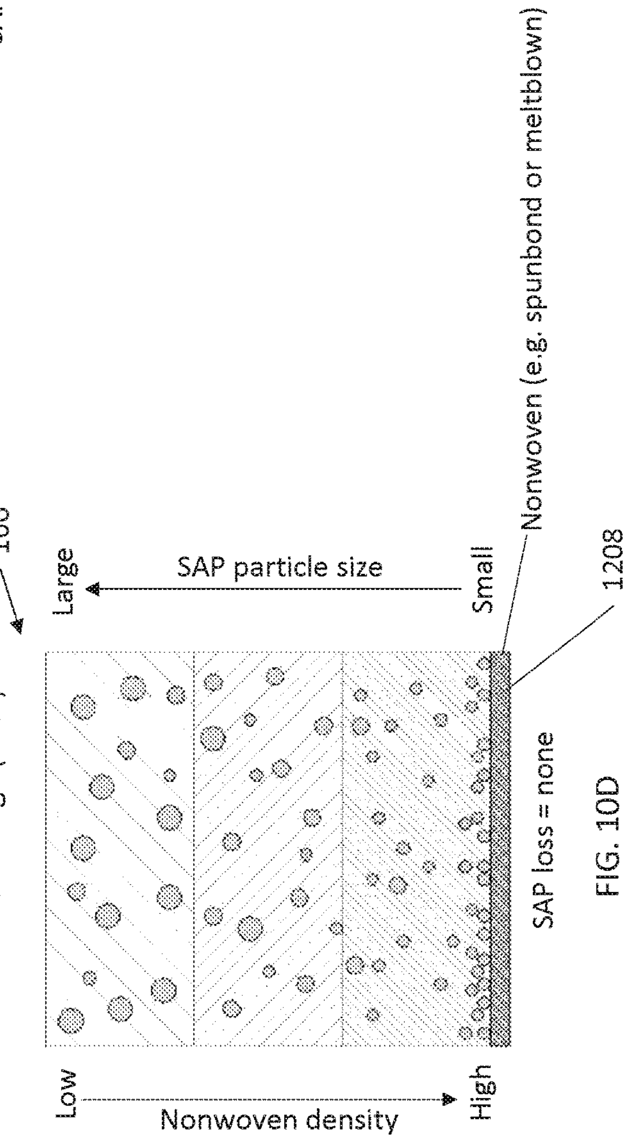
FIG. 10D shows a bulky nonwoven with a gradient distribution of SAP and a capture layer positioned therebelow.

FIGS. 10B-10D further illustrate the distributions of SAP and adhesive in a bulky nonwoven. With reference to FIG. 10B, it is evident that larger SAP particle sizes are captured in lower density sections of fibrous construction 106, while increasingly small SAP particle sizes filter through and are captured in higher density sections of fibrous construction 106. Any lost SAP, that filters entirely through fibrous construction 106, may be SAP fines.

With reference to FIG. 10C, it is further evident that the concentration of hot melt adhesive is higher in higher density sections of fibrous construction 106, and is lower in lower density sections of fibrous construction 106. With HMA in the fibrous construction 106, SAP loss may be low or nonexistent.

With reference to FIG. 10D, it is further evident that the addition of a nonwoven capture sheet 1208 (e.g., spunbond or meltblown), whether in conjunction with hot melt adhesive or not, provides a fibrous construction 106 capable of capturing all or substantially all SAP, such that there is no or substantially no SAP loss.

Table 1, below, sets for a matrix with some exemplary parameters, design selections, and processing selections that may be used in designing a fibrous construction 106 in accordance with the present disclosure. The parameters and selections set forth in Table 1 are not limiting, and other parameters, selections, and variables may be used to design a desired fibrous construction. By selecting the fiber type, fiber pre-treatments (i.e., treatments prior to SAP deposition), SAP deposition parameters, and post-SAP deposition processing, a fibrous construction having desired properties may be designed. Table 1 sets forth selections for eleven exemplary fibrous construction designs. However, any combination of the variables set forth in Table 1 may be used in the design of a fibrous construction. Furthermore, additional variables and selections not listed in Table 1 may also be used to designing a fibrous construction. FIGS. 10E-10J depict some exemplary schematics of certain fiber preparation and SAP deposition processes. However, the present methods are not limited to these particular sequences, and may include any number of permutations and variations without departing from the scope of this disclosure.

TABLE 1

| Fibrous construction Selection and Production Variables | | | | | | | | | | | |
|---|---|---|---|---|---|---|---|---|---|---|---|
| Example Fiber | 1 | 2 | 3 | 4 | 5 | 6 | 7 | 8 | 9 | 10 | 11 |
| Fiber Selection: | | | | | | | | | | | |
| Bulky Nonwoven | * | * | * | * | | | | * | * | | * |
| Nonwoven (not bulky) | | | | | | | * | | * | | |
| Spunbond Nonwoven | | | | | * | * | | | | * | |
| Other fiber | | | | | | | | | | | * |
| Fiber and Layer Variables: | | | | | | | | | | | |
| Multilayer | * | | * | | | * | * | * | * | * | * |
| Single Layer | | * | | * | * | | | | | | |
| Bicomponent | | | * | * | | | | | | | * |
| Nonwoven Capture Sheet on Bottom Surface | | * | | | | | | | * | * | |
| Fiber Density Treatments: | | | | | | | | | | | |

TABLE 1-continued

Fibrous construction Selection and Production Variables

| Example Fiber | 1 | 2 | 3 | 4 | 5 | 6 | 7 | 8 | 9 | 10 | 11 |
|---|---|---|---|---|---|---|---|---|---|---|---|
| Pre-Heating (Bulkifiaction) | * | * | * | | | * | * | | * | * | * |
| In-Situ Heating (Bulkification) | | | | * | | | | | | | * |
| Brushing (Bulkification) | | | | * | | | * | * | | | * |
| IR Irradiation (Densification) | | | * | | | | * | * | | | * |
| Fiber Tackiness Treatments: | | | | | | | | | | | |
| Pre-Heating (e.g., bicomponent fibers) | | | * | | | | | | | | * |
| In-Situ Heating (e.g., bicomponent fibers) | | | | * | | | | | | | * |
| Pre-Spraying Adhesive (onto bottom surface) | * | * | | | | | | | * | | |
| Pre-Spraying Adhesive (onto top surface) | | | | | | | | * | | | |
| In-Situ Pre-Spraying Adhesive | | | | | | | * | | | | |
| Gradient Adhesive Distribution | * | * | | | | | | | * | | |
| Non-Gradient Adhesive Distribution | | | | | | | | * | | | |
| SAP Deposition: | | | | | | | | | | | |
| Within Forced Airstream | * | * | * | | * | | * | | | | |
| Within Heated Forced Airstream | | | | * | | * | | * | * | * | * |
| Simultaneous with Adhesive | | | | | | | * | | | | |
| After Adhesive Application | * | * | * | | | | | | * | | |
| Gradient SAP Distribution | * | * | * | | * | * | * | | * | * | * |
| Non-Gradient SAP Distribution | | | | | | | | * | | | |
| Filtering within and through Fibrous construction | * | * | * | | | * | | | * | * | * |
| Collecting SAP Fines Filtered Through Fibrous construction | * | | * | * | * | | * | * | | | * |
| Capturing All SAP within Fibrous construction | | * | | | | | | | | | |
| Multiple Populations of SAP having different particle sizes | * | * | * | | * | * | | * | * | * | * |
| Post-SAP Deposition: | | | | | | | | | | | |
| Separating Fibrous construction into Multiple Sections | * | * | * | | * | | | | * | * | * |
| Coupling Fibrous construction with Pulp/SAP layer | | * | | | * | * | | | * | * | * |

Figure 10E:
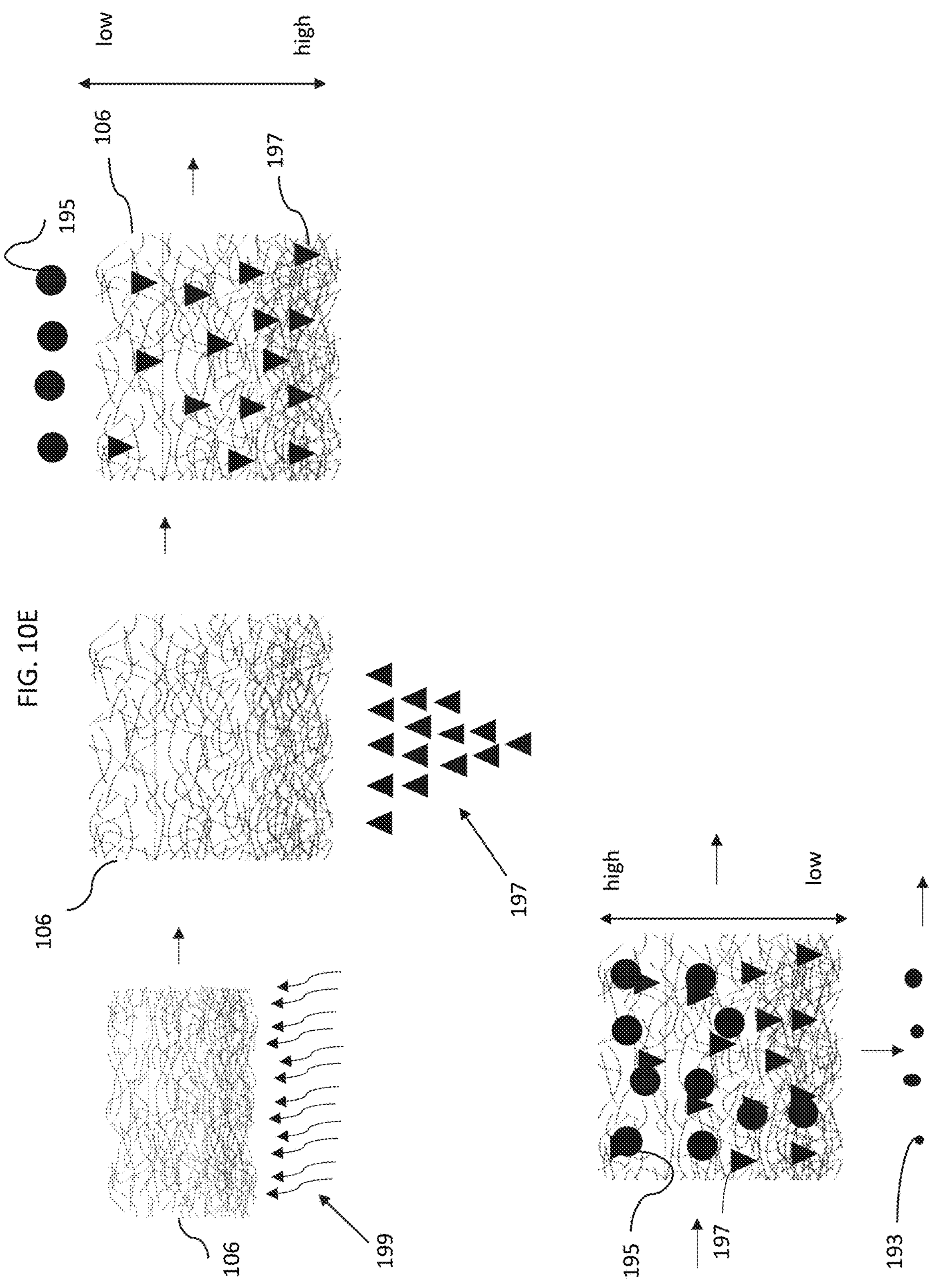
FIGS. 10E-10H depict exemplary fibrous construction preparation and SAP deposition sequences.

FIGS. 10E-10H depict some exemplary fibrous construction preparation techniques. In FIG. 10E, a fibrous construction is subjected to heat to bulkify the fibrous construction. After bulkification, the HMA is sprayed on the fibrous construction from the bottom surface thereof. At least two factors contribute to the formation of a gradient HMA distribution, in terms of HMA concentration, across the fibrous construction, including: (1) that the HMA impacts the fibers toward the lower surface of the fibrous construction, resulting in more HMA contacting and adhering to the fibers towards the bottom of the fibrous construction than towards the top of the fibrous construction; and (2) that the fibrous construction is more dense towards the bottom of the fibrous construction than towards the top of the fibrous construction, further facilitating the capture of HMA fibers. SAP is then applied to the fibrous construction from the top surface thereof, opposite the surface upon which the HMA was sprayed. The SAP filters through the fibrous construction. SAP may be retained within the fibrous structure of the fibrous construction by the fibers thereof via entanglement, as well as by the HMA through adhesion. Larger particles of the SAP have a greater tendency of being captured towards the top surface of the fibrous construction at least in part because the fibrous construction in this example has a gradient density, where the density is higher towards the top surface. With a higher density, the fibers are spread further apart, sufficient to capture larger SAP while allowing smaller SAP to filter deeper into the fibrous construction. As SAP filters deeper into the fibrous construction, the SAP impacts more HMA due to the increasing concentration of HMA towards the bottom surface. Also, as the SAP filters deeper into the fibrous construction, the SAP impacts more fibers of the fibrous construction, as the fibrous construction becomes denser with fibers positioned closer together. This allows the fibrous construction to capture SAP not captured towards the top of fibrous construction. Some SAP particles may be too small to be captured by the fibers or the HMA, and filter through the entire fibrous construction. Such SAP may be SAP fines, which may be collected and diverted to be combined with pulp.

Figure 10F:
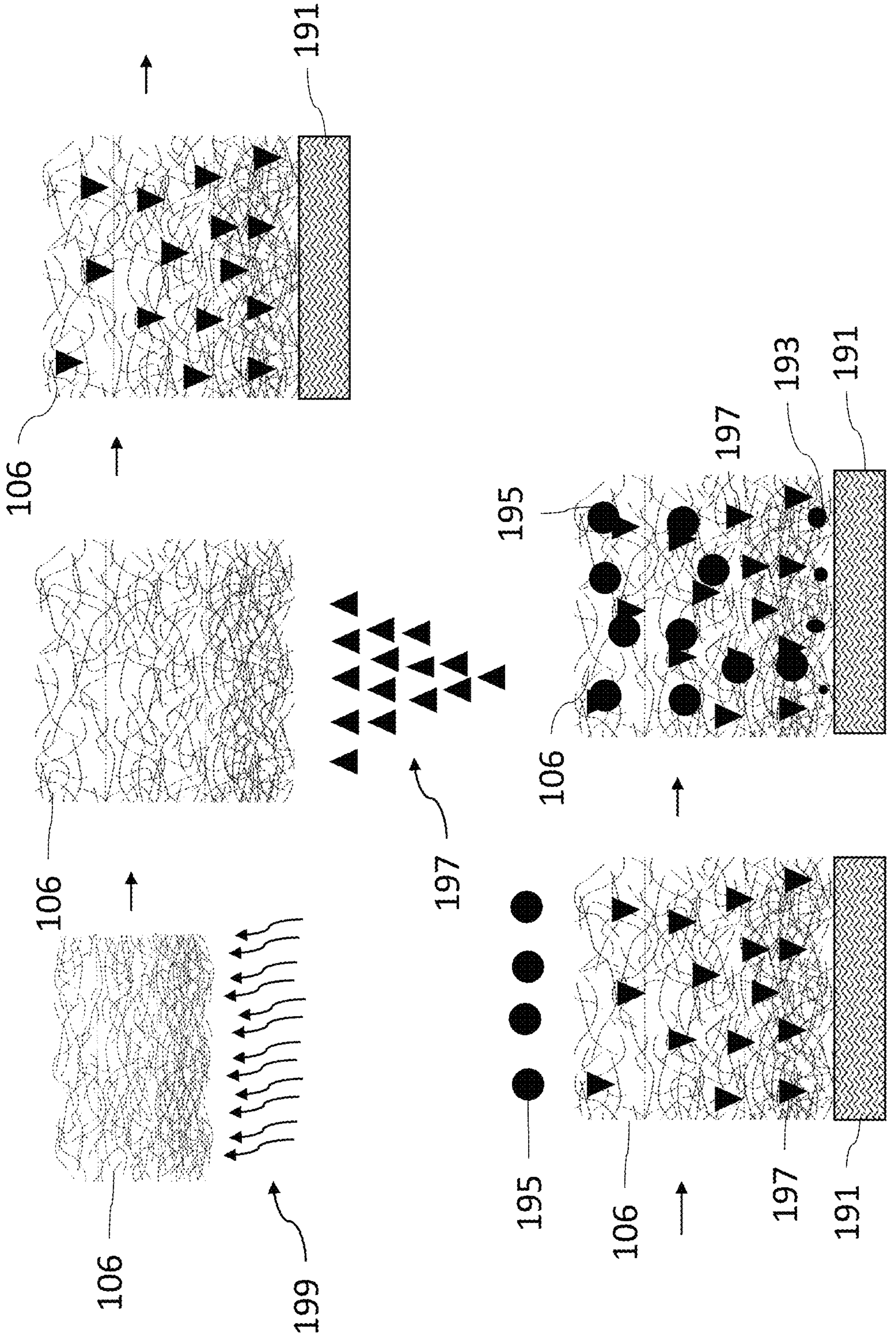

With reference to FIG. 10F, in some aspects a capture layer is coupled with the bottom of the fibrous construction. When SAP is deposited and filtered through the fibrous construction, the capture layer captures the SAP fines, such that the SAP fines are incorporated as a part of the fibrous construction, and are not collected and diverted.

Figure 10G:
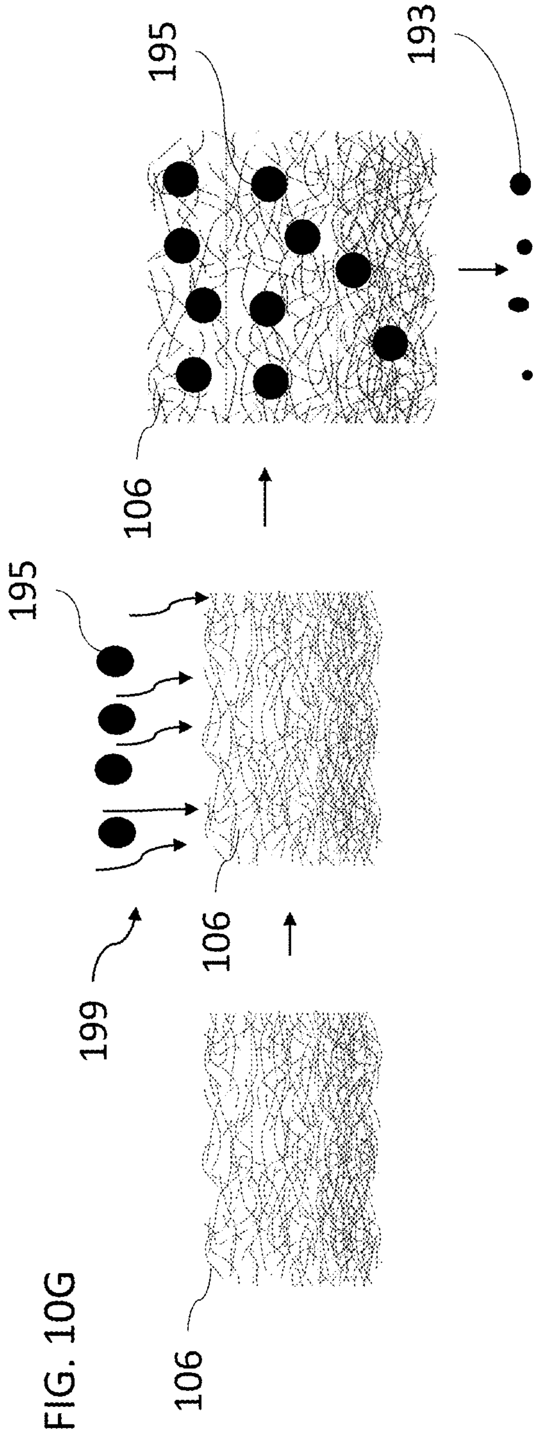

With reference to FIG. 10G, in some aspects the fibrous construction is not bulkified prior to addition of the SAP. The SAP may be introduced to the fibrous construction in a heated, forced air stream, such that bulkification and/or tackification of the fibrous construction occurs simultaneously with the addition of SAP.

Figure 10H:
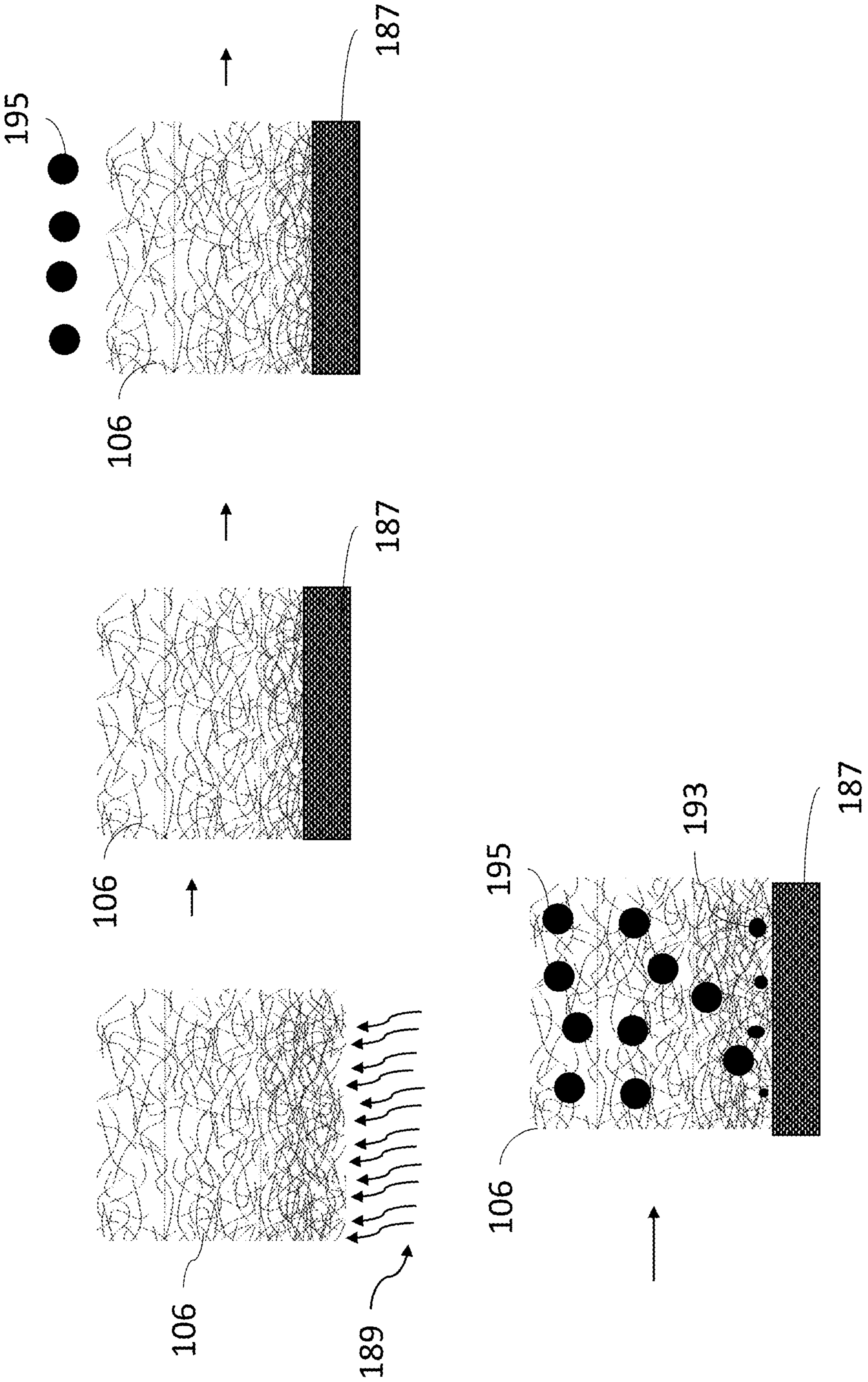
Figures 11C, 11D, 11E, 11F:
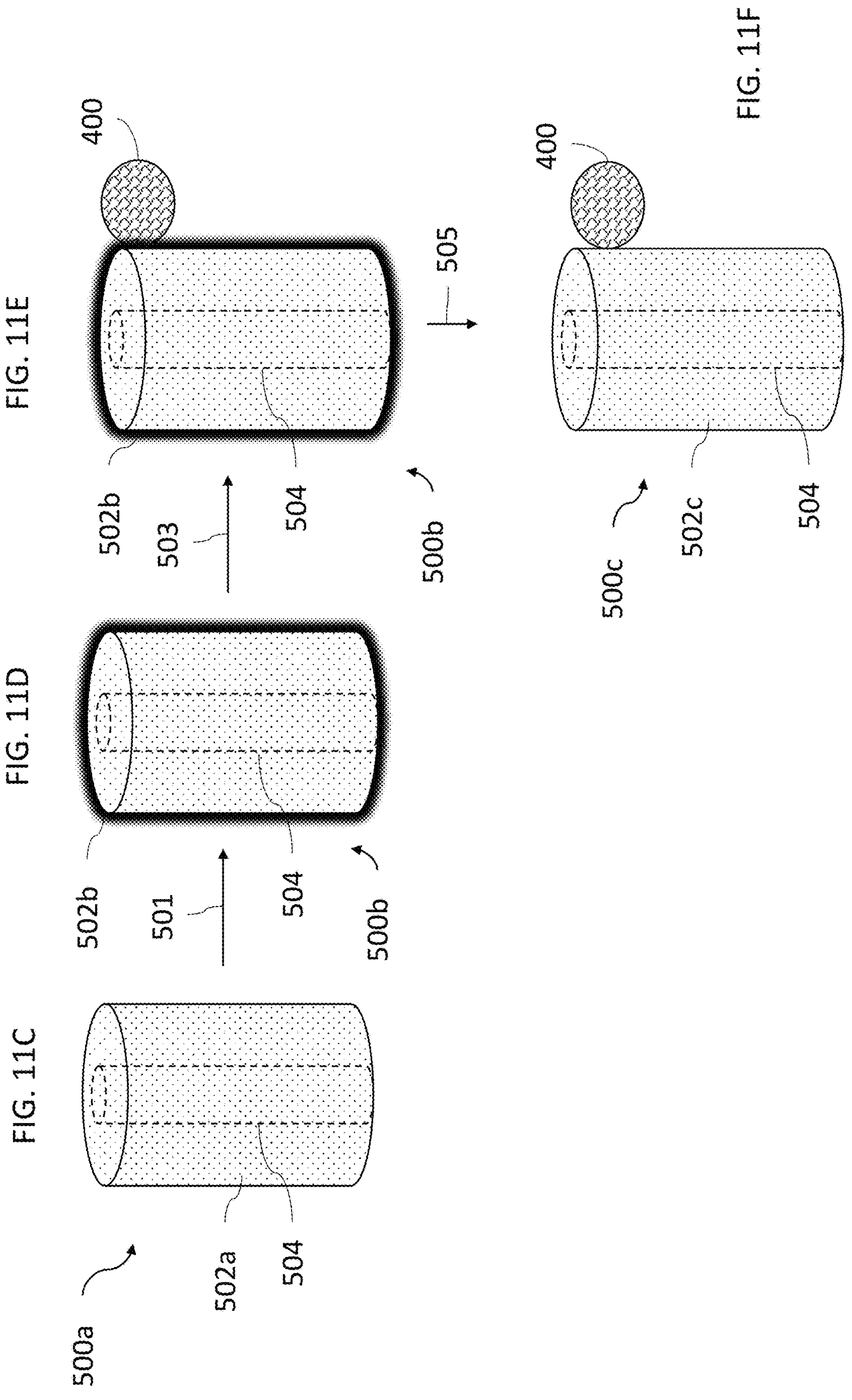
FIGS. 11C-11F illustrate the tackification of a bicomponent fiber and the attachment of SAP thereto.

With reference to FIG. 10H, in some aspects, the fibrous construction is subjected to selective densification at the bottom surface thereof to form a capture layer. When the SAP is deposited, the thusly formed capture layer captures all of the SAP, including SAP fines, such that the SAP fines are incorporated as a part of the fibrous construction, and are not collected and diverted.

Adhesive

In some aspects, adhesive is applied to the bulky nonwoven (or other fibrous construction) via carrying the adhesive in an air stream. The air may be heated air, opening up the fiber network of the bulky nonwoven, resulting in bulkification thereof, such that the more open fiber network facilitates the introduction and penetration of the adhesive into the fiber network. In some aspects, the adhesive is applied as a uniform spray on the fibers. The viscosity of the adhesive may be varied with temperature. As such, the viscosity of the adhesive, when applied, may be controlled by controlling the temperature of the adhesive, when applied.

In some aspects, the adhesive is in the form of particles, including spherical particles, or fibers. In some such aspects, the adhesive is applied as a hot melt spray, which may be more suitable for creating a gradient adhesive distribution in the fibrous construction. In aspects where the adhesive is in the form of particles, an additional heating step may be used to activate the adhesive prior to the application of SAP. The adhesive may be applied to the fibrous construction in the opposite direction from which the SAP is applied, such that the gradience in the adhesive distribution in the fibrous construction is inverse of (opposite of in direction) the gradient in the SAP distribution in the fibrous construction.

In some aspects, the adhesive is applied in a liquid phase/spray application of hotmelt adhesive to provide a binder or matrix to stabilize and partially immobilize SAP particles in the fibrous network. In an extrusion process, hotmelt adhesive is forced through small holes which, in combination with air attenuation, produces elongated polymer strands or fiber of HMA. Deposited on the substrate, the elongated polymer strands of HMA establish a fibrous network capable of holding the SAP particles.

In an alternate method, powdered hotmelt adhesive particles can be mixed with superabsorbent particles and the mixture of unbonded hotmelt particles and superabsorbent particles is applied to the bulky nonwoven. Application of heat to the composite will cause the hotmelt adhesive powder to melt and bind the SAP and bulky nonwoven. The application of heat can be accomplished via a heated, forced airstream, an oven, or IR irradiation, for example.

The selection of hotmelt material and processes as a design element can achieve particularly improved product performance. In further applications, the ratio of hotmelt particles to superabsorbent particles is selected to achieve an optimum balance of dry integrity and restraint on SAP swelling. The ratio of the number of SAP particles to hotmelt particles will determine for example, how many bonding points, contributed by the hot melt particles, per SAP particle are possible. The ratio is determined from the weight percentage, particle size distribution and polymer density of each component. Hotmelt particles are commercially available materials from Abifor. The selection of hotmelt material and processes as a design element can achieve particularly improved product performance. In some applications, water sensitive hotmelt particles may be employed as a mechanism for increasing void space (swell volume). Specifically, a hotmelt is selected that is sensitive to wetting (e.g., a SAP based hotmelt) and thus, to receipt of liquid intake in the absorbent core pockets. These hotmelt particles break down as the SAP particles around it swell with liquid absorption. This relieves the SAP particles from the hotmelt's bind and allow the SAP to swell unrestricted. An example of a water-soluble hot melt is the modified polyvinyl alcohol resin (Gohsenx L series, Nippon Gohsei). An example of a water sensitive hot melt is Hydrolock (HB Fuller).

Figure 11B:
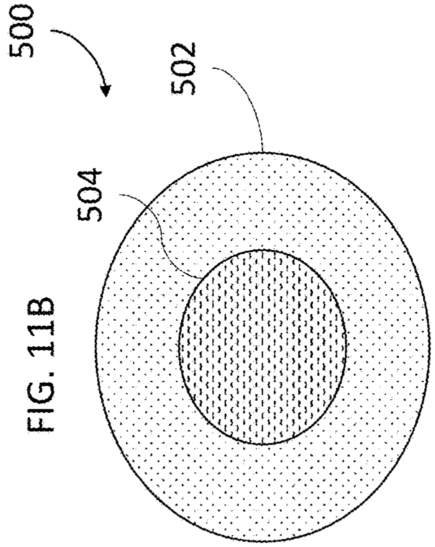
FIG. 11B is an end view of a bicomponent fiber.
Figure 11A:
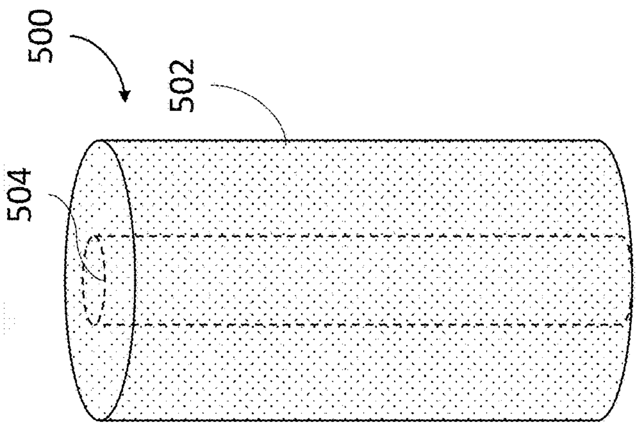
FIG. 11A is perspective view of a bicomponent fiber.

With reference to FIGS. 11A and 11B, an exemplary bicomponent fiber 500 is shown, which may form all or part of the bulky nonwoven of fibrous construction 106. Bicomponent fiber 500 may be a core/sheath (also referred to as a core/shell) particle, including a fiber sheath 502 of a first thermoplastic material and a fiber core 504 of a second thermoplastic material. The second thermoplastic material may have a higher softening point and higher melting point than the first material. For example, the core 504 may be composed of polypropylene and while the sheath 502 is composed of polyethylene (a PE/PP fiber). While described in more detail below, the bicomponent fiber 500 may function as an adhesive for capturing and retaining the SAP during deposition thereof. Thus, in some such aspects, when a bicomponent fiber containing bulk nonwoven is used, adhesive is not added to the bulky nonwoven. With reference to FIGS. 11C-11F, a bulky nonwoven containing bicomponent fibers, fiber 500*a*, may be subjected to heating 501, such that sheath 502*a* is brought to a temperature at which it softens (softening point temperature), but does not melt or does not fully melt, forming bicomponent fiber 500*b* with softened sheath 502*b*. Bicomponent fiber 500*b* is then combined, in a combining step 503, with superabsorbent particles 400. As sheath 502*b* is softened, SAP 400 adheres to sheath 502*b*. Bicomponent fiber 500*b* is then subjected to cooling 505 to a temperature below the softening point thereof, such that sheath 502*b* re-hardens, forming bicomponent fiber 500*c* having re-hardened sheath 502*c*. SAP 400 is thus adhered to sheath 502*c*. Thus, applying SAP to a bicomponent containing bulky nonwoven after having heated the bulky nonwoven to a temperature around or above the softening point of the low melting point thermoplastic material, but below the softening point of the higher melting point thermoplastic material, provides one exemplary method of adhering the SAP to the fibers of fibrous construction 106. Without being bound by theory, it is believed that outside sheath 502 will soften and become tacky upon being heated to a temperature at or around the softening temperature. As the superabsorbent particle filled air-stream passes through the heated bulky nonwoven, the tacky surface of the sheath may facilitate the capture and retention of the superabsorbent particles; thereby, improving the dry and wet integrity of the superabsorbent particle filled nonwoven fiber mixture.

Creped Spunbond

In some aspects, the fibrous construction is or includes a crepe spunbond nonwoven. Exemplary crepe spunbond nonwovens are shown in the images of FIGS. 20A-20E. SAP may be captured and retained within micro-pockets of the crepe spunbond, and distributed in a pattern (due to the bonding pattern of the particular spunbond used). Such a SAP absorbent structure may exhibit high-permeability, even after the SAP is swollen, as the SAP populations are separated from one another. With reference to FIGS. 20A-20E, the loop pattern, loop frequency and loop height directly follow from the bonding pattern in the base spunbond sheet and the level of creping. A coarser bond pattern will create a lower frequency loop pattern but with higher loop height. Higher levels of creping create higher out-of-plane fiber deformations, bigger loops, more bulk and hence lower web density. The loop structure, e.g. size and volume, can be controlled by choice of base spunbond parameters such as bond pattern and fiber sizes together with crepe level. The areas with the fiber loops act as micro pockets that can contain and entrap particles such as superabsorbent particles in a predetermined pattern. Also, a structure with a gradient in particle size containment may be assembled by layering at least two webs of spunbond creped at different creping levels. Additionally, creping adds flexibility, softness and extensibility to the resulting web structure. In some aspects, the creped spunbond web includes z-directionally oriented fiber segments that increase the compressive resistance and z-flow of liquid within the creped spunbond web.

The process of creping serves to impart recoverable extensibility to the creped spunbond web and may be used to further enhance the entrapment of SAP particulates therein; particularly, for webs creped at levels higher than 20%±3%. Such may be accomplished by stretching the creped spunbond web to an extent that is lower than the creping level of the web, prior to the addition of the SAP particles, and allowing the web to retract after SAP particle addition; thereby, increasing the degree of SAP particulate entrapment of the web.

In some aspects, the fibrous construction or the base layer (layer 118) is creped online (e.g., during production within the system shown in FIG. 12A), either as a full width material sheet or as strips or sections (i.e., before or after separation into sections). The level of crepe of a particular strip or layer can be controlled to provide the proper SAP particle capture needed in the absorbent structure. In some aspects, hot melt adhesives are added to the crepe spunbond to enhance SAP particle capture therein.

In some aspects, the fibrous layer, whether crepe spunbond, BNW, or another nonwoven, may be subjected to vibration to further facilitate distribution of SAP therein.

Processes and Systems

In some aspects, the present disclosure includes a system and process for making the absorbent cores and absorbent articles disclosed herein.

Figure 12A:
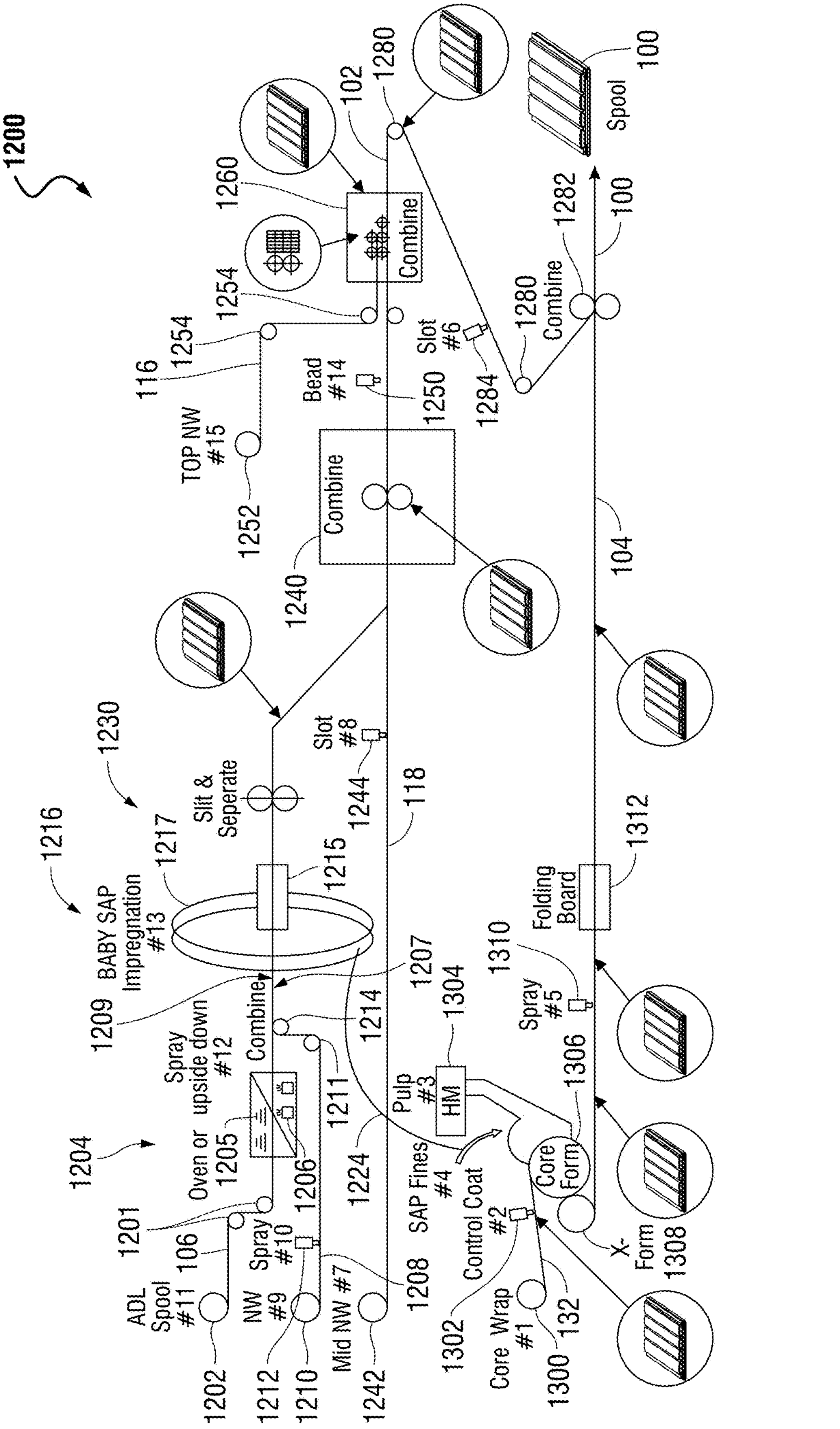
FIG. 12A is a simplified schematic of a system and process for making an absorbent core.
Figures 12B, 12C, 12D:
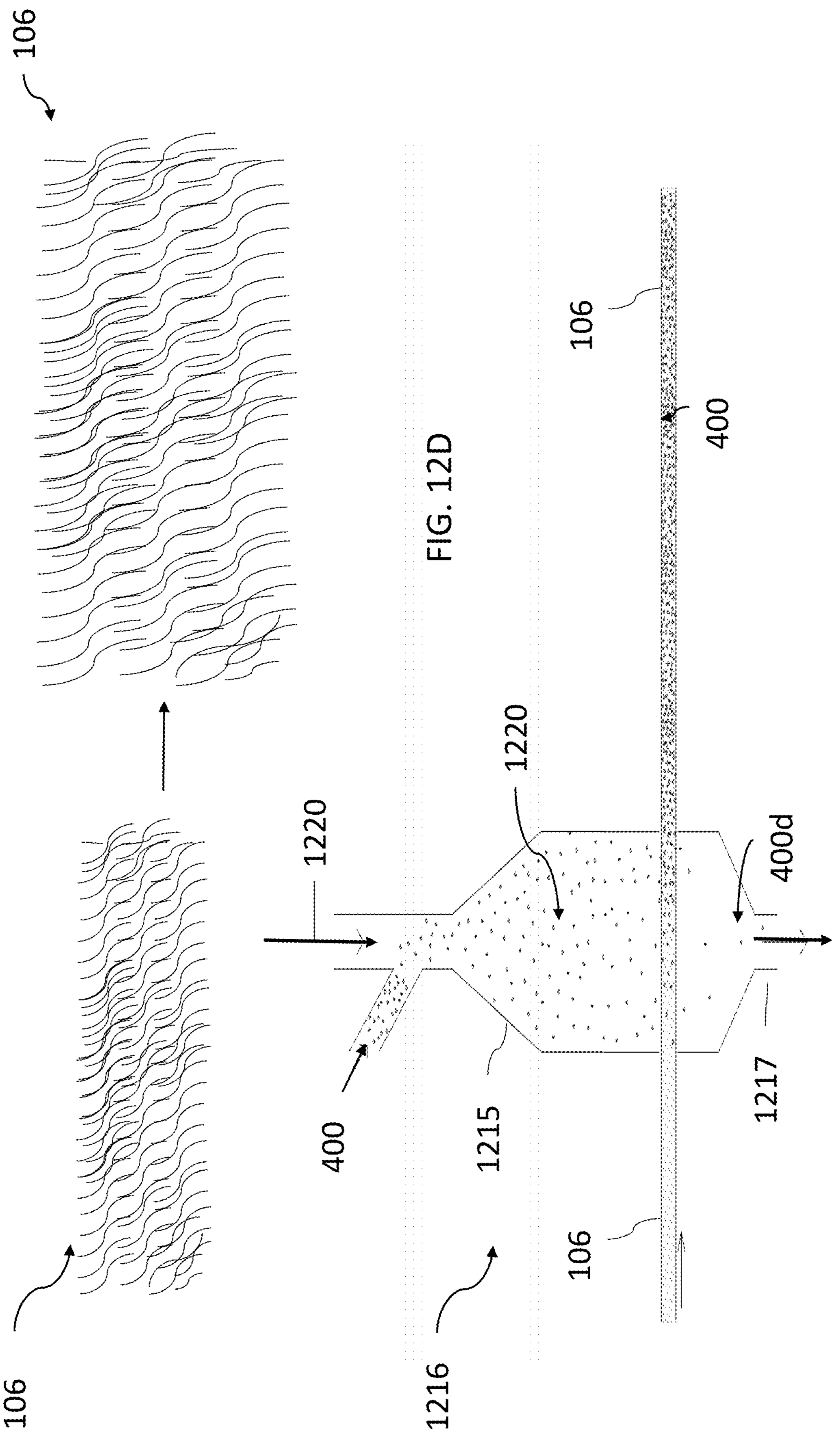
FIGS. 12B and 12C depict the bulkification of a nonwoven.
FIG. 12D depicts the deposition and filtering of SAP on a bulky nonwoven from a forced airstream.
Figures 17A, 17B:
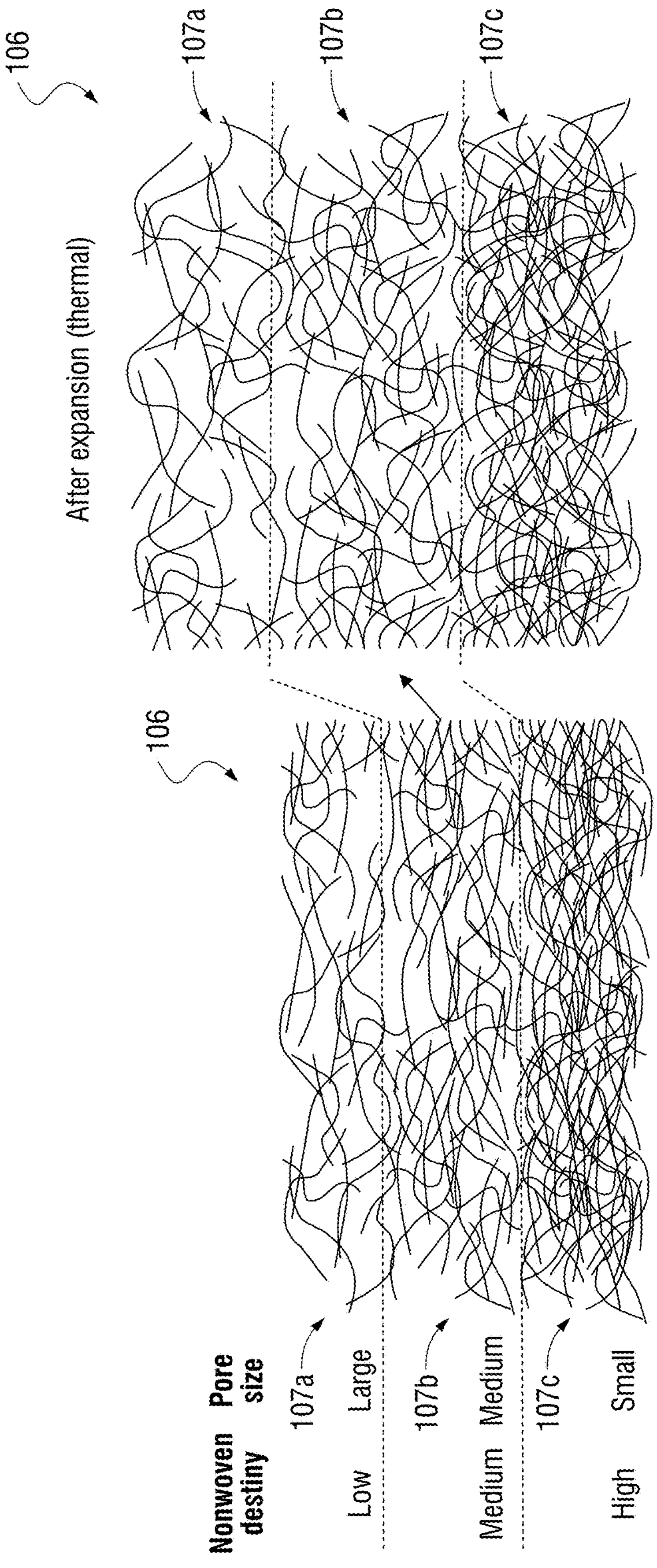
FIGS. 17A and 17B depict the bulkification of a nonwoven.

With reference to FIG. 12A, one exemplary system and process schematic is shown and described. System 1200 may be used to form absorbent cores in accordance with the present disclosure. To make one exemplary absorbent core, fibrous construction 106 is dispensed from spool 1202. Fibrous construction 106 passes over rollers 1201 to fiber tackifier 1204. Fibrous construction 106 passes through fiber tackfier 1204, such that upon exit from fiber tackifier 1204, the fibers of fibrous construction 106 exhibit an increased tackiness relative to the tackiness of the fibers prior to entry into fiber tackifier 1204. In some aspects, fiber tackifier 1204 is or includes an oven or other apparatus that subjects fibrous construction 106 to heat 1205. In some such aspects, the heat is sufficient to increase the temperatures of the fibrous construction 106 such that bulkification occurs to at least a portion of fibrous construction 106, resulting in a bulkified bulky nonwoven. For example, FIGS. 12B and 12C show a fibrous construction 106 prior to and after bulkification, respectively. Bulkification may facilitate the ability of fibrous construction 106 to receive, capture, and/or filter SAP, such as in accordance with the size of the SAP. When fibers of fibrous construction 106 are bicomponent fibers, the heat from fiber tackifier 1204 may result in softening of the sheath of the fibers, as shown and described with reference to FIGS. 11C-11F. FIGS. 17A and 17B depict a, perhaps, more detailed illustration of bulkification of a multi-layer nonwoven 106 having layers 107*a*-107*c*.

While not shown, in some aspects, fiber tackifier 1204 is or includes an IR generator for selectively impacting certain portions or surfaces of fibrous construction 106 with IR radiation. The IR radiation may be used to selectively densify (opposite of bulkify) the portions of fiber that it impacts. For example, IR radiation may be impacted only upon the bottom surface 1207 of fibrous construction 106 to densify only the bottom surface 1207 of fibrous construction 106. Densification of the bottom surface 1207 of fibrous construction 106 may facilitate the retention of smaller sized SAP particles by fibrous construction 106, by forming a dense bottom surface 1207 of fibrous construction capable of capturing and retaining SAP of a particle size that is too small to be captured in other sections of the fibrous construction 106.

In some aspects, fiber tackifier 1204 is or includes an adhesive applicator 1206, such as an adhesive spray gun. Adhesive applicator 1206 may apply adhesive (e.g., a low tack adhesive) to fibrous construction 106 as fibrous construction 106 passes therethrough to coat the fibers thereof with adhesive; thereby, increasing the tackiness of the fibers. In some such aspects, adhesive applicator 1206 is positioned only on one side of fibrous construction 106, such that adhesive is sprayed or otherwise applied to fibrous construction only from that one side. For example, adhesive applicator 1206 may be positioned below fibrous construction 106 (as shown), such that adhesive is applied to the bottom surface 1207 of fibrous construction 106. In some such aspects, by applying adhesive only onto and through the bottom surface 1207, a gradient distribution of adhesive within the body of fibrous construction 106 is attained, such as is shown in FIGS. 10A-10D. Fibers at or closer to bottom surface 1207 will be impacted with the adhesive prior to impact between fibers further from the bottom surface 107, such that more adhesive adheres to and is retained at or proximate bottom surface 1207 than at or proximate top surface 1209.

In some aspects, fiber tackifier 1204 includes the use of IR radiation, heating, adhesive application, or any combination thereof. In some aspects, the bulky nonwoven is bulkified using mechanical methods, such as via brushing. For example, in some embodiments nonwoven or bulky nonwoven may be bulkified via the methods disclosed in U.S. Patent Publication No. 2019/0290505, filed on Mar. 22, 2019. In some aspects, forced airstream 1218 (FIG. 12B) is at a temperature sufficient to tackify fibrous construction 106. In some such aspects, heat from forced airstream 1218 is used to tackify fibrous construction 106. In other aspects, heat from forced airstream 1218 is combined with one or more of brushing, IR radiation, other heating (e.g., oven heating), and adhesive application to tackify fibrous construction 106.

In some aspects, the tackified fibrous construction 106 is combined with a nonwoven capture sheet 1208. Nonwoven capture sheet 1208 may be a denser nonwoven than fibrous construction 106. In some aspects, nonwoven capture sheet 1208 is not a bulky nonwoven. Nonwoven capture sheet 1208 is dispensed from spool 1210. Adhesive may be applied to nonwoven capture sheet 1208, such as via adhesive spray gun 1212. Nonwoven capture sheet 1208 may then pass over roller 1211 to combining roller 1214. Tackified fibrous construction 106 is then combined with nonwoven capture sheet 1208 on combining roller 1214, where adhesive on nonwoven capture sheet 1208 provides adherence between nonwoven capture sheet 1208 and tackified fibrous construction 106. In use, the increased density of nonwoven capture sheet 1208 allows nonwoven capture sheet 1208 to capture SAP particles that are too fine in particle size for fibrous construction 106 layer to capture, such that the fine SAP particles pass through fibrous construction 106. In some aspects, nonwoven capture sheet 1208 is not used.

Tackified fibrous construction 106, combined with nonwoven capture sheet 1208, then passes to SAP impregnator 1216. SAP impregnator 1216 may be or include an airforming process for SAP deposition. SAP impregnator 1216, a detailed view of which is also shown in FIG. 12D, generates a high velocity, forced airstream 1218 to which SAP 400 is combined within chamber 1215. SAP-containing airstream 1220 then flows down towards fibrous construction 106 and is filtered therethrough. The high velocity of SAP-containing airstream 1220 serves to reduce or prevent the buildup of SAP 400 on the top surface of fibrous construction only, such that the SAP filters therethrough. Fibrous construction 106 acts as a filter, to capture and hold the SAP particles. As fibrous construction 106 is tackified, SAP 400 is adhered to the fibers thereof. SAP 400 may be distributed within fibrous construction 106, such as is shown in FIGS. 10A-10D. In some aspects, all SAP 400 is captured within fibrous construction 106. For example, in some aspects the lowest layer (e.g., 107*c*) of fibrous construction 106 is of sufficient fiber density to capture and retain all SAP 400 within SAP-containing airstream 1220, or nonwoven capture sheet 1208 is of sufficient fiber density to capture and retain all SAP 400 within SAP-containing airstream 1220. However, in other aspects, at least some SAP 400 filters completely through fibrous construction 106, SAP fines 400*d* (as shown in FIG. 12D). Such fines may be recycled in a loop 1217 back over fibrous construction 106. However, in other aspects, such SAP fines 400*d* is collected and/or diverted to a secondary air-forming process for application to pulp layer 130, as indicated via SAP diversion pathway 1224 in FIG. 12A, which is described in more detail below. As filtered SAP may be diverted, in some aspects the process of making core 100 results no loss of SAP or substantially no loss in SAP. While not shown, in some aspects adhesive is added to SAP-containing airstream 1220 or forced airstream 1218. In some aspects, SAP is selectively deposited at selected positions on fibrous construction 106. For example, a diverter valve, pulsed SAP deposition, the use of a blind to block SAP deposition, and other such methods may be used to vary the SAP application over time and/or space to create a y-gradient (MD) of SAP. In some aspects, SAP properties may be varied depending on the expected position of SAP within core 100. For example, the position may be predicted based upon the SAP particle size.

Figure 12E:
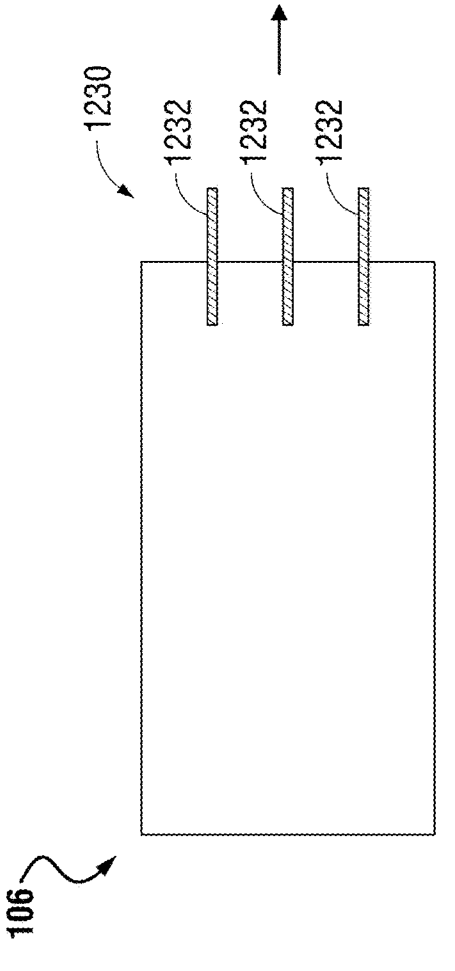
FIGS. 12E and 12F depict the cutting of a bulky nonwoven into sections.
Figure 12F:
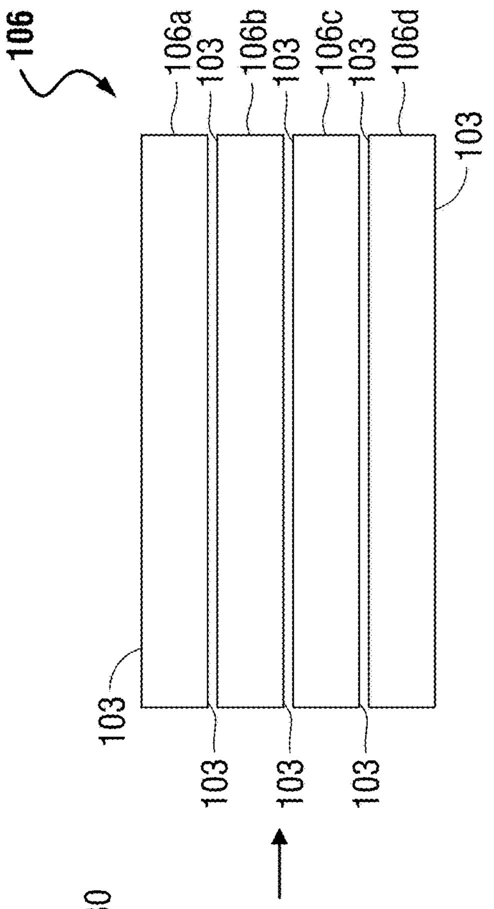
Figure 12G:
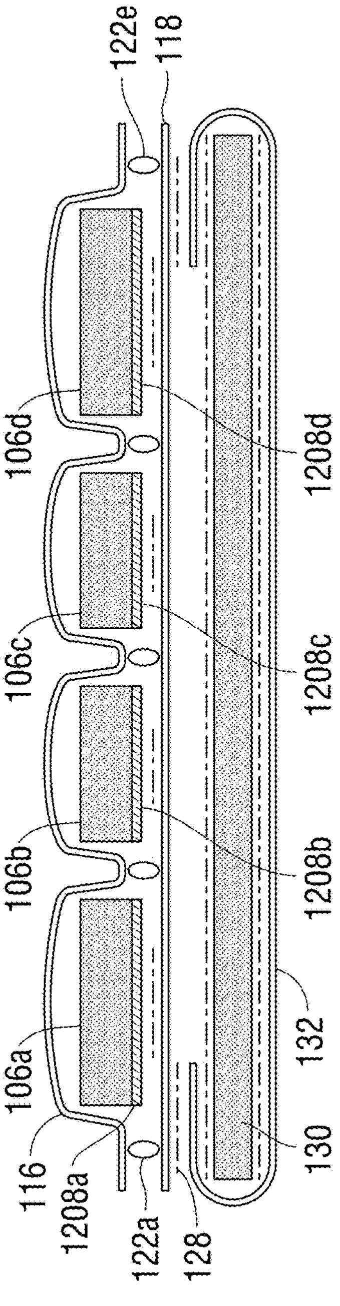
FIG. 12G depicts a core having a nonwoven capture sheet positioned below bulky nonwoven sheets.
Figure 12H:
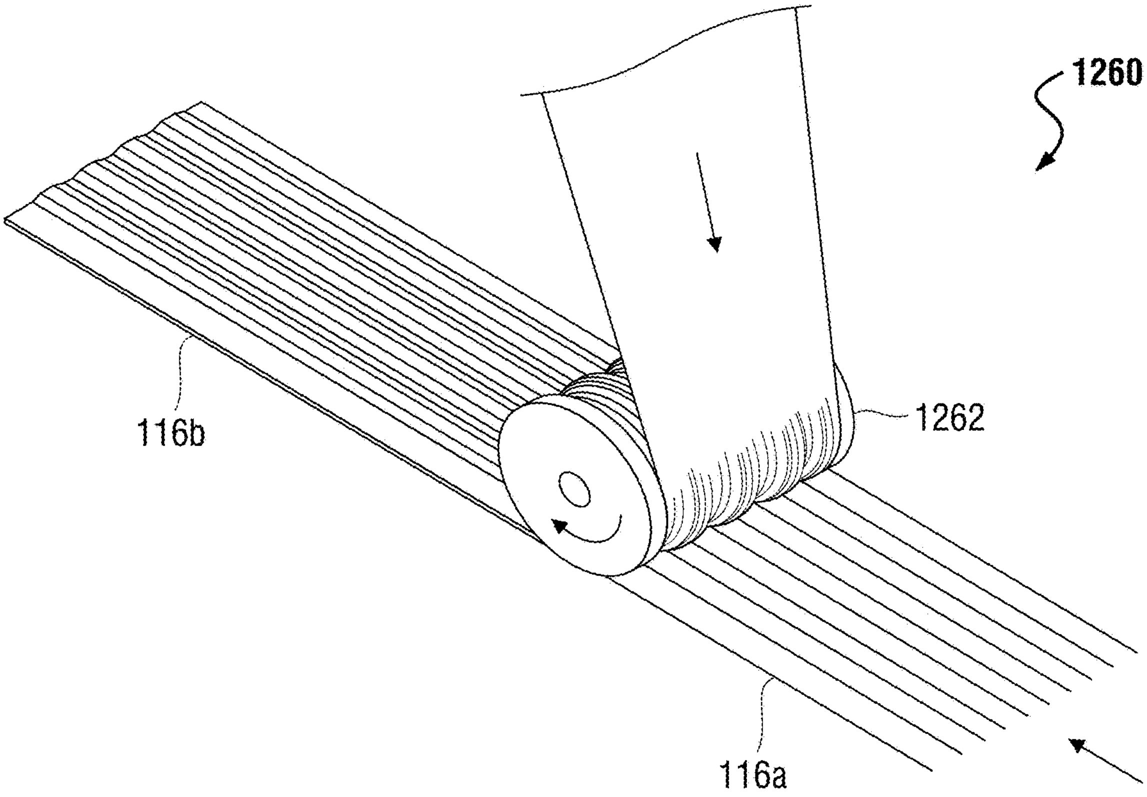
FIGS. 12H-12K depict a grooved form roller, portions thereof, and the use thereof.
Figure 12I:
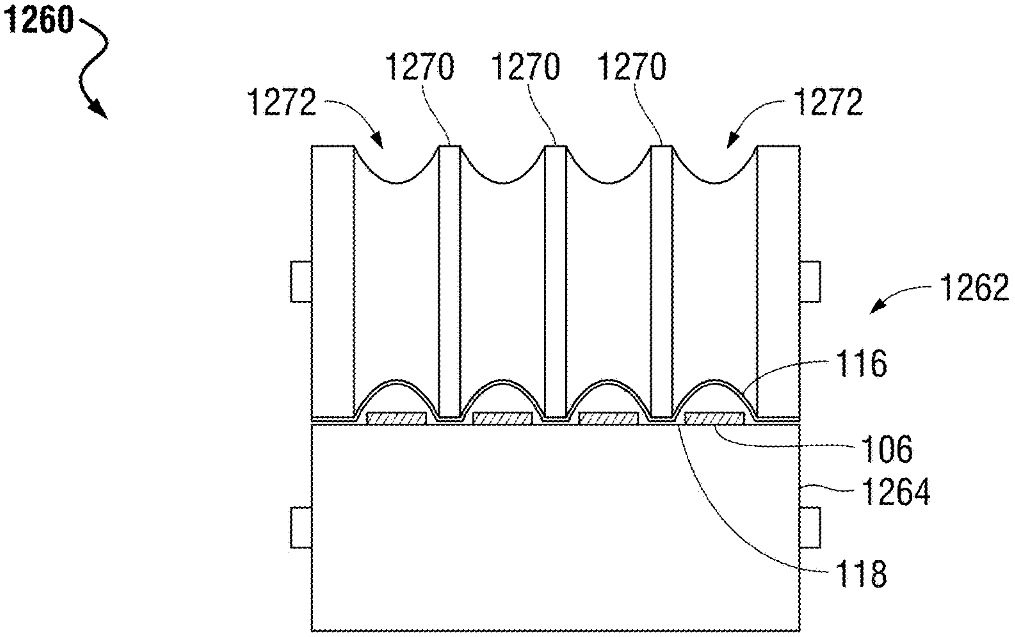
Figure 12J:
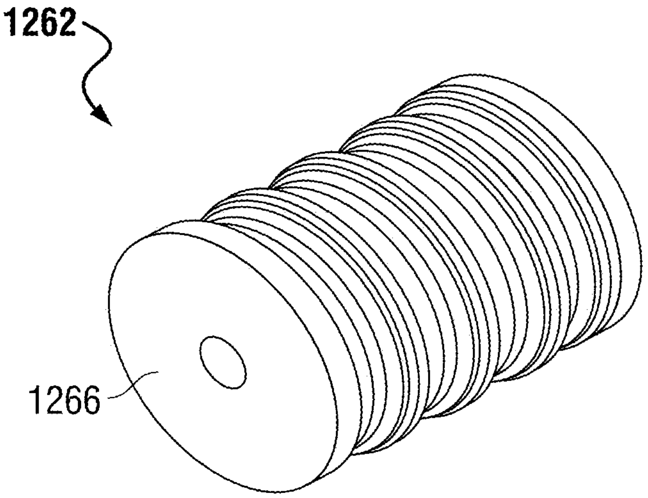
Figure 12K:
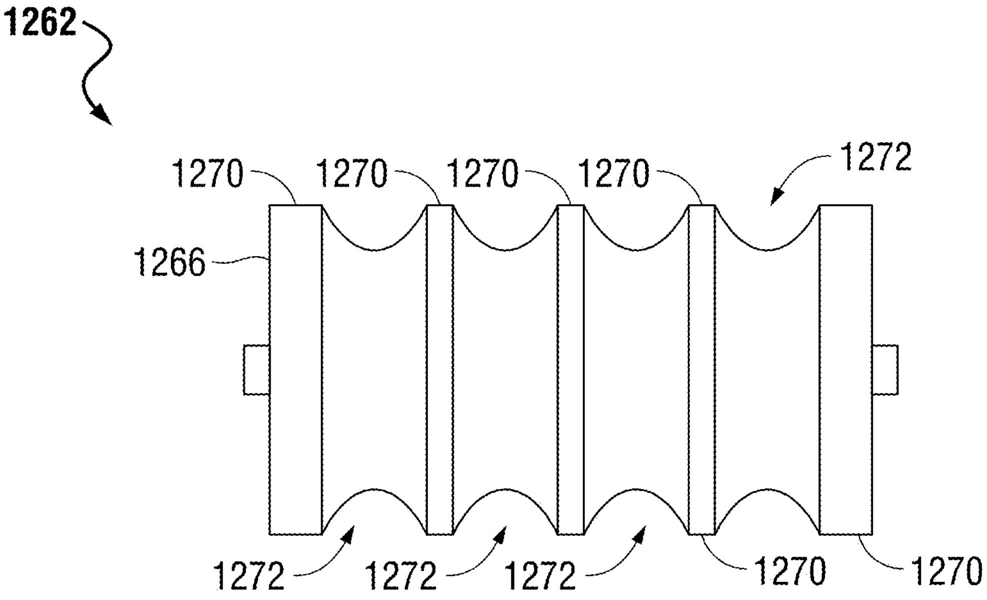
Figure 18:
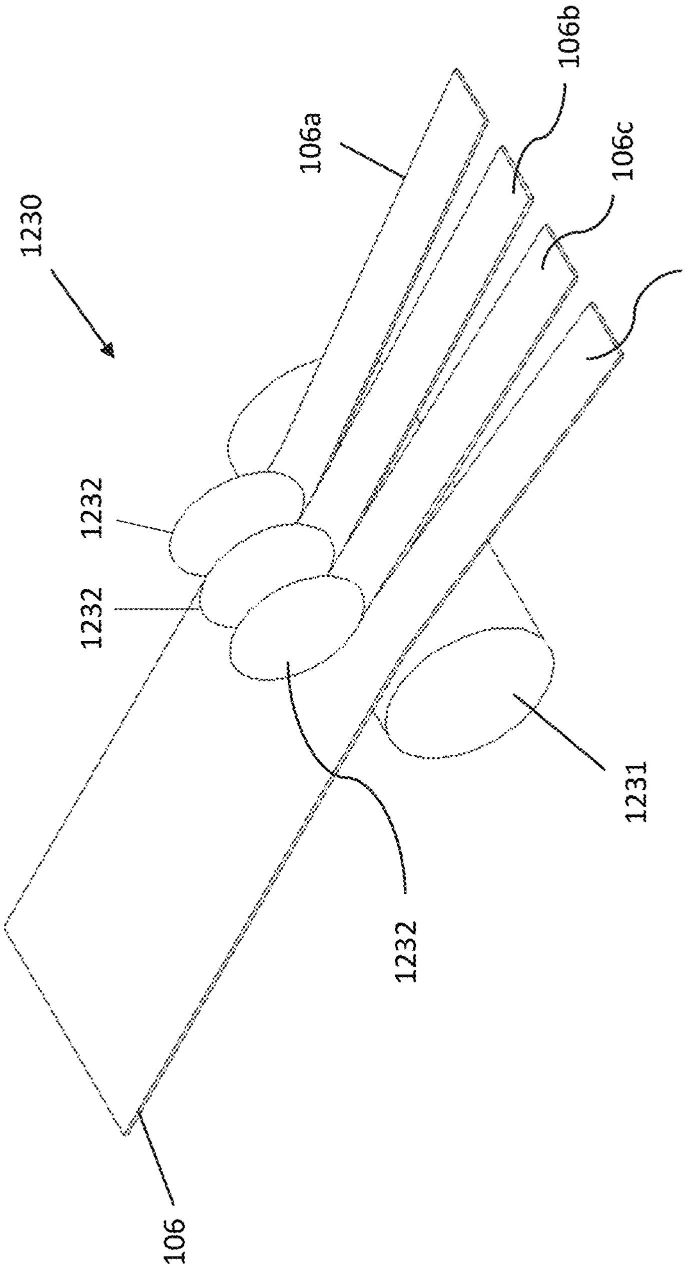
FIG. 18 depicts the cutting of a bulky nonwoven into sections.

After application of SAP to fibrous construction 106, fibrous construction 106 passes to layer separator 1230. Layer separator 1230 may slit, cut, or otherwise separate fibrous construction 106 into multiple sections, such as the four sections shown in FIG. 4A. Layer separator 1230 may be or include knifes or other cutting or slitting apparatus for separating fibrous construction 106. For example, FIGS. 12E and 12F depict fibrous construction 106 before and after passing over knives 1232 of layer separator 1230, respectively, to form fibrous construction sections 106*a*-106*d*. In aspects where a nonwoven capture sheet is included, the nonwoven capture sheet may or may not be cut, along with the fibrous construction 106. In other aspects, fibrous construction 106 is not slit or cut. FIG. 12G depicts one exemplary core 100 that includes cut nonwoven capture sheets 1208*a*-1208*d* positioned below fibrous construction sections 106*a*-106*d*. Core 100 of FIG. 12G is otherwise identical to that of FIG. 5. In some aspects, cutting fibrous construction 106 into fibrous construction sections 106*a*-106*d* results in a densification on the lateral side edges of fibrous construction sections 106*a*-106*d* as a result of contact with the cutting apparatus. For example, fibrous construction sections 106*a*-106*d* in FIG. 12F each have a densified lateral side edges 103. Such densified lateral side edges may facilitate retention of SAP in the fibrous construction sections 106*a*-106*d* as well as wicking (as a result of the denser fiber packing). FIG. 18 depicts another exemplary layer separator 1230 including circular knives 1232, such as a slitting roll (crush cut) positioned adjacent one surface of fibrous construction 106 and an opposing roller 1231 such as a slitting anvil positioned on the opposite surface thereof. As fibrous construction 106 passes between roller 1231 and knives 1232, fibrous construction 106 is separated into fibrous construction sections 106*a*-106*d*.

The thus cut fibrous construction 106 then passes to combining rollers 1240, where fibrous construction 106 is combined with intermediate nonwoven sheet 118. Intermediate nonwoven sheet 118 may be dispensed from roller 1242. In some aspects, adhesive (e.g., 120 shown in FIG. 5) is applied to intermediate nonwoven sheet 118 prior to being combined with fibrous construction 106, such as via adhesive applicator 1244. Intermediate nonwoven sheet 118 and fibrous construction 106 pass through combining roller 1240 to be pressed together via force from the rollers.

Beads of adhesive are then applied by bead adhesive applicator 1250 to intermediate nonwoven sheet 118 in the spaces between the sections of fibrous construction 106 (e.g., beads 122 as shown in FIG. 5).

Upper nonwoven sheet 116 is then combined with fibrous construction 106 and intermediate nonwoven sheet 118. Upper nonwoven sheet 116 is dispensed from spool 1252, passes over rollers 1254, and is combined with fibrous construction 106 and intermediate nonwoven sheet 118 via combining roller 1260, forming upper absorbent construction 102. In some aspects, combining roller 1260 includes one or a series of rollers that compress upper nonwoven sheet 116, fibrous construction 106 and intermediate nonwoven sheet 118 together. In other aspects, combining roller 1260 is or includes a grooved form roller 1262 (FIGS. 12H-12L) having a surface that is contoured to form undulations in upper nonwoven sheet 116 to result in the undulated upper nonwoven sheet 116, such as is shown in FIG. 5.

Grooved form roller 1262 includes roller body having a series of peaks 1270 and valleys 1272. As substantially flat upper nonwoven sheet 116*a* passes over grooved form roller 1262, upper nonwoven sheet 116*a* is conformed to the undulating surface (peaks and valleys) of form roller body 1266. In some such aspects, air suction is provided to pull upper nonwoven sheet 116*a* onto undulating surface of form roller body 1266. As such, undulated upper nonwoven sheet 116*b* is formed. Combining roller 1260 may also include lower roller 1264, which may have a smooth surface rather than an undulating surface, for compressing together upper nonwoven sheet 116, fibrous construction 106 and intermediate nonwoven sheet 118, forming upper absorbent construction 102.

Upper absorbent construction 102 then passes over rollers 1280 to combining roller 1282 for combining with lower absorbent construction 104. In some aspects, adhesive is applied to upper absorbent construction 102 via adhesive applicator 1284 (e.g., adhesive 128 of FIG. 5).

To make lower absorbent construction 104, nonwoven sheet 132 is dispensed from spool 1300, and adhesive is applied thereto via adhesive applicator 1302. Nonwoven sheet 132 is passed to core form 1306 (e.g., a vacuum drum), where pulp 1304 is applied thereto. In some aspects, SAP fines 400*d* from diverter stream 1224 is combined with pulp 1304, passes over X-form roller 1308, is sprayed with adhesive via adhesive applicator 1310 (e.g., 134*a* and/or 134*b* in FIG. 5), and is folded at folding board 1312; thereby, forming lower absorbent construction 104. In some aspects, pulp 1304 is formed using a hammermill. Lower absorbent construction 104 then passes to combining roller 1282, where it is combined with upper absorbent construction 102 to form a sheet of core material 100, which may be collected onto a spool for subsequent use (e.g., incorporation into an absorbent article). In some aspects, core 100 is immediately combined with an absorbent article, rather than being collected. In some aspects, core 100 does not include lower absorbent construction 104.

Figure 19:
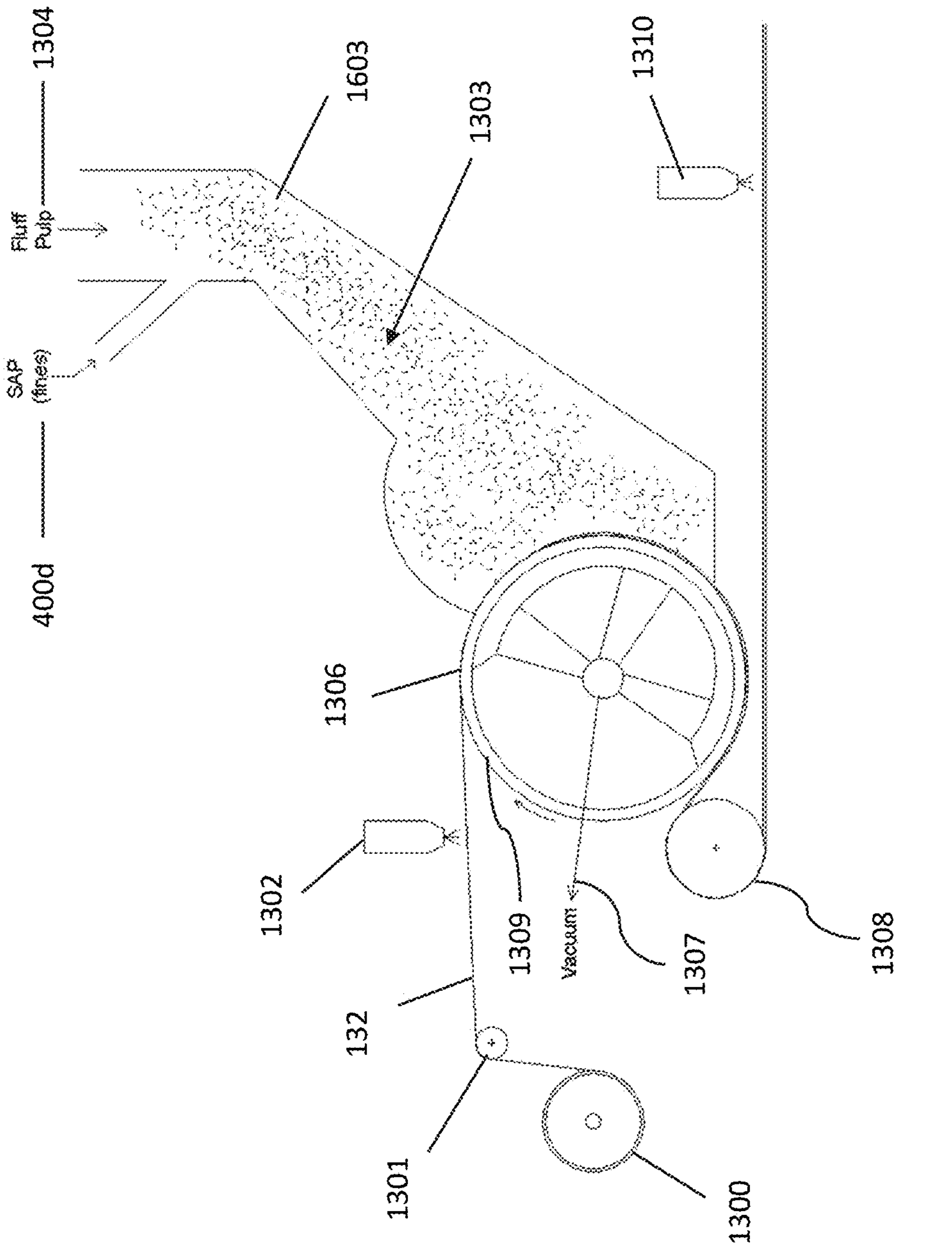
FIG. 19 depicts a detail view of the making of a pulp-SAP layer.
Figure 20A:
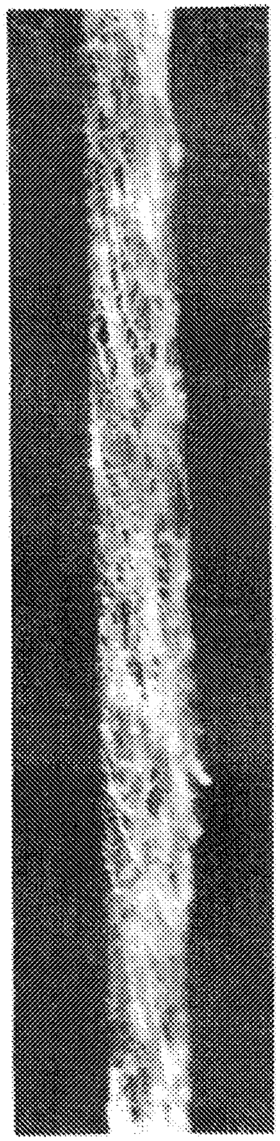
FIGS. 20A-20E depict creped spunbond nonwovens.
Figure 20B:
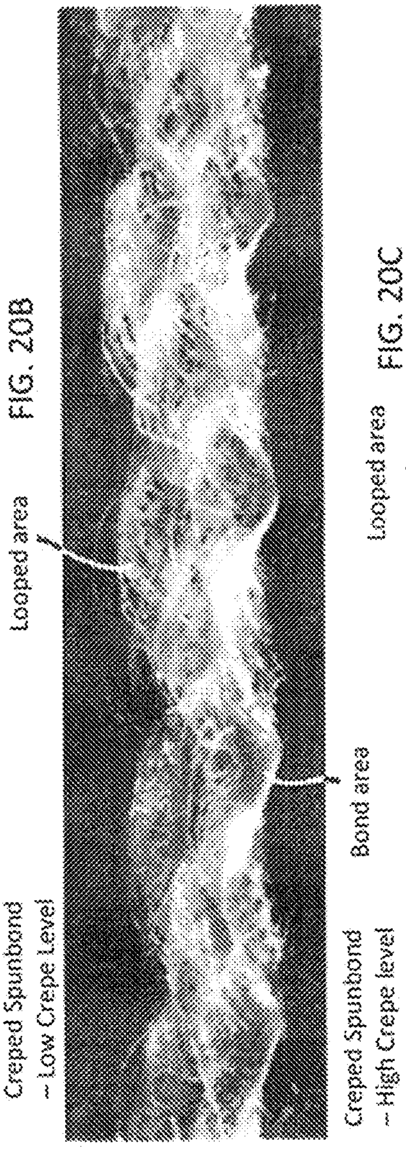
Figure 20C:
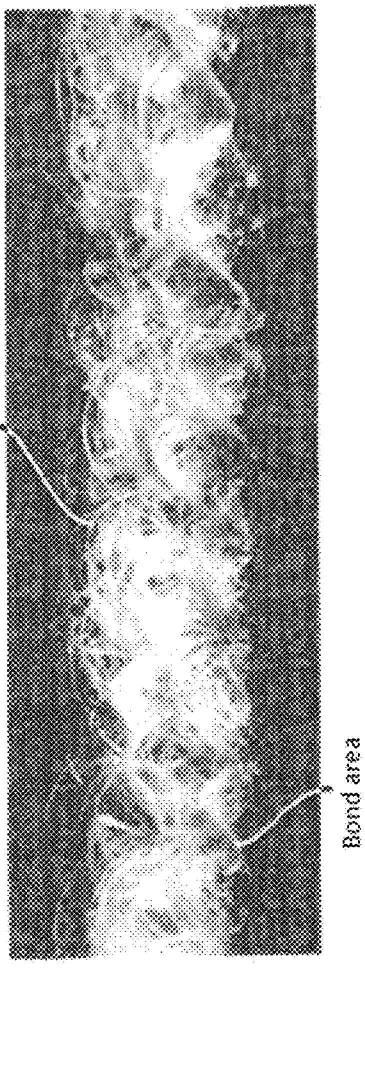
Figures 20D, 20E:
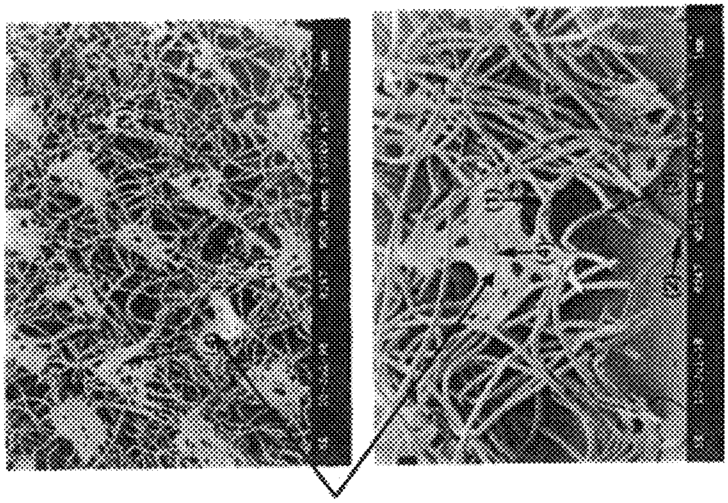

FIG. 19 depicts a more detailed view of a portion of the lower absorbent construction 104 production equipment. Nonwoven sheet 132 is unwound from spool 1300, passes over roller 1301, and is subjected to a hot melt application via applicator 1302. Within core forming chamber 1603, airflow into the chamber carries and mixes fluff pulp fibers 1304 and SAP fines 400*d*, forming a SAP and fluff pulp mixture 1303, which is then drawn onto and deposited onto the core wrap nonwoven sheet 132 via vacuum 1307. Core forming drum 1306 may include a mesh screen 1309 over which the nonwoven sheet 132 is placed, and vacuum 1307 draws air through the mesh 1309 in the core forming region, forming a fluff-pulp core with SAP fines 400*d* thereon. Transfer roller 1308 draws the nonwoven sheet 132, with fluff and SAP thereon, off the core forming drum 1306, and is optionally subjected to a hot melt application via applicator 1310 to provide core integrity.

Figure 13:
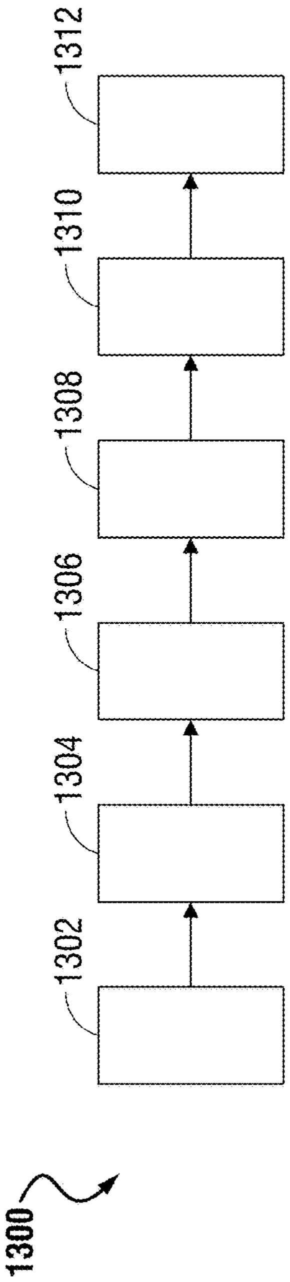
FIG. 13 is a simplified flow chart of a process of making an absorbent core.

FIG. 13 is a process flow chart of one exemplary method of making the absorbent cores disclosed herein. Method 1300 includes: depositing SAP onto a bulky nonwoven, 1302; separating the bulky nonwoven into multiple, longitudinal sections, 1304; placing a first nonwoven sheet on a first surface of the bulky nonwoven sections, 1306; placing a second nonwoven sheet a second surface of the bulky nonwoven, where the second surface is opposite the first surface, 1308; adhering the second nonwoven sheet to the first nonwoven sheet at locations between the multiple, longitudinal sections of the bulky nonwoven, 1310; and forming undulations in the second nonwoven sheet; thereby, forming an upper absorbent construction, 1312.

Figure 14:
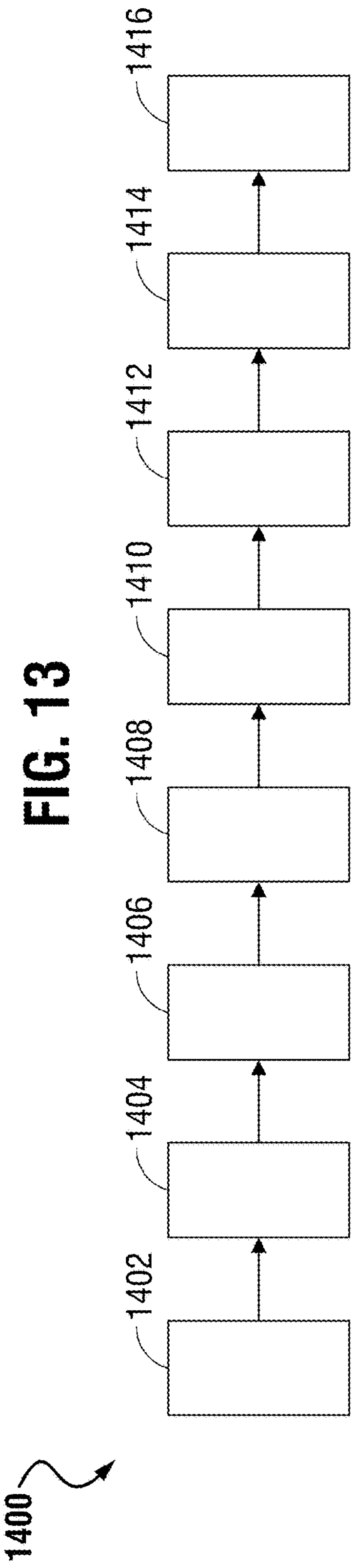
FIG. 14 is another simplified flow chart of a process of making an absorbent core.

FIG. 14 is a process flow chart of one exemplary method of making the absorbent cores disclosed herein. Method 1400 includes: tackifying a bulky nonwoven, 1402; placing a nonwoven capture sheet on the bulky nonwoven, 1404; depositing SAP onto the bulky nonwoven from a high velocity SAP-containing airstream, 1406; separating the bulky nonwoven into multiple, longitudinal sections, 1408; placing a first nonwoven sheet on the nonwoven capture sheet, 1410; placing a second nonwoven sheet on a second surface of the bulky nonwoven using a grooved form roller, opposite the first nonwoven sheet, 1412; adhering the second nonwoven sheet to the first nonwoven sheet at locations between the multiple, longitudinal sections of the bulky nonwoven, 1414; and forming undulations in the second nonwoven sheet; thereby, forming an upper absorbent construction, 1416.

Figure 15:
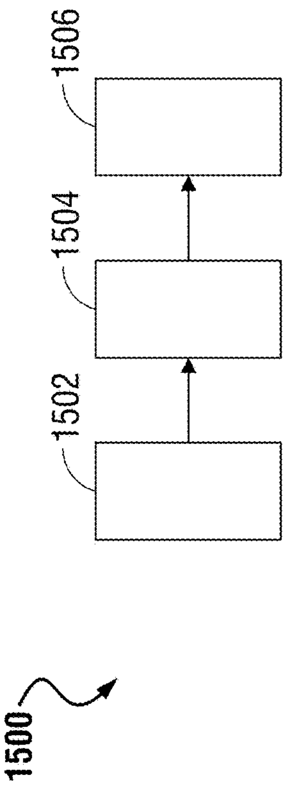
FIG. 15 is a simplified flow chart of a process of making a pulp layer.

FIG. 15 is a process flow chart for one exemplary method of making absorbent core disclosed herein. Method 1500 includes depositing pulp and SAP onto a nonwoven sheet, 1502. In some aspects, the SAP is diverted from SAP that has filtered through a bulky nonwoven, such as in method 1300 or 1400. Method 1500 includes folding the nonwoven about the pulp and SAP to form a lower absorbent construction, 1504. Method 1500 includes combining the lower absorbent construction with an upper absorbent construction, 1506. The upper absorbent construction of step 1506 may be the one formed in method 1300 or method 1400, for example.

Extruded Nonwoven

In some embodiments, the fibrous construction is or includes an extruded nonwoven that contains SAP. For example, such a nonwoven may be formed in accordance with the methods disclosed in U.S. Pat. No. 5,720,832, the entirety of which is incorporated herein by reference. Thus, rather than adding SAP to an existing bulky nonwoven, nonwoven forming polymers (e.g. polypropylene, polyethylene acetate) are extruded around superabsorbent particles to form an absorbent web of nonwoven fibers that surround and entrap the superabsorbent in a SAP-nonwoven composite. The superabsorbent in such a pre-formed SAP-nonwoven composite may be in particle form or fiber form.

Figure 21:
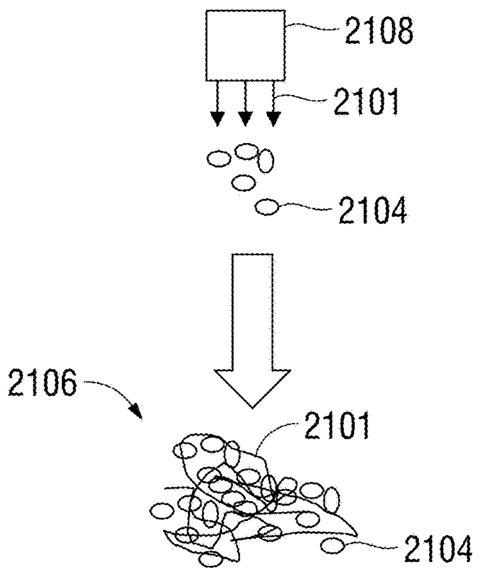
FIG. 21 is a schematic of a process for extruding fibers onto SAP to form a SAP-fiber composite.

For example, with reference to FIG. 21, nonwoven forming polymers 2101 are extruded from extruded 2108 around superabsorbent particles 2104 to form an absorbent web of nonwoven fibers that surround and entrap the superabsorbent, SAP-nonwoven composite 2106.

Fibrous Construction Additives

In some embodiments, the nonwoven of the fibrous construction (bulky or extruded in situ) contain fibers and additives that impart additional properties to the absorbent construction, in addition to the property of stabilizing the SAP particles. For example, and without limitation, the fibrous construction may include elastomeric fibers to provide elasticity, stretch, and body conforming properties; wetting agents to provide and/or enhance fluid handling capability; odor control agents; ion-exchange resins; cellulose fibers, such as microfibrillated cellulose (MFC); and smart fiber.

Profiling the Absorbent Construction

In some embodiments, the SAP is varied from one region to another in the absorbent core. For example, the type of SAP, the amount of SAP, the particle size of SAP, and/or the properties of the SAP may be varied. For example, SAP in one or more regions may have a relatively low permeability, such as at the side sections of the core, and SAP in one or more other regions may have a relatively high permeability at the central regions (crotch).

In some embodiments, the absorbent core has a profiled absorption capacity in the machine direction (MD), which corresponds with the longitudinal centerline 110 shown in FIG. 4A. For example, the SAP dosing may be varied in the machine direction. In some embodiments, the absorbent core has a profiled absorption capacity in the cross direction (CD), which corresponds with the lateral centerline 108 shown in FIG. 4A. For example, the SAP loading may be varied in the CD in different SAP regions, and the width of the SAP regions may be varied. The number of SAP regions may also be varied.

Figure 22:
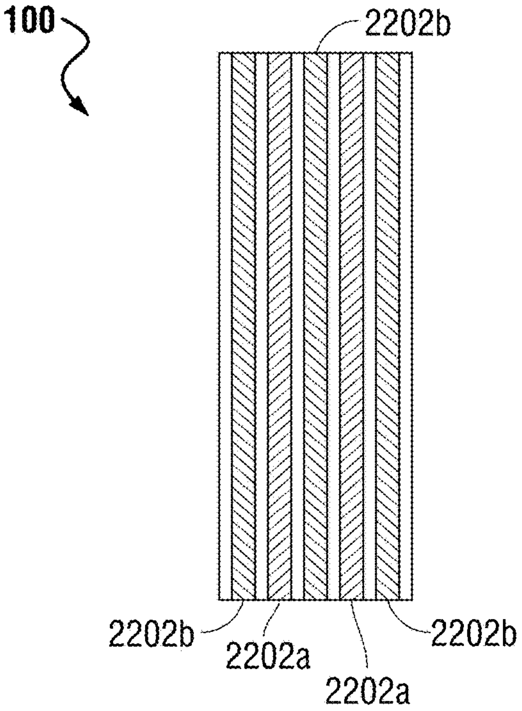
FIG. 22 is an absorbent core having laterally spaced apart sections of different SAP concentrations.
Figure 23:
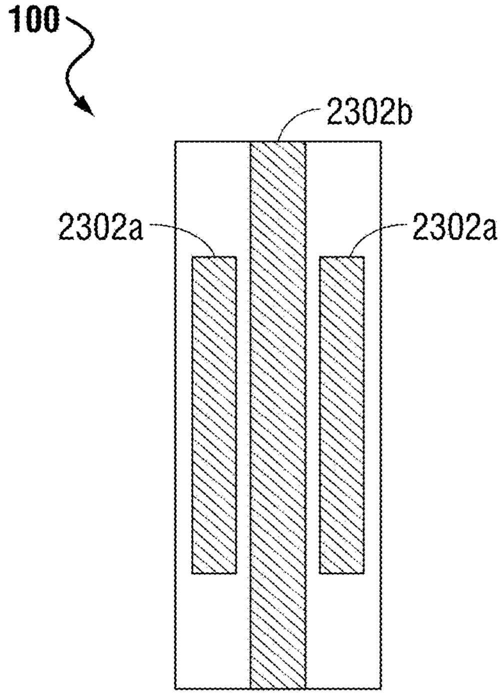
FIG. 23 is an absorbent core having lanes of SAP concentrations of varying longitudinal lengths.
Figure 24:
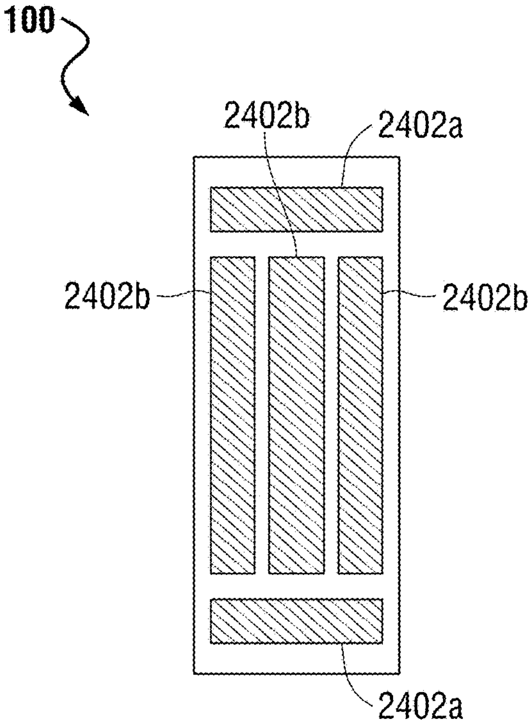
FIG. 24 is an absorbent core having laterally and longitudinally extending lanes of SAP concentrations.
Figure 25:
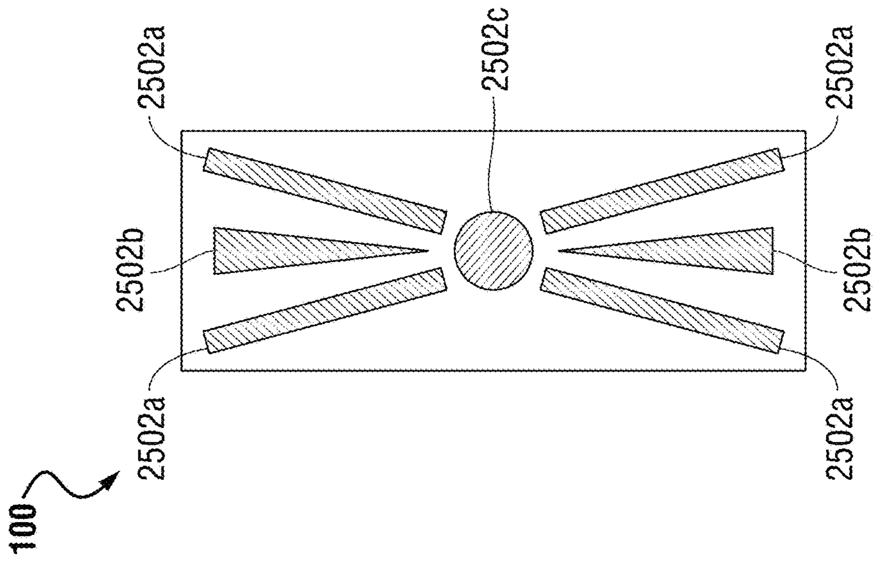
FIG. 25 is an absorbent core having a pattern of SAP concentrations arrange, including SAP concentrations that extend at angles relative to the lateral and longitudinal centerlines of the absorbent core.

The cut lengths of the absorbent fibrous sections may be varied in each channel. FIG. 22 depicts core 100 with SAP regions 2202*a* and SAP regions 2202*b*. SAP region 2202*a* may be different from SAP region 2202*b* in the SAP loading, SAP type, SAP particle size, SAP properties, or combinations thereof. FIG. 23 depicts core 100 with relatively short SAP regions 2302*a* at the sides and relatively long SAP regions 2302*b* at the center. FIG. 24 depicts core 100 with SAP regions 2402*a* at the longitudinal ends of core 100 and SAP regions 2402*b* at the center. FIG. 25 depicts core 100 with SAP regions 2502*a* that extend at an angle relative to the longitudinal centerline of core 100, triangular shaped SAP regions 2502*b*, and centrally located circular SAP region 2502*c*. In each of FIGS. 23-25, each different SAP region may be the same as or different than other SAP regions in terms of SAP loading, type, size, and/or properties.

Figure 27:
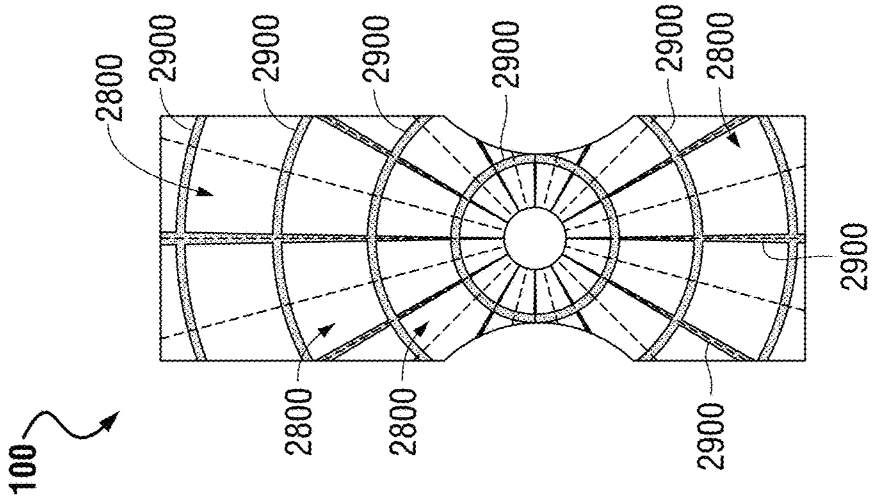
FIGS. 26 and 27 are absorbent core with a pattern of SAP concentrations radiating from a central crotch region of the cores.
Figure 26:
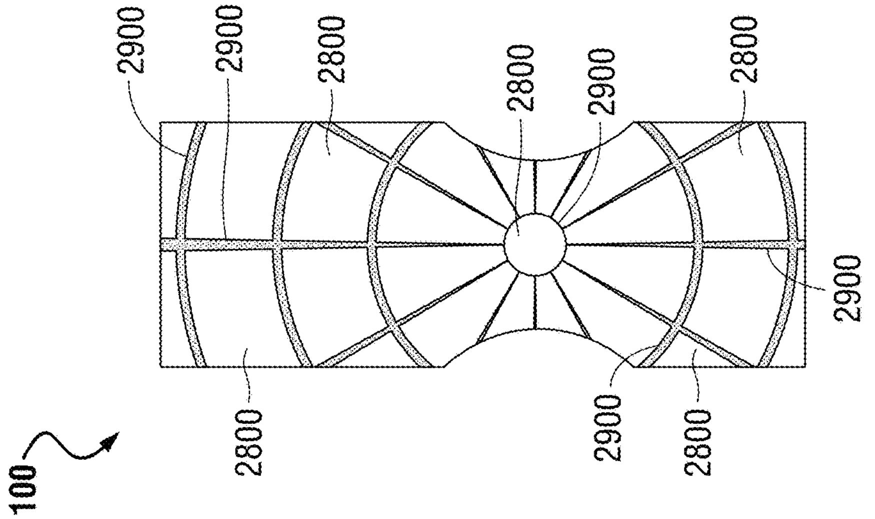

FIGS. 26 and 27 shown embodiments of SAP deposition geometries that may be utilized in the cores 100 disclosed herein. Each SAP region 2800 (shown as the non-shaded areas in cores 100), is separated from other SAP regions 2800 via gaps 2900, which contain no SAP or other absorbent material. As discussed elsewhere herein, some of the gaps 2900 may function as channels and/or fold lines for the core 100. Each separate SAP region 2800 may be the same as or different than the other of the SAP regions 2800 in terms of SAP loading, type, size, and/or properties.

In some embodiments, the SAP is varied in both the CD and MD, such as by using shaped absorbent section. By stacking the absorbent regions, having multiple stripes of absorbent regions of different lengths, absorbent regions with different shapes and orientations having different SAP and SAP loadings can be achieved.

Figure 28:
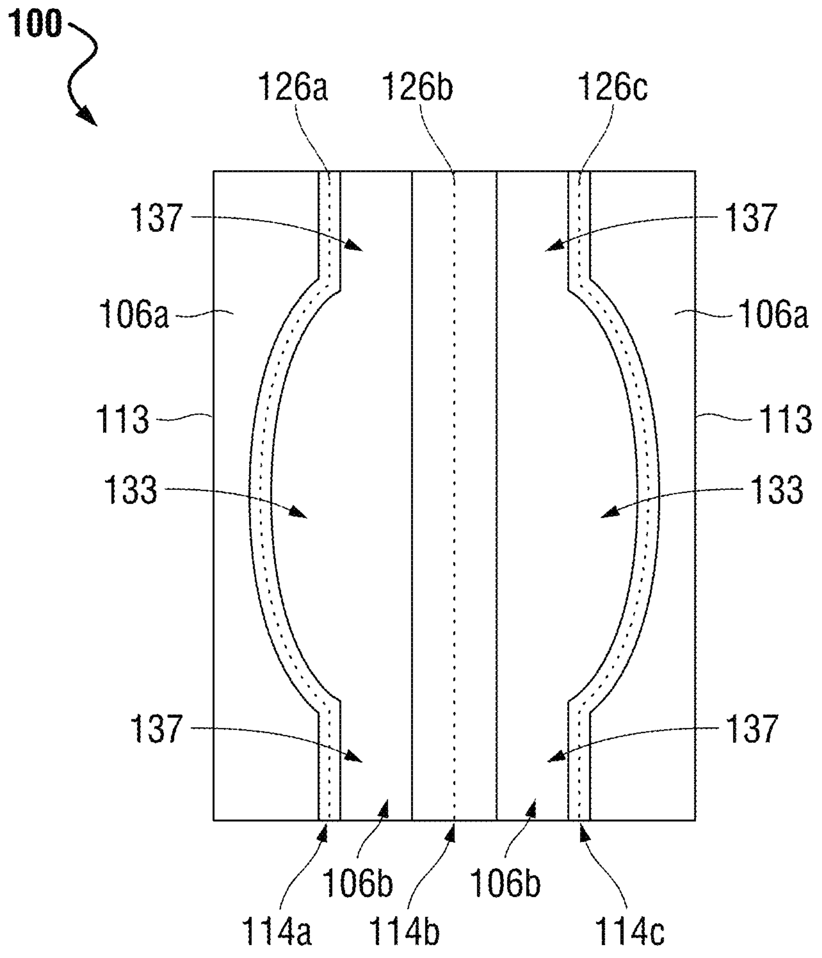
FIG. 28 is an absorbent core having curvilinear patterns of SAP concentrations.

In some embodiments, the fibrous section is cut to have a width that various long the longitudinal centerline of the core. For example, FIG. 28 depicts core 100 having fibrous sections **106*b* that contain SAP, which include centrally located expanded regions 133 that extend closer to the lateral side edges 113 of core 100 than narrower regions 137. Core 100 also includes fibrous sections 106*a* that contain SAP. Fibrous sections 106*a* may contain a smaller SAP loading than fibrous sections 106*b*. From FIG. 28**, it is evident that the regions of SAP can be shaped and positioned such that the larger amounts of highly absorbent SAP can be strategically positioned at the crotch region, where needed. The fibrous sections can be cut to have non-linear, e.g. curvilinear perimeters. In some embodiments, multiple (e.g., two) relatively high SAP content regions can come be formed from one sheet of fibrous construction with little or no waste. For example, a sheet of fibrous construction can be cut to have an S-shaped cut pattern, and then one side of the S-shaped sheet half can be flipped over and moved into a position that is out of phase relative to the other sheet half such that the patterns match.

Aspects and Variations

In some aspects, the absorbent core disclosed herein provides for bulky, high loft absorbent structure having a low density and high volume, and providing a soft fit and fast absorbing properties. In certain aspects, the absorbent core is a multilayer composite core structure, having both an upper and lower absorbent construction. Each layer or construction may be tailored to have a specific function, such as absorption or distribution.

The absorbent core disclosed herein is capable of fitting users well, especially in the narrow part of the crotch between the legs. The absorbent core readily adopts a 'W-shape' configuration, which allows the core to narrow and reduce lateral flow of fluid to the sides of the core; thereby, reducing leakage from the sides of the absorbent product.

In some aspects, core 100 has a lateral width ranging from about 70 to about 200 mm, or from 80 to 170 mm, or from 90 to 150 mm, or from 100 to 130 mm. In some aspects, core 100 has a basis weight of from about 30 to about 60 gsm or higher. In some aspects, the thickness of each fibrous construction section **106*a*-106*d* is from 2 to 10 mm, or from 4 to 8 mm, or from 5 to 7 mm. In some aspects, the thickness of pulp layer 130 is from 2 to 10 mm, or from 4 to 8 mm, or from 5 to 7. In some aspects, the thickness of the core is from 5 to 20 mm, or from 8 to 15 mm, or from 10 to 12, or from 6 to 10 mm. The core width may be about 100 mm for baby diapers, 140-150 for adult diapers, or from 80-170 mm. The lower core construction may have the same width as the upper core construction, or be slightly larger than the composite of materials that make up the upper core construction. In some aspects, the BNW is from 1-3 mm thick, depending on the basis weight and density thereof. In some aspects, the lower absorbent construction (e.g., the pulp layer) is less than about 2 mm thick, or from 0.5 to 1.7 mm thick, and has a low basis weight. In some aspects, the spunbond nonwovens disclosed herein have a thickness of less than 0.2 mm. In certain aspects, the absorbent cores disclosed herein are pre-fabricated, and capable of being spooled or festooned for shipment and use on a diaper line. In some aspects, the core 100** is a pre-fabricated absorbent core, provided on a roll, spool or festoon, that is soft, cost-effective and has better absorption properties that other absorbent core designs, including those having mixtures of fluff pulp and SAP.

In some aspects, the SAP to BNW ratio within fibrous construction 106 is from 3:1 to 15:1 or 5:1 to 10:1, by weight. In some aspects, the SAP to fluff ratio in pulp layer 130 is from 1:10 to 2:1, or 5:10 to 1:1, by weight.

In some aspects, fibrous construction sections **106*a*-106*d*** include a basis weight of bulky nonwoven ranging from about 30 to 120 gsm, or 50 to 100 gsm, or 60 to 80 gsm; a basis weight of SAP of from 150 to 800 gsm, or from 200 to 700 gsm, or from 300 to 600 gsm, or from 400 to 600 gsm; and a basis weight of adhesive of from 0 to 25 gsm, or from 1 to 20 gsm, or from 5 to 15 gsm, or from 10 to 12 gsm.

While the use of adhesive has been described herein, in some aspects the use of adhesive is replaced with ultrasonic bonding.

In some aspects, the core 100 includes wing sections defining the lateral margins on opposite sides of the core 100. For example, with reference to FIG. 9A, the wing sections may be the raised sections **106*a* and 106*d* of fibrous construction. Each wing section may have a lateral width that is equal to 20 to 40%, 25 to 35%, or from 27.5 to 32.5%, or greater than 20% of an overall width of the core composite 100, when core 100 is in the flat configuration. In some aspects, each middle section of core 100, for example sections of fibrous construction positioned between the raised sections 106*a* and 106*d* (i.e., sections 106*b* and 106*c*) may have a lateral width that is equal to 10 to 50%, 20 to 40%, or from 30 to 35%, or less than 50% of the overall width of the core composite 100, when core 100 is in the flat configuration. In some aspects, the wing sections provide an outboard boundary serving as lateral margins of core 100. In some aspects, core 100 is fixed to the structural layer (e.g., backsheet 202) along bond lines 300 that are coincident with fold lines 126*a* and 126*c*, adjacent inboard boundaries of the wing sections. In some such aspects, fibrous construction sections positioned inboard of bond lines 300 (i.e., fibrous construction sections 106*b* and 106*c***) are free of the structural layer and movable relative of the structural layer.

In some aspects, the absorbent cores disclosed herein provide for relatively thin, but highly absorbent, absorbent core constructions. The absorbent cores disclosed herein may include a laminate of relatively thin, layered materials, including a pulp layer having a low basis weight, in contrast to a typical fluff/SAP diaper that includes a thick fluff layer having a high basis weight.

The fibrous constructions may serve to inhibit SAP migration within the core during manufacture, packaging, and wear of the core and articles including the core. SAP migration may be inhibited during all stages of the product life. Dry SAP may be immobilized by a combination of the entanglement with the nonwoven fibers in the BNW and any adhesive/tackifiers present in the nonwoven. Wet SAP may be immobilized due to entanglement in the fibers in the z-direction of the BNW.

In some such aspects, the absorbent cores disclosed herein are pre-fabricated cores that provide a combination of sufficient softness, thinness, absorbency, wet and dry integrity, and SAP immobilization. The pulp layer of the lower absorbent core construction provides a softness to the touch, as well as an aesthetically and visually beneficial flat and soft appearance, which may be beneficial to consumers during product selection. While, the upper absorbent core construction provides an undulating visual appears that is visually indicative of absorbency. The upper absorbent core construction also provides for the majority of the absorbency of the cores disclosed herein. In particular, the SAP contained within the fiber network provides for the majority of the absorbency of the cores disclosed herein, allowing the fiber network to remain relatively dry. As the fiber network remains relatively dry, the structure integrity of the fiber network is maintained, such that the core is capable of dynamically folding and unfolding during use.

In some aspects, the use of channels, in conjunction with strategically positioning the absorbent core within an article, facilitates retaining an advantageous distribution of SAP within the core, while optimizing thinness of the core. The fibrous network of the fibrous construction exhibits wet integrity, unburdened by fluid retention functions. The SAP contained within the fibrous network may be inhibited from migration, such as via adhesive.

The foregoing descriptions have been presented for purposes of illustration and description. These descriptions are not intended to limit the disclosure or aspects of the disclosure to the specific absorbent core composites and constructions or articles, apparatus and processes disclosed. Various aspects of the disclosure are intended for applications other than diapers and training pants. The absorbent core constructions described may also be incorporated into or with other garments, textiles, fabrics, and the like, or combinations thereof. The absorbent core constructions described may also incorporate different components. Further, the absorbent core composites described may refer to substrates (e.g., composite sheets) of such core composites prior to individualizing and incorporating such absorbent core composites (as discrete absorbent core composites) into disposable absorbent articles. These and other variations of the disclosure will become apparent to one generally skilled in the relevant consumer product art provided with the present disclosure. Consequently, variations and modifications commensurate with the above teachings, and the skill and knowledge of the relevant art, are within the scope of the present disclosure. The embodiments described and illustrated herein are further intended to explain the best modes for practicing the disclosure, and to enable others skilled in the art to utilize the disclosure and other embodiments and with various modifications required by the particular applications or uses of the present disclosure.

What is claimed is:

1. An absorbent core having a longitudinal centerline and a lateral centerline that is transverse to the longitudinal centerline, the absorbent core comprising:

a plurality of laterally spaced-apart fibrous constructions, wherein each fibrous construction is separate, discrete, and spaced-apart from the other fibrous constructions, wherein each fibrous construction extends generally parallel to or coincident with the longitudinal centerline, and wherein the fibrous constructions are pulpless and fluffless;

a first nonwoven sheet positioned on a first side of the fibrous constructions;

a second nonwoven sheet positioned on a second side of the fibrous constructions, opposite the first side of the fibrous construction, wherein the first nonwoven sheet is coupled to the second nonwoven sheet at locations between adjacent laterally spaced-apart fibrous constructions;

wherein each fibrous construction is positioned between the first and second nonwoven sheets;

wherein each fibrous construction comprises a nonwoven having a network of fibers and absorbent material including superabsorbent polymer particles disposed within the network of fibers; and wherein the nonwoven of each fibrous construction is separate, discrete, and spaced-apart from the nonwoven of the other fibrous constructions, and wherein the nonwoven of each fibrous construction is positioned between the first and second nonwoven sheets.

2. The absorbent core of claim 1, further comprising channels at least partially defined by the first nonwoven sheet, wherein each channel is positioned between two adjacent, laterally spaced-apart fibrous constructions and above the first nonwoven sheet, and wherein each channel extends generally parallel to or coincident with the longitudinal centerline.

3. The absorbent core of claim 2, wherein each channel is coincident with a fold line of the first nonwoven sheet.

4. The absorbent core of claim 2, wherein the channels are free of absorbent material.

5. The absorbent core of claim 1, wherein the first nonwoven sheet is adhered to the second nonwoven sheet at locations between adjacent, laterally spaced-apart fibrous constructions.

6. The absorbent core of claim 5, wherein the first nonwoven sheet is adhered to the second nonwoven sheet at locations between adjacent, laterally spaced-apart fibrous constructions via adhesive beads.

7. The absorbent core of claim 1, further comprising fold lines on the first nonwoven sheet, wherein each fold line is positioned between two adjacent, laterally spaced-apart fibrous constructions, and wherein each fold line extends generally parallel to or coincident with the longitudinal centerline of the absorbent core.

8. The absorbent core of claim 7, wherein the absorbent core is at least partially foldable along the fold lines.

9. The absorbent core of claim 8, wherein the absorbent core has a first lateral extent prior to folding along the fold lines and a second lateral extend after folding along the fold lines, and wherein the first lateral extent is greater than the second lateral extent.

10. The absorbent core of claim 8, wherein, when folded along the fold lines, the absorbent core has a generally W-shaped lateral cross-section.

11. The absorbent core of claim 10, wherein the W-shaped lateral cross-section is within a crotch region of the absorbent core.

12. The absorbent core of claim 8, wherein, when folded, two of the plurality of laterally spaced-apart fibrous constructions form laterally positioned wing sections of the absorbent core.

13. The absorbent core of claim 12, wherein the laterally positioned wing sections have a lateral width that is equal to about 20% to 40% of a total width of the absorbent core.

14. The absorbent core of claim 1, wherein the first nonwoven sheet has an undulating outer surface, the second nonwoven sheet has a flat outer surface, and the plurality of laterally spaced-apart fibrous constructions are positioned between inner surfaces of the first and second nonwoven sheets.

15. The absorbent core of claim 1, wherein each laterally spaced-apart fibrous construction is sealed along lateral side edges thereof.

16. An absorbent article comprising:

an absorbent core;

a chassis, including a backsheet and a topsheet;

wherein the absorbent core is positioned between the topsheet and the backsheet and is coupled with the backsheet;

the absorbent core having a longitudinal centerline and a lateral centerline that is transverse to the longitudinal centerline, the absorbent core comprising:

a plurality of laterally spaced-apart fibrous constructions, wherein each fibrous construction extends generally parallel to or coincident with the longitudinal centerline, and wherein the fibrous constructions are pulpless and fluffless;

a first nonwoven sheet positioned on a first side of the fibrous constructions;

a second nonwoven sheet positioned on a second side of the fibrous constructions, opposite the first side of the fibrous construction;

wherein the first nonwoven sheet is coupled with the second nonwoven sheet at locations between adjacent, laterally spaced-apart fibrous constructions; and wherein each fibrous construction is positioned between the first and second nonwoven sheets such that the first nonwoven sheet and the second nonwoven sheet separately encapsulate each fibrous construction;

wherein each fibrous construction comprises a bulky nonwoven having a network of hydrophilic and non-absorbent fibers and absorbent material including superabsorbent polymer particles disposed within the network of fibers of the bulky nonwoven; and wherein the bulky nonwoven of each fibrous construction is separate, discrete, and spaced-apart from the bulky nonwoven of the other fibrous constructions, and wherein each bulky nonwoven is positioned between the first and second nonwoven sheets.

17. The absorbent article of claim 16, further comprising channels at least partially defined by the first nonwoven sheet, wherein each channel is positioned between two adjacent, laterally spaced-apart fibrous constructions and above the first nonwoven sheet, wherein each channel extends generally parallel to or coincident with the longitudinal centerline.

18. The absorbent core of claim 1, further comprising nonwoven capture sheets coupled with each fibrous construction, wherein each nonwoven capture sheet is positioned between one of the fibrous constructions and the second nonwoven sheet, wherein each nonwoven capture sheet coupled with one of the fibrous constructions has a density that is higher than a density of the nonwoven in that fibrous constructions.

19. The absorbent core of claim 1, further comprising a third nonwoven sheet coupled with the second nonwoven sheet.

20. The absorbent core of claim 1, wherein each laterally spaced-apart fibrous construction has a gradient distribution of SAP particle sizes in a z-direction, wherein the z-direction is transverse to the longitudinal and lateral centerlines;

wherein, within the SAP gradient distribution of SAP particle sizes, larger particle sizes of SAP are positioned closer to the first nonwoven sheet than the second nonwoven sheet, and smaller SAP particle sizes of SAP are positioned closer to the second nonwoven sheet than the first nonwoven sheet;

wherein each fibrous construction has a gradient distribution of adhesive concentration in the z-direction; and wherein, within the gradient distribution of adhesive concentration, a lower concentration of adhesive is positioned closer to the first nonwoven sheet than the second nonwoven sheet, and a higher concentration of adhesive is positioned closer to the second nonwoven sheet than the first nonwoven sheet.

21. The absorbent article of claim 16, further comprising a plurality of fold lines on an outer surface of the first nonwoven sheet, wherein each fold line is positioned between two of the laterally spaced-apart fibrous constructions, and wherein the plurality of fold lines include a first fold line and a second fold line; and wherein the absorbent core is coupled with the backsheet along the first fold line, and wherein the absorbent core is free of the backsheet along the second fold line.

22. The absorbent article of claim 21, wherein the absorbent core is free of coupling with the backsheet along the second fold line such that an airflow channel is formed between the absorbent core and the backsheet beneath the second fold line.

23. The absorbent core of claim 1, wherein each nonwoven of the fibrous constructions comprises air-through nonwoven.

24. The absorbent core of claim 1, wherein each nonwoven of the fibrous constructions comprises synthetic nonwoven.

25. The absorbent core of claim 1, wherein each nonwoven of the fibrous constructions comprises meltblown nonwoven, spunbond nonwoven, or combinations thereof.

26. The absorbent core of claim 1, wherein each nonwoven of the fibrous constructions comprises polyolefin fibers.

27. The absorbent core of claim 1, wherein each nonwoven of the fibrous constructions comprises polypropylene fibers, polyethylene fibers, polyethylene terephthalate fibers, or polylactic acid fibers.

28. The absorbent core of claim 1, wherein each nonwoven of the fibrous constructions comprises a bulky nonwoven that is an open, fibrous network of hydrophilic, non-absorbent fibers.

29. The absorbent core of claim 1, wherein each nonwoven of the fibrous constructions comprises crepe spunbond.

30. The absorbent core of claim 1, wherein each fibrous construction lacks an absorbent matrix.

31. An absorbent article comprising:

an absorbent core;

a chassis, including a backsheet and a topsheet;

wherein the absorbent core is positioned between the topsheet and the backsheet and is coupled with the backsheet;

the absorbent core having a longitudinal centerline and a lateral centerline that is transverse to the longitudinal centerline, the absorbent core comprising:

a plurality of laterally spaced-apart fibrous constructions, wherein each fibrous construction extends generally parallel to or coincident with the longitudinal centerline;

a first nonwoven sheet positioned on a first side of the fibrous constructions;

a second nonwoven sheet positioned on a second side of the fibrous constructions, opposite the first side of the fibrous construction;

wherein the first nonwoven sheet is coupled with the second nonwoven sheet at locations between adjacent, laterally spaced-apart fibrous constructions;

wherein each fibrous construction comprises a nonwoven having a network of fibers and absorbent material including superabsorbent polymer particles disposed within the network of fibers;

and wherein each nonwoven of the fibrous constructions is separate, discrete, and spaced-apart from the other nonwovens of the fibrous constructions, and wherein the fibrous constructions, including the nonwoven and the absorbent material, are positioned between the first and second nonwoven sheets;

a plurality of fold lines in the first absorbent core construction on an outer surface of the first nonwoven sheet, wherein each fold line is positioned between two of the laterally spaced-apart fibrous constructions, and wherein the plurality of fold lines include a first fold line and a second fold line; and wherein the absorbent core is coupled with the backsheet along the first fold line, and wherein the absorbent core is free of the backsheet along the second fold line such that an airflow channel is formed between the absorbent core and the backsheet beneath the second fold line.

32. The absorbent article of claim 31, wherein the plurality of fold lines include the first fold line, the second fold line, and a third fold line, wherein the second fold line is positioned between the first fold line and the third fold line, wherein the absorbent core is coupled with the backsheet along the first fold line and the third fold line, wherein the absorbent core is free of coupling with the backsheet between the first fold line and the third fold line and along the second fold line such that a continuous airflow channel is formed between the absorbent core and the backsheet and between the first fold line and the third fold line and beneath the second fold line.

33. The absorbent article of claim 32, wherein:

the absorbent core is coupled with the topsheet from the first fold line to a first lateral edge of the absorbent core, and wherein the absorbent core is coupled with the topsheet from the third fold line to a second lateral edge of the absorbent core; or wherein the absorbent core is free of the backsheet between the first fold line and a first lateral edge of the absorbent core, and wherein the absorbent core is free of the backsheet between the third fold line and a second lateral edge of the absorbent core.

34. The absorbent core of claim 1, each nonwoven of the fibrous constructions has a top surface and a bottom surface, and wherein the superabsorbent polymer particles are contained within the network of fibers between the top and bottom surfaces of each nonwoven of the fibrous constructions.

35. The absorbent core of claim 1, wherein the coupling of the first nonwoven sheet to the second nonwoven sheet defines spaces between the first and second nonwoven sheets, and wherein each fibrous construction is contained within one of the spaces between the first and second nonwoven sheets.

36. The absorbent core of claim 35, wherein each nonwoven of the fibrous constructions has a top surface and a bottom surface, and wherein each fibrous construction, from the top surface to the bottom surface thereof, is positioned within one of the spaces between the first and second nonwoven sheets.

37. The absorbent core of claim 35, wherein each space defines a tube that extends generally parallel to or coincident with the longitudinal centerline from a first longitudinal edge of the absorbent core to a second longitudinal edge of the absorbent core, and wherein each fibrous construction is contained within one of the tubes.

38. The absorbent core of claim 35, wherein each fibrous construction is encapsulated between the first nonwoven and the second nonwoven within one of said spaces.

39. The absorbent core of claim 1, wherein each fibrous construction extends generally parallel to or coincident with the longitudinal centerline from a first longitudinal edge of the absorbent core to a second longitudinal edge of the absorbent core.

40. The absorbent core of claim 5, wherein adherence of the first nonwoven sheet to the second nonwoven sheet forms seals that encapsulate the fibrous constructions between the first nonwoven sheet and the second nonwoven sheet.

41. The absorbent core of claim 2, wherein the channels are formed by gaps between adjacent fibrous constructions.

42. The absorbent core of claim 1, wherein the nonwoven of each fibrous construction distinct and disconnected from the nonwoven of each of the other fibrous constructions.

43. An absorbent core having a longitudinal centerline and a lateral centerline that is transverse to the longitudinal centerline, the absorbent core comprising:

a plurality of laterally spaced-apart fibrous constructions, wherein each fibrous construction is separate, discrete, and spaced-apart from the other fibrous constructions, wherein each fibrous construction extends generally parallel to or coincident with the longitudinal centerline, and wherein the fibrous constructions are pulpless and fluffless;

a first nonwoven sheet positioned on a first side of the fibrous constructions;

a second nonwoven sheet positioned on a second side of the fibrous constructions, opposite the first side of the fibrous construction, wherein the first nonwoven sheet is coupled to the second nonwoven sheet at locations between adjacent laterally spaced-apart fibrous constructions, defining spaces between the first and second nonwoven sheets, wherein each space defines a tube that extends generally parallel to or coincident with the longitudinal centerline from a first longitudinal edge of the absorbent core to a second longitudinal edge of the absorbent core, and wherein each fibrous construction is contained within one of said tubes such that each fibrous construction is encapsulated by the first and second nonwoven sheets therein;

wherein each fibrous construction is positioned between the first and second nonwoven sheets and extends generally parallel to or coincident with the longitudinal centerline from the first longitudinal edge of the absorbent core to the second longitudinal edge of the absorbent core;

wherein each fibrous construction comprises a nonwoven having a network of fibers and absorbent material including superabsorbent polymer particles disposed within the network of fibers; and wherein the nonwoven of each fibrous construction is separate, discrete, and spaced-apart from the nonwoven of the other fibrous constructions, and wherein the nonwoven of each fibrous construction is positioned between the first and second nonwoven sheets.

* * * * *